(12) United States Patent
Jones et al.

(10) Patent No.: US 8,404,692 B2
(45) Date of Patent: Mar. 26, 2013

(54) PYRIMIDIN-4-YL-3, 4-DIHYDRO-2H-PYRROLO [1,2A] PYRAZIN-1-ONE COMPOUNDS

(75) Inventors: Stuart Jones, Dundee (GB); Robert Westwood, Oxon (GB); Mark Thomas, Dundee (GB); Janice McLachlan, Dundee (GB); Kenneth Duncan, Waltham, MA (US); Fred Scaerou, Cambridge (GB); Daniella I. Zheleva, Fife (GB)

(73) Assignee: Cyclacel Limited, London (GB)

( * ) Notice: Subject to any disclaimer, the term of this patent is extended or adjusted under 35 U.S.C. 154(b) by 695 days.

(21) Appl. No.: 12/083,534

(22) PCT Filed: Oct. 9, 2006

(86) PCT No.: PCT/GB2006/003748
§ 371 (c)(1),
(2), (4) Date: Oct. 22, 2009

(87) PCT Pub. No.: WO2007/042784
PCT Pub. Date: Apr. 19, 2007

(65) Prior Publication Data
US 2010/0035870 A1 Feb. 11, 2010

(30) Foreign Application Priority Data
Oct. 14, 2005 (GB) .................................. 0520958.0

(51) Int. Cl.
*A61K 31/4965* (2006.01)
(52) U.S. Cl. ................. 514/255.05; 514/275; 514/252.1; 514/249; 514/248; 514/247; 544/295; 544/242; 544/349; 544/338
(58) Field of Classification Search .......................... None
See application file for complete search history.

(56) References Cited

U.S. PATENT DOCUMENTS

| | | | |
|---|---|---|---|
| 5,958,935 A | 9/1999 | Davis et al. | |
| 6,417,185 B1 | 7/2002 | Goff et al. | |
| 6,531,479 B2 * | 3/2003 | Wang et al. | 514/275 |
| 6,699,854 B2 * | 3/2004 | Wang et al. | 514/183 |
| 7,262,202 B2 * | 8/2007 | Fischer et al. | 514/275 |
| 7,388,015 B2 * | 6/2008 | Wang et al. | 514/275 |
| 7,427,627 B2 * | 9/2008 | Wang et al. | 514/275 |
| 7,432,260 B2 * | 10/2008 | Wang et al. | 514/235.8 |
| 7,897,605 B2 * | 3/2011 | Wang et al. | 514/252.14 |
| 7,902,361 B2 * | 3/2011 | Wang et al. | 544/331 |
| 2002/0019404 A1 | 2/2002 | Wang et al. | |
| 2004/0259894 A1 | 12/2004 | Wang et al. | |
| 2005/0192300 A1 | 9/2005 | Wang et al. | |
| 2005/0282843 A1 | 12/2005 | Wang et al. | |
| 2005/0288307 A1 | 12/2005 | Wang et al. | |
| 2006/0199830 A1 | 9/2006 | Wang et al. | |

(Continued)

FOREIGN PATENT DOCUMENTS

EP 0233461 B1 8/1987
EP 0588762 A1 3/1994

(Continued)

OTHER PUBLICATIONS

"Aurora kinase inhibitors in preclinical and clinical testing" by Cheung et al., Expert Opin. Investig. Drugs 18, 379-98 (2009).*

*Primary Examiner* — Anish Gupta
*Assistant Examiner* — Theodore R West
(74) *Attorney, Agent, or Firm* — Nelson Mullins Riley & Scarborough LLP; Cynthia L. Kanik

(57) ABSTRACT

The present invention relates to compounds of formula (I), or pharmaceutically acceptable salts thereof, wherein Z is $NR^{11}$, NHCO, $NHSO_2$, $NHCH_2$, $CH_2$, $CH_2CH_2$, or CH=CH; X is a hydrocarbyl group optionally substituted by one or more $R^{12}$ groups; $R^{10}$ and $R^{11}$ are each independently H or alkyl; $R^1$-$R^4$ are each independently H or $(CH_2)_m R^{12}$, where m is 0, 1, 2, or 3; each $R^{12}$ is independently $(CH_2)_a R^{16}$, where each $R^{16}$ is independently selected from $O(CH_2)_b R^{13}$, $R^{13}$, $COR^{13}$, $COOR^{13}$, CN, $CONR^{13}R^{14}$, $NR^{13}R^{14}$, $NR^{13}COR^{14}$, $SR^{13}$, $SOR^{13}$, $SO_2R^{13}$, $NR^{13}SO_2R^{14}$, $SO_2OR^{13}$, $SO_2NR^{13}R^{14}$, halogen, $CF_3$, and $NO_2$, and wherein each a is 0, 1, 2, or 3 and b is 0, 1, 2, or 3; $R^{13}$ and $R^{14}$ are each independently H or $(CH_2)_a R^{15}$, where n is 0, 1, 2, or 3; and each $R^{15}$ is independently selected from alkyl, cycloalkyl, heteroaryl, aralkyl, aryl and heterocycloalkyl, each of which may be optionally substituted by one or more substituents selected from halogen, OH, CN, COO-alkyl, aralkyl, $SO_2$-alkyl, $SO_2$-aryl, COOH, CO-alkyl, CO-aryl, $NH_2$, NH-alkyl, $N(alkyl)_2$, $CF_3$, alkyl and alkoxy, wherein said alkyl and alkoxy groups may be further substituted by one or more OH groups. Further aspects of the invention relate to pharmaceutical compositions comprising compounds of formula I, and the use of compounds of formula (I) in the preparation of a medicament for treating a variety of disorders, including proliferative disorders, viral disorders, stroke, etc.

(I)

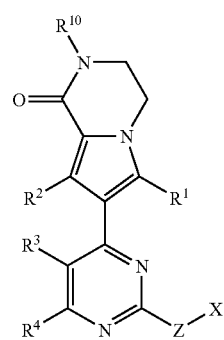

52 Claims, No Drawings

U.S. PATENT DOCUMENTS

| | | |
|---|---|---|
| 2006/0241297 A1 | 10/2006 | Wang et al. |
| 2007/0021419 A1 | 1/2007 | Wang et al. |
| 2007/0021452 A1 | 1/2007 | Wang et al. |
| 2007/0185134 A1 | 8/2007 | Fischer et al. |

FOREIGN PATENT DOCUMENTS

| | | |
|---|---|---|
| WO | WO-95/09852 A1 | 4/1995 |
| WO | WO-97/19065 A1 | 5/1997 |
| WO | WO-00/39101 A1 | 7/2000 |
| WO | 01/60816 A1 | 8/2001 |
| WO | WO-02/46171 A2 | 6/2002 |
| WO | WO-02/066480 A2 | 8/2002 |
| WO | WO-02/096905 A1 | 12/2002 |
| WO | WO-03/029248 A1 | 4/2003 |

\* cited by examiner

PYRIMIDIN-4-YL-3, 4-DIHYDRO-2H-PYRROLO [1,2A] PYRAZIN-1-ONE COMPOUNDS

RELATED APPLICATIONS

The present application is a 35 U.S.C. 371 national stage filing of International Application No. PCT/GB2006/003748, filed Oct. 6, 2006, which claims priority to Great Britain Application No. 0520958.0, filed Oct. 14, 2005. The entire contents of each of these applications are hereby incorporated herein by reference in their entirety.

The present invention relates to substituted pyrimidine derivatives. In particular, the invention relates to 2-anilino-4-(3,4-dihydropyrrolo[1,2-a]pyrazin-1(2B)-one)-pyrimidines and their use in therapy. More specifically, but not exclusively, the invention relates to compounds that are capable of inhibiting one or more protein kinases.

BACKGROUND TO THE INVENTION

In eukaryotes, all biological functions, including DNA replication, cell cycle progression, energy metabolism, and cell growth and differentiation, are regulated through the reversible phosphorylation of proteins. The phosphorylation state of a protein determines not only its function, subcellular distribution, and stability, but also what other proteins or cellular components it associates with. The balance of specific phosphorylation in the proteome as a whole, as well as of individual members in a biochemical pathway, is thus used by organisms as a strategy to maintain homeostasis in response to an ever-changing environment [Cohen, P. *Nat. Rev. Drug Disc.*, 2002, 1, 309]. The enzymes that carry out these phosphorylation and dephosphorylation steps are protein kinases and phosphatases, respectively. Many kinases have gained importance as drug discovery targets in a variety of therapeutic areas [Fischer, P. M. *Curr. Med. Chem.*, 2004, 11, 1563].

The eukaryotic protein kinase family is one of the largest in the human genome, comprising some 500 genes [Manning, G.; Whyte, D. B.; Martinez, R; Hunter, T.; Sudarsanam, S., The protein kinase complement of the human genome, *Science* 2002, 298, 1912-1934; Kostich, M.; English, J.; Madison, V.; Gheyas, F.; Wang, L., et al. Human members of the eukaryotic protein kinase family, *Genome Biology* 2002, 3, Research 0043.0041-0043.0012].

The majority of kinases contain a 250-300 amino acid residue catalytic domain with a conserved core structure. This domain comprises a binding pocket for ATP (less frequently GTP), whose terminal phosphate group the kinase transfers covalently to its macromolecular substrates. The phosphate donor is always bound as a complex with a divalent ion (usually $Mg^{2+}$ or $Mn^{2+}$). Another important function of the catalytic domain is the binding and orientation for phosphotransfer of the macromolecular substrate. The catalytic domains present in most kinases are more or less homologous.

A wide variety of molecules capable of inhibiting protein kinase function through antagonising ATP binding are known in the art [Dancey, J.; Sausville, E. A. Issues and progress with protein kinase inhibitors for cancer treatment, *Nat. Rev. Drug Disc.* 2003, 2, 296-313; Cockerill, G. S.; Lackey, K. E., Small molecule inhibitors of the class 1 receptor tyrosine kinase family. Current Topics in *Medicinal Chemistry* 2002, 2, 1001-1010; Fabbro, D.; Ruetz, S.; Buchdunger, E.; Cowan-Jacob, S. W.; Fendrich, G. et al., Protein kinases as targets for anti-cancer agents: from inhibitors to useful drugs, *Pharmacol. Ther.* 2002, 93, 79-98; Cohen, P., Protein kinases—the major drug targets of the twenty-first century? *Nat. Rev. Drug Disc.* 2002, 1, 309-315; Bridges, A. J., Chemical inhibitors of protein kinases, *Chem. Rev.* 2001, 101(8), 2541-2571].

By way of example, the applicant has previously disclosed 2-anilino-4-heteroaryl-pyrimidine compounds with kinase inhibitory properties, particularly against cyclin-dependent kinases (CDKs) [Wang, S.; Meades, C.; Wood, G.; Osnowski, A.; Fischer, P. M., N-(4-(4-methylthiazol-5-yl)pyrimidin-2-yl)-N-phenylamines as antiproliferative compounds, PCT Intl. Patent Appl. Publ. WO 2003029248, Cyclacel Limited, UK; Wu, S. Y.; McNae, I.; Kontopidis, G.; McClue, S. J.; McInnes, C. et al., Discovery of a Novel Family of CDK Inhibitors with the Program LIDAEUS: Structural Basis for Ligand-Induced Disordering of the Activation Loop, *Structure* 2003, 11, 399410; Fischer, P. M.; Wang, S.; Wood, G., Inhibitors of cyclin dependent kinases as anti-cancer agents, *PCT Intl. Patent Appl. Pubi.* WO 02/079193; Cyclacel Limited, UK; Wang, S.; Fischer, P. M. Anti-cancer compounds, US Patent Appl. Publ. 2002/0019404; Fischer, P. M.; Wang, S., 2-substituted 4-heteroaryl-pyrimidines and their use in the treatment of proliferative disorders, PCTIntl. Patent Appl. Publ. WO 2001072745; Cyclacel Limited, UK].

CDKs are serine/threonine protein kinases that associate with various cyclin subunits. These complexes are important for the regulation of eukaryotic cell cycle progression, but also for the regulation of transcription [Knockaert, M.; Greengard, P.; Meijer, L., Pharmacological inhibitors of cyclin-dependent kinases, *Trends Pharmacol. Sci.* 2002, 23, 417-425; Fischer, P. Ma; Endicott, J.; Meijer, L., Cyclin-dependent kinase inhibitors, *Progress in Cell Cycle Research*; Editions de la Station Biologique de Roscoff: Roscoff, France, 2003; pp 235-248].

The present invention seeks to provide further substituted pyrimidine derivatives. More specifically, the invention relates to compounds that have broad therapeutic applications in the treatment of a number of different diseases and/or that are capable of inhibiting one or more protein kinases.

STATEMENT OF INVENTION

A first aspect of the invention relates to compounds of formula I, or pharmaceutically acceptable salts thereof,

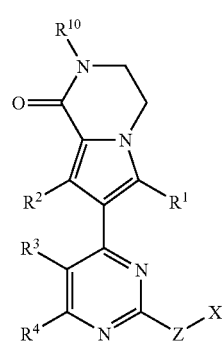

I wherein
Z is $NR^{11}$, NHCO, $NHSO_2$, $NHCH_2$, $CH_2$, $CH_2CH_2$, or CH=CH;
X is a hydrocarbyl group optionally substituted by one or more $R^{12}$ groups;
$R^{10}$ and $R^{11}$ are each independently H or alkyl;
$R^1$-$R^4$ are each independently H or $(CH_2)_m R^{12}$, where m is 0, 1, 2, or 3;

each $R^{12}$ is independently $(CH_2)_a R^{16}$, where each $R^{16}$ is independently selected from $O(CH_2)_b R^{13}$, $R^{13}$, $COR^{13}$, $COOR^{13}$, CN, $CONR^{13}R^{14}$, $NR^{13}R^{14}$, $NR^{13}COR^4$, $SR^{13}$, $SOR^{13}$, $SO_2R^{13}$, $NR^{13}S_2R^{14}$, $SO_2OR^{13}$, $SO_2NR^{13}R^{14}$, halogen, $CF_3$, and $NO_2$, and wherein each a is 0, 1, 2, or 3 and b is 0, 1, 2, or 3;

$R^{13}$ and $R^{14}$ are each independently H or $(CH_2)_n R^{15}$, where n is 0, 1, 2, or 3; and each $R^{15}$ is independently selected from alkyl, cycloalkyl, heteroaryl, aralkyl, aryl and heterocycloalkyl, each of which may be optionally substituted by one or more substituents selected from halogen, OH, CN, COO-alkyl, aralkyl, $SO_2$-alkyl, $SO_2$-aryl, COOH, CO-alkyl, CO-aryl, $NH_2$, NH-alkyl, N(alkyl)$_2$, $CF_3$, alkyl and alkoxy, wherein said alkyl and alkoxy groups may be further substituted by one or more OH groups.

The present invention provides compounds that are capable of inhibiting various protein kinases, including aurora kinase [Carmena, M.; Earnshaw, W. C., *Nat. Rev. Mol. Cell. Biol.*, 2003, 4, 842], FMS-like tyrosine kinase 3 (FLT3) [Stirewalt, D. L.; Radich, J. P., *Nat. Rev. Cancer*, 2003, 3, 650], cyclin-dependent kinases (CDKs) [Fischer, P. M.; Endicott, J.; Meijer, L., *Progr. Cell Cycle Res.*, 2003, 5, 235], and glycogen synthase kinase 3 (GSK3) [Cohen, P.; Goedert, M., *Nat. Rev. Drug Disc.*, 2004, 3, 479].

A second aspect of the invention relates to a pharmaceutical composition comprising a compound of formula I as defined above admixed with a pharmaceutically acceptable diluent, excipient or carrier.

Further aspects of the invention relate to the use of compounds of formula I as defined above in the preparation of a medicament for treating one or more of the following:
a proliferative disorder;
a viral disorder;
a CNS disorder;
a stroke;
a microbial infection;
a fungal disorder;
a parasitic disorder;
an inflammatory disorder;
a cardiovascular disorder.
alopecia; and
diabetes.

Another aspect of the invention relates to the use of compounds of formula I as defined above in an assay for identifying further candidate compounds capable of inhibiting one or more of a cyclin dependent kinase, GSK, aurora kinase, a tyrosine kinase, FMS-like tyrosine kinase-2 (FLT-3) and a PLK enzyme.

Another aspect of the invention relates to compounds of formula I as defined above, or pharmaceutically acceptable salts thereof, for use in medicine.

DETAILED DESCRIPTION

As used herein, the term "hydrocarbyl" refers to a group comprising at least C and H. If the hydrocarbyl group comprises more than one C then those carbons need not necessarily be linked to each other. For example, at least two of the carbons may be linked via a suitable element or group. Thus, the hydrocarbyl group may contain heteroatoms. Suitable heteroatoms will be apparent to those skilled in the art and include, for instance, sulphur, nitrogen, oxygen, phosphorus and silicon. Where the hydrocarbyl group contains one or more heteroatoms, the group may be linked via a carbon atom or via a heteroatom to another group, i.e. the linker atom may be a carbon or a heteroatom. Preferably, the hydrocarbyl group is an aryl, heteroaryl, alkyl, cycloalkyl, aralkyl, heterocycloalkyl, or alkenyl group. More preferably, the hydrocarbyl group is an aryl, heteroaryl, alkyl, cycloalkyl, aralkyl or alkenyl group. The hydrocarbyl group may be optionally substituted by one or more $R^{12}$ groups.

As used herein, the term "alkyl" includes both saturated straight chain and branched alkyl groups which may be substituted (mono- or poly-) or unsubstituted. Preferably, the alkyl group is a $C_{1-20}$ alkyl group, more preferably a $C_{1-15}$, more preferably still a $C_{1-12}$ alkyl group, more preferably still, a $C_{1-6}$ alkyl group, more preferably a $C_{1-3}$ alkyl group. Particularly preferred alkyl groups include, for example, methyl, ethyl, propyl, isopropyl, butyl, isobutyl, tert-butyl, pentyl and hexyl. Suitable substituents include, for example, one or more $R^{12}$ groups. Preferably, the alkyl group is unsubstituted.

As used herein, the term "cycloalkyl" refers to a cyclic alkyl group which may be substituted (mono- or poly-) or unsubstituted. Preferably, the cycloalkyl group is a $C_{3-12}$ cycloalkyl group. Suitable substituents include, for example, one or more $R^{12}$ groups.

As used herein, the term "alkenyl" refers to a group containing one or more carbon-carbon double bonds, which may be branched or unbranched, substituted (mono- or poly-) or unsubstituted. Preferably the alkenyl group is a $C_{2-20}$ alkenyl group, more preferably a $C_{2-15}$ alkenyl group, more preferably still a $C_{2-12}$ alkenyl group, or preferably a $C_{2-6}$ alkenyl group, more preferably a $C_{2-3}$ alkenyl group. Suitable substituents include, for example, one or more $R^{12}$ groups as defined above.

As used herein, the term "aryl" refers to a $C_{6-12}$ aromatic group which may be substituted (mono- or poly-) or unsubstituted. Typical examples include phenyl and naphthyl etc. Suitable substituents include, for example, one or more $R^{12}$ groups.

As used herein, the term "heteroaryl" refers to a $C_{2-12}$ aromatic, substituted (mono- or poly-) or unsubstituted group, which comprises one or more heteroatoms. Preferably, the heteroaryl group is a $C_{4-12}$ aromatic group comprising one or more heteroatoms selected from N, O and S. Suitable heteroaryl groups include pyrrole, pyrazole, pyrimidine, pyrazine, pyridine, quinoline, thiophene, 1,2,3-triazole, 1,2,4-triazole, thiazole, oxazole, iso-thiazole, iso-oxazole, imidazole, furan and the like. Again, suitable substituents include, for example, one or more $R^{12}$ groups.

As used herein, the term "heterocycloalkyl" refers to a cyclic aliphatic group which contains one or more heteroatoms. Preferred heterocycloalkyl groups include piperidinyl, pyrrolidinyl, piperazinyl, thiomorpholinyl and morpholinyl. More preferably, the heterocycloalkyl group is selected from N-piperidinyl, N-pyrrolidinyl, N-piperazinyl, N-thiomorpholinyl and N-morpholinyl.

As used herein, the term "aralkyl" includes, but is not limited to, a group having both aryl and alkyl functionalities. By way of example, the term includes groups in which one of the hydrogen atoms of the alkyl group is replaced by an aryl group, e.g. a phenyl group optionally having one or more substituents such as halo, alkyl, alkoxy, hydroxy, and the like. Typical aralkyl groups include benzyl, phenethyl and the like.

In one preferred embodiment, X is:
(i) a $C_{5-15}$, saturated or unsaturated monocyclic group, or
(ii) a bicyclic or tricyclic group, each of which may be saturated or unsaturated, or a combination thereof, and which may be fused or unfused;
wherein each group optionally contains one or more heteroatoms selected from O, N and S and/or one or more C=O and/or $SO_2$ groups, and is optionally substituted by one or more $R^{12}$ groups.

In one highly preferred embodiment, X optionally contains one, two or three heteroatoms selected from O, N and S and/or optionally contains one C=O group and/or one $SO_2$ group.

In one preferred embodiment, X is a monocyclic group selected from phenyl, 2-pyridynyl, 3-pyridynyl and 4-pyridynyl, each of which may be optionally substituted by one or more $R^{12}$ substituents. More preferably, X is phenyl or 3-pyridynyl, each of which may be optionally substituted by one or more $R^{12}$ substituents.

In one preferred embodiment, X is an unfused group selected from thiomorpholinyl-phenyl, morpholino-phenyl, piperazinyl-phenyl, pyrimidinyl-phenyl, isoxazolyl-phenyl, oxazolyl-phenyl, pyrrolyl-phenyl, triazolyl-phenyl, thiazolyl-phenyl, 2,3-dihydro-imidazothiazolyl-phenyl, 2-oxo-oxazolidinyl-phenyl, [1,2,3]-thiadiazol-4-yl-phenyl and pyrazolyl-phenyl, each of which may be optionally substituted by one or more $R^{12}$ groups.

In a more preferred embodiment, X is an unfused group selected from 4-(2-oxo-oxazolidin-3-yl)-phenyl, 4-pyrazol-1-yl-phenyl, 4-[1,2,3]thiadiazol-4-yl-phenyl, 4-thiomorpholinyl-phenyl, 4-[1,2,4]-triazol-1-yl-phenyl, thiazolyl-phenyl, 4H-[1,2,4]-triazol-3-yl-phenyl, 2,3-dihydro-imidazo[2,1-b]thiazol-6-yl-phenyl, 4-morpholin-4-yl-phenyl, 4-oxazol-5-yl-phenyl, 4-isoxazol-5-yl-phenyl, 4-pyrrol-1-yl-phenyl, 3-oxazol-5-yl-phenyl, 4-piperazin-1-yl-phenyl, pyrimidin-4-yl-phenyl and pyrimidin-5-yl-phenyl, each of which may be optionally substituted by one or more $R^{12}$ groups.

In one preferred embodiment, X is an unfused group selected from the following:

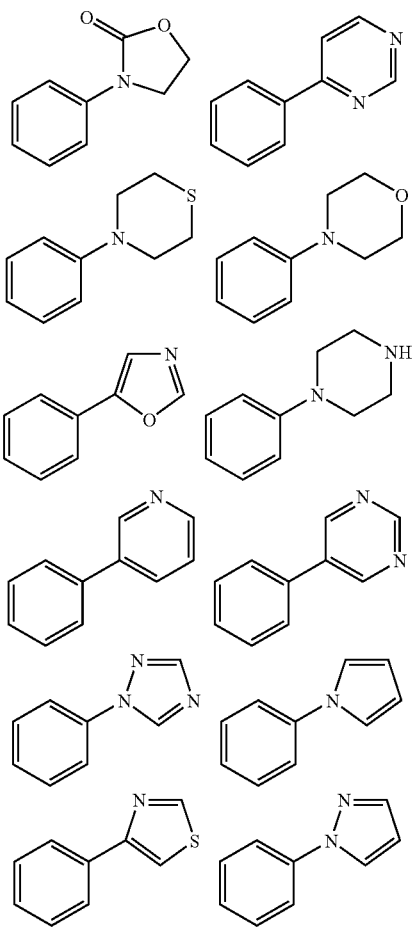

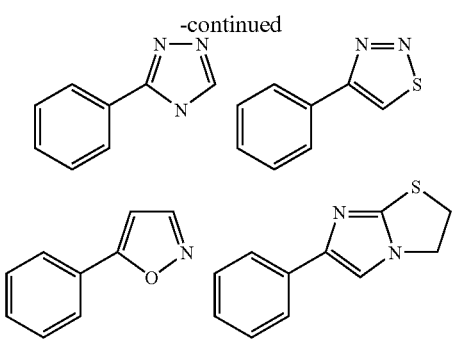

each of which may be optionally substituted by one or more $R^{12}$ groups.

In another preferred embodiment, X is a fused bicyclic group selected from indazolyl, benzo-oxazinonyl, benzothiophenyl, benzodioxolyl, benzodioxinyl, indolyl, 3,4-dihydro-2H-benzodioxepinyl and 2,2-dioxo-2,3-dihydro-1H-2-benzothiophenyl, each of which may be optionally substituted by one or more $R^{12}$ groups.

In another more preferred embodiment, X is a fused bicyclic group selected from 1H-indazol-6-yl, 2,2-dioxo-2,3-dihydro-1H-2-benzo[c]thiophen-5-ylamino, 3,4-dihydro-2H-benzo[b][1,4]dioxepin-7-yl, 1H-indol-5-yl, 4H-benzo[1,3]dioxin-6-yl, benzo-[1,3]dioxol-5-yl, 5-benzo[b]thiophenyl and 4H-benzo[1,4]oxazin-3-onyl, each of which may be optionally substituted by one or more $R^{12}$ groups.

In another preferred embodiment, X is a fused bicyclic group selected from the following:

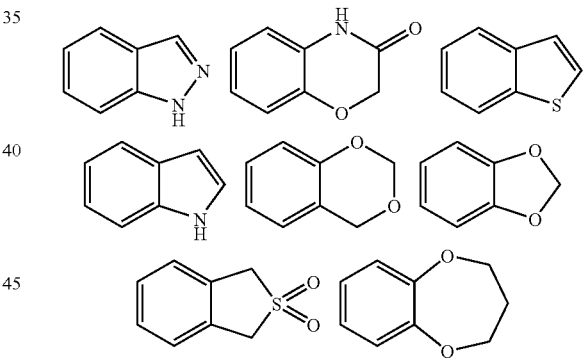

each of which may be optionally substituted by one or more $R^{12}$ groups.

Preferably, X is optionally substituted by one or two $R^{12}$ groups.

In one preferred embodiment, each $R^{12}$ is independently selected from $O(CH_2)_bR^{13}$, $R^{13}$, $(CH_2)_aCOR^{13}$, $(CH_2)_aCOOR^{13}$, $COOR^{13}$, CN, $(CH_2)_aCONR^{13}R^{14}$, $NR^{13}R^{14}$, $NR^{13}COR^{14}$, $SR^{13}$, $SOR^{13}$, $SO_2R^{13}$, $NR^{13}SO_2R^{14}$, $SO_2OR^{13}$, $SO_2NR^{13}R^{14}$, halogen, $CF_3$, and $NO_2$. Preferably, a and b are each independently 0, 1 or 2.

In one preferred embodiment, each $R^{12}$ is independently selected from O-alkyl, alkyl, halogen, $(CH_2)_a$—COOH, $NHSO_2$-alkyl, $NO_2$, CN, NHCO-alkyl, NHCO-aryl, CO-alkyl, CO-aryl, COO-alkyl, N(alkyl)$_2$, NH-alkyl, $SO_2$-alkyl, OH, $SO_2$-heterocycloalkyl, $SO_2$—NH-alkyl, $SO_2$—N(alkyl)$_2$, $(CH_2)_a$—CO-heterocycloalkyl, $(CH_2)_a$—CONH-alkyl, $(CH_2)_a$—CONH$_2$, $(CH_2)_a$—CON(alkyl)$_2$, $O(CH_2)_b$-aryl, $(CH_2)_a$-heteroaryl and $O(CH_2)_b$-heterocycloalkyl, wherein said alkyl, aryl, heteroaryl and heterocycloalkyl groups may be further substituted by one or more substituents selected from CN, halogen, alkyl and CO-alkyl. Preferably, a and b are each independently 0, 1 or 2.

In an even more preferred embodiment, each $R^{12}$ is independently selected from OMe, Me, Cl, Br, F, $CH_2COOH$, $CH_2CH_2COOH$, $OCH_2COOH$, $CH(Me)COOH$, COOH, $NHSO_2Me$, $NO_2$, CN, $CH_2CN$, $OCH_2Ph$, NHCOMe, NHCO-aryl, COMe, COPh, COOEt, $NMe_2$, $NEt_2$, NHMe, $SO_2Me$, $SO_2Pr$, OH, $SO_2$—NH—$(CH_2)_3NEt_2$, $SO_2$—NH—$(CH_2)_2NEt_2$, $SO_2$—NH—$(CH_2)_2NMe_2$, $SO_2$—N(Me)-$(CH_2)_3NMe_2$, $SO_2$—NH—$(CH_2)_2OMe$, $SO_2$-pyrrolidine, $SO_2$-piperidine, $CF_3$, $SO_2$—NHPr, $SO_2$-moxpholine, $SO_2$—NHMe, $(CH_2)_2$—CO-morphiline, $CH_2CO$-morphiline, $CH_2CONHMe$, $CH_2CONH(CH_2)_2OMe$, $CH_2CH_2CONH(CH_2)_2OMe$, $CH_2CONH(CH_2)_2NMe_2$, $CH_2CONH(CH_2)_3NMe_2$, $CH_2CH_2CON(Me)(CH_2)_3NMe_2$, $CH_2CH_2CON(Me)(CH_2)_2NMe_2$, $CH_2CONH_2$, $CH_2CON(Me)_2$, $CH_2CH_2CON(Me)_2$, $CH_2CH_2CONHMe$, $CH_2CH_2CONH_2$, $CH_2$-(4-pyridine), $O(CH_2)_2$-morpholine, O-4-methylphenyl), CO-(4-methylpiperazine), $CH_2CO$-(4-methylpiperazine), $CH_2CH_2CO$-(4-methylpiperazine), $SO_2$-(4-methylpiperazine), $CH_2CO$-(4-acetylpiperazine) and $CH_2CH_2CO$-(4-acetylpiperazine).

In one preferred embodiment of the invention $R^{10}$ is H or Me.

In one preferred embodiment, Z is $NR^{11}$. Preferably, $R^{11}$ is H, Me or Et.

In a more preferred embodiment, Z is NH.

In one preferred embodiment of the invention, $R^3$ and $R^4$ are both H.

In one preferred embodiment of the invention, said compound is of formula Ia as defined below, and $R^{5-9}$ are each independently H or $R^{12}$ as defined above.

In one preferred aspect of the invention relates to a compound of formula Ib, or a pharmaceutically acceptable salt thereof,

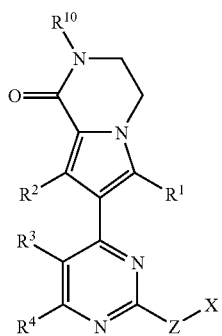

Ib wherein
Z is $NR^{11}$, NHCO, $NHSO_2$, $NHCH_2$, $CH_2$, $CH_2CH_2$, or CH=CH;
X is a hydrocarbyl group optionally substituted by one or more $R^{12}$ groups;
$R^{10}$ and $R^{11}$ are each independently H or alkyl;
$R^1$-$R^4$ are each independently H or $(CH_2)_mR^{12}$, where m is 0, 1, 2, or 3;
each $R^{12}$ is independently selected from $OR^{13}$, $R^{13}$, $COR^{13}$, $COOR^3$, CN, $CONR^{13}R^{14}$, $NR^{13}R^{14}$, $NR^{13}COR^{14}$, $SR^{13}$, $SOR^{13}$, $SO_2R^{13}$, $NR^{13}SO_2R^4$, $SO_2OR^{13}$, $SO_2NR^{13}R^{14}$, halogen, $CF_3$, and $NO_2$; and $R^{13}$ and $R^{14}$ are each independently H or $(CH_2)_nR^{15}$, where n is 0, 1, 2, or 3; and
each $R^{15}$ is independently selected from alkyl, cycloalkyl, heteroaryl, aralkyl, aryl and heterocycloalkyl, each of which may be optionally substituted by one or more substituents selected from halogen, OH, CN, COO-alkyl, aralkyl, $SO_2$-alkyl, $SO_2$-aryl, COOH, CO-alkyl, CO-aryl, $NH_2$, NH-alkyl, $N(alkyl)_2$, $CF_3$, alkyl and alkoxy, wherein said alkyl and alkoxy groups may be filter substituted by one or more OH groups.

In one preferred embodiment of the invention, X is a phenyl or pyridinyl group, each of which may be optionally substituted by one or more $R^{12}$ groups. More preferably, X is a phenyl, 2-pyridinyl or 3-pyridinyl group, each of which may be optionally substituted by one or more $R^{12}$ groups.

In one highly preferred embodiment, the compound of the invention is of formula Ia, or a pharmaceutically acceptable salt thereof,

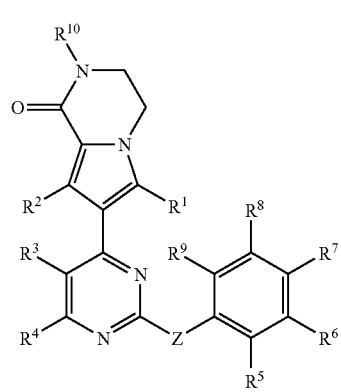

Ia wherein
Z is $NR^{11}$, NHCO, $NHSO_2$, $NHCH_2$, $CH_2$, $CH_2CH_2$, or CH=CH;
$R^{10}$ and $R^{11}$ are each independently H or alkyl;
$R^1$-$R^9$ are each independently H or $(CH_2)_mR^{12}$ where m is 0, 1, 2, or 3;
each $R^{12}$ is independently selected from $OR^{13}$, $R^{13}$, $COR^{13}$, $COOR^{13}$, CN, $CONR^{13}R^{14}$, $NR^{13}R^{14}$, $NR^{13}COR^{14}$, $SR^{13}$, $SOR^{13}$, $SO_2R^{13}$, $NR^{13}SO_2R^{14}$, $SO_2OR^{13}$, $SO_2NR^{13}R^{14}$, halogen, $CF_3$ and $NO_2$; and
$R^{13}$ and $R^{14}$ are each independently H or $(CH_2)_nR^5$, where n is 0, 1, 2, or 3; and
each $R^{15}$ is independently selected from alkyl, cycloalkyl, heteroaryl, aralkyl, aryl and heterocycloalkyl, each of which may be optionally substituted by one or more substituents selected from halogen, OH, CN, COO-alkyl, aralkyl, $SO_2$-alkyl, $SO_2$-aryl, COOH, CO-alkyl, CO-aryl, $NH_2$, NH-alkyl, N(alkyl), $CF_3$, alkyl and alkoxy, wherein said alkyl and alkoxy groups may be further substituted by one or more OH groups.

In another preferred embodiment, said compound is of formula Ia as described above, but each $R^{12}$ is independently $(CH_2)_aR^{16}$, where each $R^{16}$ is independently selected from $O(CH_2)_bR^{13}$, $R^{13}$, $COR^{13}$, $COOR^{13}$, CN, $CONR^{13}R^{14}$, $NR^{13}R^{14}$, $NR^{13}COR^{14}$, $SR^{13}$, $SOR^{13}$, $SO_2R^{13}$, $NR^{13}SO_2R^{14}$, $SO_2OR^{13}$, $SO_2NR^{13}R^{14}$, halogen, $CF_3$, and $NO_2$, and wherein each a is 0, 1, 2, or 3 and b is 0, 1, 2, or 3.

In one preferred embodiment of the invention, each $R^{15}$ is independently selected from ethyl, ethyl, isopropyl, n-butyl, isobutyl, t-butyl, cyclopropyl, cyclobutyl, cyclopentyl, cyclohexyl, phenyl, pyridinyl, pyrrolidinyl, pyrrolyl, morpholinyl, piperazinyl, piperidinyl, triazolyl, tetrazolyl and thiazolyl.

In one preferred embodiment of the invention, each $R^{12}$ is independently selected from OH, OMe, COMe, CHO, $CO_2Me$, COOH, CN, $CONH_2$, NHMe, $NH_2$, $NMe_2$, SH, SMe, SOMe, $SO_2Me$, $SO_2NHMe$, $SO_2NH_2$, Cl, Br, F, I, $CF_3$, $NO_2$, N-morpholinyl, N-pyrrolidinyl and N-piperazinyl.

In one particularly preferred embodiment of the invention, $R^5$, $R^6$, $R^7$, $R^8$ and $R^9$ are each independently selected from H and $(CH_2)_m R^{12}$;
each $R^{12}$ is independently selected from $R^{13}$, $NR^{13}COR^{14}$, $NR^{13}R^{14}$, $SO_2R^{13}$, $NR^{13}SO_2R^{14}$, $OR^{13}$, alkyl, $NO_2$, $CF_3$, alkoxy, halogen;
$R^{13}$ and $R^{14}$ are each independently H or $(CH_2)_n R^{15}$; and
each $R^{15}$ is independently selected from alkyl, heteroaryl, aryl and heterocycloalkyl, each of which may be optionally substituted by one or more substituents selected from halogen, OH, CN, COO-alkyl, COOH, CO-alkyl, aralkyl, $SO_2$-alkyl, $SO_2$-aryl, CO-aryl, alkyl, alkoxy, $NH_2$, NH-alkyl, $N(alkyl)_2$ and $CF_3$.

Even more preferably,
$R^5$, $R^6$, $R^7$, $R^8$ and $R^9$ are each independently selected from H and $R^{12}$;
each $R^{12}$ is independently selected from $R^{13}$, $NHCOR^{14}$, $NR^{13}R^{14}$; $SO_2R^{13}$, $NHSO_2R^{14}$, $OR^{13}$, alkyl, $NO_2$, $CF_3$, alkoxy, halogen;
$R^{13}$ and $R^{14}$ are each independently H or $R^{15}$; and
each $R^{15}$ is independently selected from alkyl, aryl and heterocycloalkyl, each of which may be optionally substituted by one or more substituents selected from halogen, OH, CO-alkyl, aralkyl, $SO_2$-alkyl, $SO_2$-aryl, CO-aryl, alkyl, alkoxy, $NH_2$, NH-alkyl and $N(alkyl)_2$.

In an even more preferred embodiment, $R^5$, $R^6$, $R^7$, $R^8$ and $R^9$ are each independently selected from H, Me, $NO_2$, $CF_3$, OMe, F, N-morpholinyl, N-piperazinyl and N-piperidinyl, said N-morpholinyl, N-piperazinyl and N-piperidinyl groups each being independently optionally substituted by one or more substituents selected from halogen, OH, CN, COOMe, COOH, COMe, CO-phenyl, Me, OMe, $NH_2$, NH-Me, $NMe_2$ and $CF_3$.

In one preferred embodiment of the invention,
$R^5$, $R^8$ and $R^9$ are all H; and
$R^6$ and $R^7$ are each independently H or $(CH_2)_m R^2$, where $R^{12}$ is as defined above.

In a more preferred embodiment of the invention,
$R^5$, $R^8$ and $R^9$ are all H; and
$R^6$ and $R^7$ are each independently H or $R^{12}$ as defined above.

Even more preferably,
$R^5$, $R^8$ and $R^9$ are all H; and
$R^6$ and $R^7$ are each independently selected from H, alkyl, $NO_2$, $CF_3$, alkoxy, halogen and heterocycloalkyl, said heterocycloalkyl being optionally substituted by one or more substituents selected from halogen, OH, CN, COO-alkyl, COOH, CO-alkyl, CO-aryl, alkyl, alkoxy, $NH_2$, NH-alkyl, $N(alkyl)_2$ and $CF_3$.

More preferably still,
$R^5$, $R^8$ and $R^9$ are all H; and
$R^6$ and $R^7$ are each independently selected from H, Me, $NO_2$, $CF_3$, OMe, F and N-morpholinyl, N-piperazinyl and N-piperidinyl, said N-morpholinyl, N-piperazinyl and N-piperadinyl groups each being independently optionally substituted by one or more substituents selected from halogen, OH, CN, COO-Me, COOH, CO-Me, CO-phenyl, Me, OMe, $NH_2$, NH-Me, $NMe_2$ and $CF_3$.

In one preferred embodiment of the invention, $R^1$ and $R^2$ are each independently selected from H, CN, $NO_2$, alkyl, $CONR^{13}R^{14}$, $NR^{13}R^{14}$, $NHCOR^{13}OR^{13}$, $R^{13}$ and $NR^{13}SO_2R^{14}$.

In a more preferred embodiment of the invention, $R^1$ and $R^2$ are each independently selected from H, CN, $NO_2$, alkyl, $NR^{13}R^{14}$, $NR^{13}COR^{14}$ and $OR^{13}$, where $R^{13}$ and $R^{14}$ are each independently H or alkyl.

In an even more preferred embodiment of the invention, $R^1$ and $R^2$ are each independently alkyl.

More preferably still, $R^1$ and $R^2$ are both methyl.

In one preferred embodiment, the compound is selected from the following:

6,8-Dimethyl-7-[2-(4-morpholinyl-phenylamino)-pyrimidin-4-yl]-3,4-dihydro-2H-pyrrolo[1,2-a]pyrazin-1-one [I-2];

7-[2-(4-Fluoro-phenylamino)-pyrimidin-1-yl]6,8-dimethyl-3,4-dihydro-2H-pyrrolo[1,2-a]pyrazin-1-one [I-1];

7-[2-(3-Methoxy-4-morpholinyl-phenylamino)-pyrimidin-4-yl]-6,8-dimethyl-3,4-dihydro-2H-pyrrolo[1,2-a]pyrazin-1-one [I.3];

7-[2-(4-Methoxy-phenylamino)-pyrimidin-4-yl]-6,9-dimethyl-3,4-dihydro-2H-pyrrolo[1,2-a]pyrazin-1-one [I-4];

6,8-Dimethyl-7-[2-(3-nitro-phenylamino)-pyrimidin-4-yl]-3,4-dihydro-2H-pyrrolo[1,2-a]pyrazin-1-one [I-5]

7-[2-(4-Dimethylamino-phenylamino)-pyrimidin-4-yl]-6,8-dimethyl-3,4-dihydro-2H-pyrrolo[1,2-a]pyrazin-1-one [I-6];

7-{2-[4-(4Acetyl-piperazin-1-yl)-phenylamino]-pyrimidin-4-yl}-6,8-dimethyl-3,4-dihydro-2H-pyrrolo[1,2-a]pyrazin-1-one [I-7]

7-{2-[4-(4-Acetyl-piperazin-1-yl)-3-methyl-phenylamino]-pyrimidin-4-yl}6,8-dimethyl-3,4-dihydro-2H-pyrrolo[1,2-a]pyrazin-1-one [I-8];

7-{2-[4-(4-Acetyl-piperazin-1-yl)-3-methoxy-phenylamino]-pyrimidin-4-yl}-6,8-dimethyl-3,4-dihydro-2H-pyrrolo[1,2-a]pyrazin-1-one [I-9]

7-{2-[4-((2R,6S)-2,6-Dimethyl-morpholin-4-yl)-phenylamino]-pyrimidin-4-yl}-6,8-dimethyl-3,4-dihydro-2H-pyrrolo[1,2-a]pyrazin-1-one [I-10];

7-[2-(1H-Indazol-6-ylamino)-pyrimidin-4-yl]-6,8-dimethyl-3,4-dihydro-2H-pyrrolo[1,2-a]pyrazin-1-one [I-11];

7-[4-(6,8-Dimethyl-1-oxo-1,2,3,4-tetrahydro-pyrrolo[1,2-a]pyrazin-7-yl)-pyrimidin-2-ylamino]-4H-benzo[1,4]oxazin-3-one [I-12]

7-[2-(4-Diethylamino-phenylamino)-pyrimidin-4-yl]-6,8-dimethyl-3,4-dihydro-2H-pyrrolo[1,2-a]pyrazin-1-one [I-13]

6,8-Dimethyl-7-[2-(6-morpholin-4-yl-pyridin-3-ylamino)-pyrimidin-4-yl]-3,4-dihydro-2H-pyrrolo[1,2-a]pyrazin-1-one [I-13a];

7-[2-(6-Methoxy-pyridin-3-ylamino)-pyrimidin-4-yl]-6,8-dimethyl-3,4-dihydro-2H-pyrrolo[1,2-a]pyrazin-1-one [I-13b];

7-[2-(4-Bromo-phenylamino)-pyrimidin-4-yl]-6,8-dimethyl-3,4-hydro-2H-pyrrolo[1,2-a]pyrazin-1-one [I-14];

7-{2-[3-(2-Hydroxy-ethanesulfonyl)-phenylamino]-pyrimidin-4-yl}-6,8-dimethyl-3,4-dihydro-2H-pyrrolo[1,2-a]pyrazin-1-one [I-15];

5-[4-(6,8-Dimethyl-1-oxo-1,2,3,4-tetrahydro-pyrrolo[1,2-a]pyrazin-7-yl)-pyrimidin-2-ylamino]-benzo[b]thiophene-2-carboxylic acid [I-16];

7-[2-(4-Hydroxy-phenylamino)-pyrimidin-4-yl]-6,8-dimethyl-3,4-dihydro-2H-pyrrolo-[1,2-a]pyrazin-1-one [I-17];

4-[4-(6,8-Dimethyl-1-oxo-1,2,3,4-tetrahydro-pyrrolo[1,2-a]pyrazin-7-yl)-pyrimidin-2-ylamino]-N-isopropyl-2-methoxy-benzenesulfonamide [I-18];

4-[4-(6,8-Dimethyl-1-oxo-1,2,3,4-tetrahydro-pyrrolo[1,2-a]pyrazin-7-yl)pyrimidin-2-ylamino]-N-isopropyl-benzenesulfonamide [I-19];

N-{4-[4-(6,8-Dimethyl-1-oxo-1,2,3,4-tetrahydro-pyrrolo[(1,2-a]pyrazin-7-yl)-pyrimidin-2-ylamino]-phenyl}-methanesulfonamide [I-20];

N-(3-Diethylamino-propyl)-4-[4-(6,8-dimethyl-1-oxo-1,2,3,4-tetrahydro-pyrrolo[1,2-a]pyrazin-7-yl)-pyrimidin-2-ylamino]-2-methyl-benzenesulfonamide [I-21];

7-{2-[3-Methoxy-4-(piperidine-1-sulfonyl)-phenylamino]-pyrimidin-4-yl}-6,8-dimethyl-3,4-dihydro-2H-pyrrolo[1,2-a]pyrazin-1-one [I-22];

N-(2-Dimethylamino-ethyl)-4-[4-(6,8-dimethyl-1-oxo-1,2,3,4-tetrahydro-pyrrolo[1,2-a]pyrazin-7-yl)-pyrimidin-2-ylamino]-2-methoxy-benzenesulfonamide [I-23];

7-{2-[3-Methoxy-4-(4-methyl-piperazine-1-sulfonyl)-phenylamino]-pyrimidin-4-yl}-6,8-dimethyl-3,4-dihydro-2H-pyrrolo[1,2-a]pyrazin-1-one [I-24];

[4-(6,8-Dimethyl-1-oxo-1,2,3,4-tetrahydro-pyrrolo[1,2-a]pyrazin-7-yl)-pyrimidin-2-ylamino]-benzoic acid [I-25];

4-[4-(6,8-Dimethyl-1-oxo-1,2,3,4-tetrahydro-pyrrolo[1,2-a]pyrazin-7-yl)-pyrimidin-2-ylamino]-benzoic acid [I-26];

4-[4-(6,8-Dimethyl-1-oxo-1,2,3,4-tetrahydro-pyrrolo[1,2-a]pyrazin-7-yl)-pyrimidin-2-ylamino]-3-methoxy-benzoic acid [I-27];

7-[2-(3-Hydroxy-4-methoxy-phenylamino)pyrimidin-4-yl]-6,8-dimethyl-3,4-dihydro-2H-pyrrolo[1,2-a]pyrazin-1-one [I-28];

7-[2-Benzo[1,3]dioxol-5-ylamino)-pyrimidin-4-yl]-6,8-dimethyl-3,4-dihydro-2H-pyrrolo[1,2-a]pyrazin-1-one [I-29];

6,8-Dimethyl-7-[2-(3-trifluoromethoxy-phenylamino)pyrimidin-4-yl]-3,4-dihydro-2H-pyrrolo[1,2-a]pyrazin-1-one [I-30];

7-[2-(3-Hydroxy-phenylamino)-pyrimidin-4-yl]-6,8-dimethyl-3,4-dihydro-2H-pyrrolo[1,2-a]pyrazin-1-one [I-31];

7-[2-(3-Methanesulfonyl-phenylamino)-pyrimidin-4-yl]-6,8-dimethyl-3,4-dihydro-2H-pyrrolo[1,2-a]pyrazin-1-one [I-32];

7-[2-(4-Methanesulfonyl-phenylamino)-pyrimidin-4-yl]-6,8-dimethyl-3,4-dihydro-2H-pyrrolo[1,2-a]pyrazin-1-one [I-33];

3-{3-[4-(6,8-Dimethyl-1-oxo-1,2,3,4-tetrahydro-pyrrolo[1,2-a]pyrazin-7-yl)-pyrimidin-2-ylamino]-phenyl}-propionic acid [I-34];

8-Dimethyl-7-{2-[3-(morpholine-4-sulfonyl)-phenylamino]-pyrimidin-4-yl}-3,4-dihydro-2H-pyrrolo[1,2-a]pyrazin-1-one [I-35];

66,8-Dimethyl-7-{2-[4-methyl-3-(morpholine-4-sulfonyl)-phenylamino]-pyrimidin-4-yl}-3,4-dihydro-2H-pyrrolo[1,2-a]pyrazin-1-one [I-36];

6,8-Dimethyl-7-[2-(4-thiomorpholin-4-yl-phenylamino)-pyrimidin-4-yl]-3,4-dihydro-2H-pyrrolo[1,2-a]pyrazin-1-one [I-37];

4-[4-(6,8-Dimethyl-1-oxo-1,2,3,4-tetrahydro-pyrrolo[1,2-a]pyrazin-7-yl)-pyrimidin-2-ylamino]-N-(2-methoxy-ethyl)-benzenesulfonamide [I-38];

6,8-Dimethyl-7-(2-p-tolylamino-pyrimidin-4-yl)-3,4-dihydro-2H-pyrrolo[1,2-a]pyrazin-1-one [I-39];

2-{4-[4-(6,8-Dimethyl-1-oxo-1,2,3,4-tetrahydro-pyrrolo[1,2-a]pyrazin-7-yl)-pyrimidin-2-ylamino]-phenyl}-propionic acid [I-40];

{3-[4-(6,8-Dimethyl-1-oxo-1,2,3,4-tetrahydro-pyrrolo[1,2-a]pyrazin-7-yl)-pyrimidin-2-ylamino]-phenoxy}-acetic acid [I-41];

N-{3-[4-(6,8-Dimethyl-1-oxo-1,2,3,4-tetrahydro-pyrrolo[1,2-a]pyrazin-7-yl)-pyrimidin-2-ylamino]-phenyl}-methanesulfonamide [I-42];

4-[4-(6,8-Dimethyl-1-oxo-1,2,3,4-tetrahydro-pyrrolo[1,2-a]pyrazin-7-yl)-pyrimidin-2-ylamino]-2-methoxy-N-methyl-benzenesulfonamide [I-43];

6,8-Dimethyl-7-{2-[4-(2-oxo-oxazolidin-3-yl)-phenylamino]-pyrimidin-4-yl}-3,4-dihydro-2H-pyrrolo[1,2-a]pyrazin-1-one [I-44];

7-[2-4H-Benzo[1,3]dioxin-6-ylamino)-pyrimidin-4-yl]-6,8-dimethyl-3,4-dihydro-2H-pyrrolo[1,2-a]pyrazin-1-one [I-45];

6,8-Dimethyl-7-{2-[3-(2-methyl-pyrimidin-4-yl)-phenylamino]-pyrimidin-4-yl}-3,4-dihydro-2H-pyrrolo[1,2-a]pyrazin-1-one [I-46];

N-{2-Chloro-4-[4-(6,8-dimethyl-1-oxo-1,2,3,4-tetrahydro-pyrrolo[1,2-a]pyrazin-7-yl)-pyrimidin-2-ylamino]-phenyl}-acetamide [I-47];

6,8-Dimethyl-7-[2-(2-methyl-1H-indol-5-ylamino)-pyrimidin-4-yl]-3,4-dihydro-2H-pyrrolo[1,2-a]pyrazin-1-one [I-48];

6,8-Dimethyl-7-[2-(3-oxazol-5-yl-phenylamino)-pyrimidin-4-yl]-3,4-dihydro-2H-pyrrolo[1,2-a]pyrazin-1-one [I-49];

6,8-Dimethyl-7-{2-[4-(morpholine 4-sulfonyl)-phenylamino]-pyrimidin-4-yl}-3,4-dihydro-2H-pyrrolo[1,2-a]pyrazin-1-one [I-50];

6,8-Dimethyl-7-{2-[4-(2-morpholin-4-yl-ethoxy)-phenylamino]-pyrimidin-4-yl}-3,4-dihydro-2H-pyrrolo[1,2-a]pyrazin-1-one [I-51];

6,8-Dimethyl-7-[2-(4-oxazol-5-yl-phenylamino)-pyrimidin-4-yl]-3,4-dihydro-2H-pyrrolo[1,2-a]pyrazin-1-one [I-52];

6,8-Dimethyl-7-[2-(3-pyrimidin-5-yl-phenylamino)-pyrimidin-4-yl]-3,4-dihydro-2H-pyrrolo[1,2-a]pyrazin-1-one [I-53];

6,8-Dimethyl-7-[2-(4-pyridin-4-ylmethyl-phenylamino)-pyrimidin-4-yl]-3,4-dihydro-2H-pyrrolo[1,2-a]pyrazin-1-one [I-54];

6,8-Dimethyl-7-{2-[4-(pyrrolidine-1-sulfonyl)phenylamino]-pyrimidin-4-yl}-3,4-dihydro-2H-pyrrolo[1,2-a]pyrazin-1-one [I-55];

6,8-Dimethyl-7-{2-[4-piperidine-1-sulfonyl)-phenylamino]-pyrimidin-4-yl}-3,4-dihydro-2H-pyrrolo[1,2-a]pyrazin-1-one [I-56];

7-[2-(4-Benzyloxy-phenylamino)-pyrimidin-4-yl]-6,8-ethyl-3,4-dihydro-2H-pyrrolo[1,2-a]pyrazin-1-one [I-57];

7-[2-(3-Benzoyl-phenylamino)-pyrimidin-4-yl]-6,8-dimethyl-3,4-dihydro-2H-pyrrolo[1,2-a]pyrazin-1-one [I-58];

N-{3-[4-(6,8-Dimethyl-1-oxo-1,2,3,4-tetrahydro-pyrrolo[1,2-a]pyrazin-7-yl)-pyrimidin-2-ylamino]-phenyl}-acetamide [I-59];

6,8-Dimethyl-7-[2-(4-[1,2,3]thiadiazol-4-yl-phenylamino)-pyrimidin-4-yl]-3,4-dihydro-2H-pyrrolo[1,2-a]pyrazin-1-one [I-60];

6,8-Dimethyl-7-[2-(4-trifluoromethoxy-phenylamino)pyrimidin-4-yl]-3,4-dihydro-2H-pyrrolo[1,2-a]pyrazin-1-one [I-61];

7-[2-(3,4-Dihydro-2H-benzo[b][1,4]dioxepin-7-ylamino)-pyrimidin-4-yl]-6,8-dimethyl-3,4-dihydro-2H-pyrrolo[1,2-a]pyrazin-1-one [I-62];

7-[2-(2,2-Dioxo-2,3-dihydro-1H-2-benzo[c]thiophen-5-ylamino)-pyrimidin-4-yl]-6,8-dimethyl-3,4-dihydro-2H-pyrrolo[1,2-a]pyrazin-1-one [I-63];

7-[2-(3-Chlorofluoro-phenylamino)-pyrimidin-4-yl]-6,8-dimethyl-3,4-dihydro-2H-pyrrolo[1,2-a]pyrazin-1-one [I-64];

7-[2-(2-Fluoro-phenylamino)-pyrimidin-yl]-6,8-dimethyl-3,4-dihydro-2H-pyrrolo[1,2-a]pyrazin-1-one [I-65];

7-[2-(2,4-Difluoro-phenylamino)-pyrimidin-4-yl]-6,8-dimethyl-3,4-dihydro-2H-pyrrolo[1,2-a]pyrazin-1-one [I-66];

7-[2-(3-Chloro-4-methoxy-phenylamino)-pyrimidin-4-yl]-6,8-dimethyl-3,4-dihydro-2H-pyrrolo[1,2-a]pyrazin-1-one [I-67];

6,8-Dimethyl-7-[2-(4-trifluoromethyl-phenylamino)-pyrimidin-4-yl]-3,4-dihydro-2H-pyrrolo[1,2-a]pyrazin-1-one [I-68];

7-[2-(3-Chloro-phenylamino)-pyrimidin-4-yl]-6,8-dimethyl-3,4-dihydro-2H-pyrrolo[1,2-a]pyrazin-1-one [I-69];

{4-[4-(6,8-Dimethyl-1-oxo-1,2,3,4-tetrahydro-pyrrolo[1,2-a]pyrazin-7-yl)pyrimidin-2-ylamino]-phenyl}-acetic acid [I-70];

6,8-Dimethyl-7-{2-[4-(2-methyl-thiazol-4-yl)-phenylamino]-pyrimidin-4-yl}-3,4-dihydro-2H-pyrrolo[1,2-a]pyrazin-1-one [I-71];

6,8-Dimethyl-7-[2-(4-pyrazol-1-yl-phenylamino)-pyrimidin-4-yl]-3,4-dihydro-2H-pyrrolo[1,2-a]pyrazin-1-one [I-72];

6,8-Dimethyl-7-[2-(4-[1,2,4]triazol-1-yl-phenylamino)-pyrimidin-4-yl]-3,4-dihydro-2H-pyrrolo[1,2-a]pyrazin-1-one [I-73];

6,8-Dimethyl-7-[2-(4-pyrrol-1-yl-phenylamino)-pyrimidin-4-yl]-3,4-dihydro-2H-pyrrolo[1,2-a]pyrazin-1-one [I-74];

7-{2-[4-(2,3-Dihydro-imidazo[2,1-b]thiazol-6-yl)-phenylamino]-pyrimidin-4-yl}-6,8-dimethyl-3,4-dihydro-2H-pyrrolo[1,2-a]pyrazin-1-one [I-75];

7-[2-(3-Methoxy-4-methylamino-phenylamino)-pyrimidin-4-yl]-6,8-dimethyl-3,4-dihydro-2H-pyrrolo[1,2-a]pyrazin-1-one [I-76];

4-[4-(6,8-Dimethyl-1-oxo-1,2,3,4-tetrahydro-pyrrolo[1,2-a]pyrazin-7-yl)-pyrimidin-2-ylamino]-benzonitrile [I-77];

6,8-Dimethyl-7-[2-(4-pyridin-3-yl-phenylamino)-pyrimidin-4-yl]-3,4-dihydro-2H-pyrrolo[1,2-a]pyrazin-1-one [I-78];

6,8-Dimethyl-7-{2-[4-(4-methyl-4H-[1,2,4]triazol-3-yl)-phenylamino]-pyrimidin-4-yl}-3,4-dihydro-2H-pyrrolo[1,2-a]pyrazin-1-one [I-79];

7-{2-[4-(3,5-Dimethyl-pyrazol-1-yl)-phenylamino]-pyrimidin-4-yl}-6,8-dimethyl-3,4-dihydro-2H-pyrrolo[1,2-a]pyrazin-1-one [I-80];

1-{4-[4-(6,8-Dimethyl-1-oxo-1,2,3,4-tetrahydro-pyrrolo[1,2-a]pyrazin-7-yl)-pyrimidin-2-ylamino]-phenyl}-5-methyl-1H-pyrazole-4-carboxylic acid ethyl ester [I-81];

7-[2-(4-Isoxazol-5-yl-phenylamino)-pyrimidin-4-yl]-6,8-dimethyl-3,4-dihydro-2H-pyrrolo[1,2-a]pyrazin-1-one [I-82];

2-(4-{4-[4-(6,8-Dimethyl-1-oxo-1,2,3,4-tetrahydro-pyrrolo[1,2-a]pyrazin-7-yl)-pyrimidin-2-ylamino]-phenyl}-thiazol-2-yl)-acetamide [I-83];

4-{4-[4-(6,8-Dimethyl-1-oxo-1,2,3,4-tetrahydro-pyrrolo[1,2-a]pyrazin-7-yl)-pyrimidin-2-ylamino]-phenyl}-thiazol-2-yl)acetonitrile [I-84], 7-[2-(2,4-Dimethoxy-phenylamino)pyrimidin-4-yl]6,8-dimethyl-3,4-dihydro-2H-pyrrolo[1,2-a]pyrazin-1-one [I-85];

7-[2-(2-Chloro-4-fluoro-phenylamino)-pyrimidin-4-yl]-6,8-dimethyl-3,4-dihydro-2H-pyrrolo[1,2-a]pyrazin-1-one [I-86];

7-[2-(5-Chloro-2-methoxy-phenylamino)pyrimidin-4-yl]-6,8-dimethyl-3,4-dihydro-2H-pyrrolo[1,2-a]pyrazin-1-one [I-87];

7-[2-(5-Fluoro-2-methyl-phenylamino)-pyrimidin-4-yl]-6,8-dimethyl-3,4-dihydro-2H-pyrrolo[1,2-a]pyrazin-1-one [I-88];

6,8-Dimethyl-7-[2-(4-p-tolyloxy-phenylamino)-pyrimidin-4-yl]-3,4-dihydro-2H-pyrrolo[1,2-a]pyrazin-1-one [I-89];

N-(2-Diethylamino-ethyl)-4-[4-(6,8-dimethyl-1-oxo-1,2,3,4-tetrahydro-pyrrolo[1,2-a]pyrazin-7-yl)-pyrimidin-2-ylamino]-2-methyl-benzenesulfonamide [I-90];

N-3-Dimethylamino-propyl)-4-[4-(6,8-dimethyl-1-oxo-1,2,3,4-tetrahydro-pyrrolo[1,2-a]pyrazin-7-yl)-pyrimidin-2-ylamino]-2,N-dimethyl-benzenesulfonamide [I-91];

1-{4-[4-(6,8-Dimethyl-1-oxo-1,2,3,4-tetrahydro-pyrrolo[1,2-a]pyrazin-7-yl)-pyrimidin-2-ylamino]-phenyl}-3,5-dimethyl-1H-pyrazole-4-carboxylic acid ethyl ester [I-92];

2,6,8-Trimethyl-7-{2-[3-(2-methyl-pyrimidin-4-yl)-phenylamino]-pyrimidin-4-yl}—3,4-dihydro-2H-pyrrolo[1,2-a]pyrazin-1-one [I-93];

7-[2-(2,2-Dioxo-2,3-dihydro-1H-2-benzo[c]thiophen-5-ylamino)-pyrimidin-4-yl]-2,6,8-trimethyl-3,4-dihydro-2H-pyrrolo[1,2-a]pyrazin-1-one [I-94];

2-Ethyl-6,8-dimethyl-7-{2-[3-(2-methyl-pyrimidin-4-yl)-phenylamino]-pyrimidin-4-yl)-3,4-dihydro-2H-pyrrolo[1,2-a]pyrazin-1-one [I-95];

7-(2-[6-(4-Fluoro-phenoxy)-pyridin-3-ylamino]-pyrimidin-4-yl)-6,8-dimethyl-3,4-dihydro-2H-pyrrolo[1,2-a]pyrazin-1-one [I-95a];

6,8-Dimethyl-7-{2-[4-(1H-tetrazol-5-yl)-phenylamino]-pyrimidin-4-yl}-3,4-dihydro-2H-pyrrolo[1,2-a]pyrazin-1-one [I-95b];

6,8-Dimethyl-7-{2-[3-(piperidine-1-sulfonyl)-phenylamino]-pyrimidin-4-yl}-3,4-dihydro-2H-pyrrolo[1,2-a]pyrazin-1-one [I-95c];

2-{4-[4-(6,8-Dimethyl-1-oxo-1,2,3,4-tetrahydro-pyrrolo[1,2-a]pyrazin-7-yl)-pyrimidin-2-ylamino]-phenyl}-N-(2-methoxy-ethyl)-acetamide [I-96];

N-(2-Dimethylamino-ethyl)-2-{-[4-(6,8-dimethyl-1-oxo-1,2,3,4-tetrahydro-pyrrolo[1,2-a]pyrazin-7-yl)-pyrimidin-2-ylamino]-phenyl}-N-methyl-acetamide [I-97];

N-3-Dimethylamino-propyl)-2-{4-[4-(6,8-dimethyl-1-oxo-1,2,3,4-tetrahydro-pyrrolo[1,2-a]pyrazin-7-yl)-pyrimidin-2-ylamino]-phenyl}-N-methyl-acetamide [I-98];

6,8-Dimethyl-7-{2-[4-(2-morpholin-4-yl-2-oxo-ethyl)-phenylamino]-pyrimidin-4-yl}-3,4-dihydro-2H-pyrrolo[1,2-a]pyrazin-1-one [I-99];

7-(2-{4-[2-(4-Acetyl-piperazin-1-yl)-2-oxo-ethyl]-phenylamino}-pyrimidin-4-yl)-6,8-dimethyl-3,4-dihydro-2H-pyrrolo[1,2-a]pyrazin-1-one [I-100];

6,8-Dimethyl-7-(2-{4-[2-(4-methyl-piperazin-1-yl)-2-oxo-ethyl]-phenylamino}-pyrimidin-4-yl)-3,4-dihydro-2H-pyrrolo[1,2-a]pyrazin-1-one [I-101];

2-{4-[4-(6,8-Dimethyl-1-oxo-1,2,3,4-tetrahydro-pyrrolo[1,2-a]pyrazin-7-yl)-pyrimidin-2-ylamino]-phenyl}-acetamide [I-102];

2-{4-[4-(6,8-Dimethyl-1-oxo-1,2,3,4-tetrahydro-pyrrolo[1,2-a]pyrazin-7-yl)-pyrimidin-2-ylamino]-phenyl}-N-methyl-acetamide [I-103];

2-{4-[4-(6,8-Dimethyl-1-oxo-1,2,3,4-tetrahydro-pyrrolo[1,2-a]pyrazin-7-yl)-pyrimidin-2-ylamino]-phenyl}-N,N-dimethyl-acetamide [I-104];

3-{3-[4-(6,8-Dimethyl-1-oxo-1,2,3,4-tetrahydro-pyrrolo[1,2-a]pyrazin-7-yl)-pyrimidin-2-ylamino]-phenyl}-N-(2-methoxy-ethyl)-propionamide [I-105];

N-(2-Dimethylamino-ethyl)-3-{3-[4-(6,8-dimethyl-1-oxo-1,2,3,4-tetrahydro-pyrrolo[1,2-a]pyrazin-7-yl)-pyrimidin-2-ylamino]-phenyl}-N-methyl-propionamide [I-106];

N-(3-Dimethylamino-propyl)-3-{3-[4-(6,8-dimethyl-1-oxo-1,2,3,4-tetrahydro-pyrrolo[1,2-a]pyrazin-7-yl)-pyrimidin-2-ylamino]-phenyl}-N-methyl-propionamide [I-107];

6,8-Dimethyl-7-{2-[3-(3-morpholin-4-yl-3-oxo-propyl)-phenylamino]-pyrimidin-4-yl}-3,4-dihydro-2H-pyrrolo[1,2-a]pyrazin-1-one [I-108];

7-(2-{3-[3-(4-Acetyl-piperazin-1-yl)-3-oxo-propyl]-phenylamino}-pyrimidin-4-yl)-6,8-dimethyl-3,4-dihydro-2H-pyrrolo[1,2-a]pyrazin-1-one [I-109];

6,8-Dimethyl-7-(2-{3-[3-(4-methyl-piperazin-1-yl)-3-oxo-propyl]-phenylamino}-pyrimidin-4-yl)-3,4-dihydro-2H-pyrrolo[1,2-a]pyrazin-1-one [I-110];

3-{3-[4-(6,8-Dimethyl-1-oxo-1,2,3,4-tetrahydro-pyrrolo[1,2-a]pyrazin-7-yl)-pyrimidin-2-ylamino]-phenyl}-propionamide [I-111];

3-{3-[4-(6,8-Dimethyl-1-oxo-1,2,3,4-tetrahydro-pyrrolo[1,2-a]pyrazin-7-yl)-pyrimidin-2-ylamino]-phenyl}-N-meth-yl-propionamide [I-112];

3-{3-[4-(6,8-Dimethyl-1-oxo-1,2,3,4-tetrahydro-pyrrolo[1,2-a]pyrazin-7-yl)-pyrimidin-2-ylamino]-phenyl}-N,N-dimethyl-propionamide [I-113];

4-[4-(6,8-Dimethyl-1-oxo-1,2,3,4-tetrahydro-pyrrolo[1,2-a]pyrazin-7-yl)-pyrimidin-2-ylamino]-3-methoxy-N-(1-methyl-piperidinyl)-benzamide [I-114]; and 4-[4-(6,8-Dimethyl-1-oxo-1,2,3,4-tetrahydro-pyrrolo[1,2-a]pyrazin-7-yl)-pyrimidin-2-ylamino]-N-1-methyl-piperidin-4-yl)-benzamide [I-115].

In one highly preferred embodiment, the compound of the invention is selected from compounds [I-1], [I-2] and [I-3]:

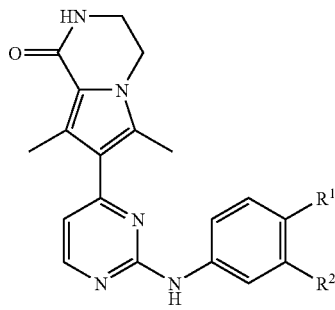

[I-1] $R^1$ = F; $R^2$ = H
[I-2] $R^1$ = N-morpholine; $R^2$ = H
[I-3] $R^1$ = N-morpholine; $R^2$ = OMe and pharmaceutically acceptable salts thereof.

In one particularly preferred embodiment, the compound of the invention is selected from compounds [I-63] and [I-94].

In one preferred embodiment, the compound of the invention is capable of inhibiting one or more protein kinases selected from CDK1/cyclin B, CDK2/cyclin A, CDK2/cyclin E, CDK4/cyclin D1, CDK7/cyclin H, CDK9/cyclin T1, GSK3β, aurora kinase, FLT3 and PLK1, as measured by the appropriate assay.

In one particularly preferred embodiment, the compound of the invention exhibits an $IC_{50}$ value for kinase inhibition of less than about 10 µM, more preferably less than about 5 µM, more preferably less than about 1 µM, more preferably still less than about 0.5 µM, more preferably less than about 0.1 µM, even more preferably, less than about 0.01 µM. Compounds falling within each of these preferred embodiments can be identified from Table 4 which show the $IC_{50}$ values for selected compounds of the invention. Details of the various kinase assays are disclosed in the accompanying Examples section.

In one preferred embodiment the compound of the invention is capable of exhibiting an antiproliferative effect in human cell lines, as measured by a standard 72 h Mrr cytotoxicity assay. Preferably, the compound of the invention exhibits an $IC_{50}$ value of less than 10 µM, more preferably less than 5 µM, even more preferably less than 1 µM as measured by said MTT assay. More preferably still, the compound exhibits an $IC_{50}$ value of less than 0.5 less µM, more preferably still less than 0.2 µM or 0.1 µM. Details of the standard 72 h MTT cytotoxicity assay are set forth in the accompanying Examples section.

Therapeutic Use

The compounds of the invention have been found to possess anti-proliferative activity and are therefore believed to be of use in the treatment of proliferative disorders such as cancers, leukaemias and other disorders associated with uncontrolled cellular proliferation such as psoriasis and restenosis.

Thus, one aspect of the invention relates to the use of a compound of the invention, or a pharmaceutically acceptable salt thereof, in the preparation of a medicament for treating a proliferative disorder.

As used herein the phrase "preparation of a medicament" includes the use of one or more of the above described compounds directly as the medicament in addition to its use in a screening programme for further anti-viral and/or antiproliferative agents or in any stage of the manufacture of such a medicament.

As defined herein, an anti-proliferative effect within the scope of the present invention may be demonstrated by the ability to inhibit cell proliferation in an in vitro whole cell assay, for example using any of the cell lines AGS, H1299 or SJSA-1, or by showing inhibition of the interaction between HDM2 and p53 in an appropriate assay. These assays, including methods for their performance, are described in more detail in the accompanying Examples. Using such assays it may be determined whether a compound is anti-proliferative in the context of the present invention.

One preferred embodiment therefore relates to the use of one or more compounds of the invention in the treatment of proliferative disorders. Preferably, the proliferative disorder is a cancer or leukaemia. The term proliferative disorder is used herein in a broad sense to include any disorder that requires control of the cell cycle, for example cardiovascular disorders such as restenosis and cardiomyopathy, auto-immune disorders such as glomerulonephritis and rheumatoid arthritis, dermatological disorders such as psoriasis, anti-inflammatory, anti-fungal, antiparasitic disorders such as malaria, emphysema and alopecia. In these disorders, the compounds of the present invention may induce apoptosis or maintain stasis within the desired cells as required.

In one preferred embodiment, the proliferative disorder is cancer or leukaemia.

In another preferred embodiment, the proliferative disorder is glomerulonephritis, rheumatoid arthritis, psoriasis or chronic obstructive pulmonary disorder.

The compounds of the invention may inhibit any of the steps or stages in the cell cycle, for example, formation of the nuclear envelope, exit from the quiescent phase of the cell cycle (G0), G1 progression, chromosome decondensation, nuclear envelope breakdown, START, initiation of DNA replication, progression of DNA replication, termination of DNA replication, centrosome duplication, G2 progression, activation of mitotic or meiotic functions, chromosome condensation, centrosome separation, microtubule nucleation, spindle formation and function, interactions with microtubule motor proteins, chromatid separation and segregation, inactivation of mitotic functions, formation of contractile ring, and cytokinesis functions. In particular, the compounds of the invention may influence certain gene functions such as chromatin binding, formation of replication complexes, replication licensing, phosphorylation or other secondary modification activity, proteolytic degradation, microtubule binding, actin binding, septin binding, microtubule organising centre nucleation activity and binding to components of cell cycle signalling pathways.

In one embodiment, the compound of the invention is administered in an amount sufficient to inhibit at least one CDK enzyme. Assays for determining CDK activity are described in more detail in the accompanying examples.

A further aspect of the invention relates to a method of treating a CDK-dependent disorder, said method comprising administering to a subject in need thereof, a compound of the invention or a pharmaceutically acceptable salt thereof, as defined above in an amount sufficient to inhibit a CDK.

Another aspect relates to the use of a compound of the invention as an anti-mitotic agent.

Another aspect of the invention relates to the use of a compound of the invention as an antiviral agent.

Thus, another aspect of the invention relates to the use of a compound of the invention in the preparation of a medicament for treating a viral disorder, such as human cytomegalovirus (HCMV), herpes simplex virus type 1 (HSV-1), human immunodeficiency virus type 1 (HIV-1), and varicella zoster virus (VZV).

In a more preferred embodiment of the invention, the compound of the invention is administered in an amount sufficient to inhibit one or more of the host cell CDKs involved in viral replication, i.e. CDK2, CDK7, CDK8, and CDK9 [Wang D, De la Fuente C, Deng L, Wang L, Zilberman I, Eadie C, Healey M, Stein D, Denny T, Harrison L E, Meijer L, Kashanchi F., Inhibition of human immunodeficiency virus type 1 transcription by chemical cyclin-dependent kinase inhibitors, J. Virol. 2001; 75: 7266-7279].

As defined herein, an anti-viral effect within the scope of the present invention may be demonstrated by the ability to inhibit CDK2, CDK7, CDK8 or CDK9.

In a particularly preferred embodiment, the invention relates to the use of one or more compounds of the invention in the treatment of a viral disorder which is CDK dependent or sensitive. CDK dependent disorders are associated with an above normal level of activity of one or more CDK enzymes. Such disorders preferably associated with an abnormal level of activity of CDK2, CDK7, CDK8 and/or CDK9. A CDK sensitive disorder is a disorder in which an aberration in the CDK level is not the primary cause, but is downstream of the primary metabolic aberration. In such scenarios, CDK2, CDK7, CDK8 and/or CDK9 can be said to be part of the sensitive metabolic pathway and CDK inhibitors may therefore be active in treating such disorders.

Another aspect relates to the use of compounds of the invention, or pharmaceutically acceptable salts thereof, in the preparation of a medicament for treating diabetes.

In a particularly preferred embodiment, the diabetes is type II diabetes.

GSK3 is one of several protein kinases that phosphorylate glycogen synthase (GS). The stimulation of glycogen synthesis by insulin in skeletal muscle results from the dephosphorylation and activation of GS. GSK3's action on GS thus results in deactivation of the latter and thus suppression of the conversion of glucose into glycogen in muscles.

Type II diabetes (non-insulin dependent diabetes mellitus) is a multi-factorial disease. Hyperglycaemia is due to insulin resistance in the liver, muscles, and other tissues, coupled with impaired secretion of insulin. Skeletal muscle is the main site for insulin-stimulated glucose uptake, there it is either removed from circulation or converted to glycogen. Muscle glycogen deposition is the main determinant in glucose homeostasis and type II diabetics have defective muscle glycogen storage. There is evidence that an increase in GSK3 activity is important in type II diabetes [Chen, Y. H.; Hansen, L.; Chen, M X.; Bjorbaek, C.; Vestergaard, H.; Hansen, T.; Cohen, P. T.; Pedersen, O. *Diabetes,* 1994, 43, 1234]. Furthermore, it has been demonstrated that GSK3 is over-expressed in muscle cells of type II diabetics and that an inverse correlation exists between skeletal muscle GSK3 activity and insulin action [Nikoulina, S. E.; Ciaraldi, T. P.; Mudaliar, S.; Mohideen, P.; Carter, L.; Henry, R. R. *Diabetes,* 2000, 49, 263].

GSK3 inhibition is therefore of therapeutic significance in the treatment of diabetes, particularly type II, and diabetic neuropathy.

It is notable that GSK3 is known to phosphorylate many substrates other than GS, and is thus involved in the regulation of multiple biochemical pathways. For example, GSK is highly expressed in the central and peripheral nervous systems.

Another aspect therefore relates to the use of compounds of the invention, or pharmaceutically acceptable salts thereof, in the preparation of a medicament for treating a CNS disorders, for example neurodegenerative disorders.

In one preferred embodiment, the neurodegenerative disorder is neuronal apoptosis.

In another preferred embodiment, the CNS disorder is Alzheimer's disease.

Tau is a GSK-3 substrate which has been implicated in the etiology of Alzheimer's disease. In healthy nerve cells, Tau co-assembles with tubulin into microtubules. However, in Alzheimer's disease, tau forms large tangles of filaments, which disrupt the microtubule structures in the nerve cell, thereby impairing the transport of nutrients as well as the transmission of neuronal messages.

Without wishing to be bound by theory, it is believed that GSK3 inhibitors may be able to prevent and/or reverse the abnormal hyperphosphorylation of the microtubule-associated protein tau that is an invariant feature of Alzheimer's disease and a number of other neurodegenerative diseases, such as progressive supranuclear palsy, corticobasal degeneration and Pick's disease. Mutations in the tau gene cause inherited forms of fronto-temporal dementia, further underscoring the relevance of tau protein dysfunction for the neurodegenerative process [Goedert, M. *Curr. Opin. Gen. Dev.,* 2001, 11, 343].

Another aspect relates to the use of compounds of the invention, or pharmaceutically acceptable salts thereof, in the preparation of a medicament for treating bipolar disorder.

Yet another aspect relates to the use of compounds of the invention, or pharmaceutically acceptable salts thereof, in the preparation of a medicament for treating a stroke.

Reducing neuronal apoptosis is an important therapeutic goal in the context of head trauma, stroke, epilepsy, and motor neuron disease [Mattson, M. P. Nat. Rev. Mol. Cell. Biol., 2000, 1, 120]. Therefore, GSK3 as a pro-apoptotic factor in neuronal cells makes this protein kinase an attractive therapeutic target for the design of inhibitory drugs to treat these diseases.

Yet another aspect relates to the use of compounds of the invention, or pharmaceutically acceptable salts thereof, in the preparation of a medicament for treating alopecia Hair growth is controlled by the Wnt signalling pathway, in particular Wnt-3. In tissue-culture model systems of the skin, the expression of non-degradable mutants of β-catenin leads to a dramatic increase in the population of putative stem cells, which have greater proliferative potential [Zhu, A. J.; Watt, F. M. Development, 1999, 126, 2285]. This population of stem cells expresses a higher level of non-cadherin-associated β-catenin [DasGupta, R.; Fuchs, E. Development, 1999, 126, 4557], which may contribute to their high proliferative potential. Moreover, transgenic mice overexpressing a truncated β-catenin in the skin undergo de novo hair-follicle morphogenesis, which normally is only established during embryogenesis. The ectopic application of GSK3 inhibitors may therefore be therapeutically useful in the treatment of baldness and in restoring hair growth following chemotherapy-induced alopecia A further aspect of the invention relates to a method of treating a GSK3-dependent disorder, said method comprising administering to a subject in need thereof, a compound of the invention or a pharmaceutically acceptable salt thereof, as defined above in an amount sufficient to inhibit GSK3.

Preferably, the compound of the invention, or pharmaceutically acceptable salt thereof, is administered in an amount sufficient to inhibit GSK3β.

In one embodiment of the invention, the compound of the invention is administered in an amount sufficient to inhibit at least one PLK enzyme.

A further aspect of the invention relates to a method of treating a PLK-dependent disorder, said method comprising administering to a subject in need thereof, a compound of the invention or a pharmaceutically acceptable salt thereof, as defined above in an amount sufficient to inhibit PLK.

The polo-like kinases (PLKs) constitute a family of serine/threonine protein kinases. Mitotic Drosophila melanogaster mutants at the polo locus display spindle abnormalities [Sunkel et al., J. Cell Sci., 1988, 89, 25] and polo was found to encode a mitotic kinase [Llamazares et al., Genes Dev., 1991, 5, 2153]. In humans, there exist three closely related PLKs [Glover et al., Genes Dev., 1998, 12, 3777]. They contain a highly homologous amino-terminal catalytic kinase domain and their carboxyl termini contain two or three conserved regions, the polo boxes. The function of the polo boxes remains incompletely understood but they are implicated in the targeting of PLKs to subcellular compartments [Lee et al., Proc. Natl. Acad. Sci. USA, 1998, 95, 9301; Leung et al., Nat. Struct. Biol., 2002, 9, 719], mediation of interactions with other proteins [Kauselmann et al., EMBO J., 1999, 18, 5528], or may constitute part of an autoregulatory domain [Nigg, Curr. Opin. Cell Biol., 1998, 10, 776]. Furthermore, the polo box-dependent PLK1 activity is required for proper metaphase/anaphase transition and cytokinesis [Yuan et al., Cancer Res., 2002, 62, 4186; Seong et al., J. Biol. Chem., 2002, 277, 32282].

Studies have shown that human PLKs regulate some fundamental aspects of mitosis [Lane et al., J. Cell Biol., 1996, 135, 1701; Cogswell et al, Cell Growth Differ., 2000, 11, 615]. In particular, PLK1 activity is believed to be necessary for the functional maturation of centrosomes in late G2/early prophase and subsequent establishment of a bipolar spindle. Depletion of cellular PLK1 through the small interfering RNA (siRNA) technique has also confirmed that this protein is required for multiple mitotic processes and completion of cytokinesis [Liu et al., Proc. Natl. Acad. Sci. USA, 2002, 99, 8672].

In a more preferred embodiment of the invention, the compound of the invention is administered in an amount sufficient to inhibit PLK1.

Of the three human PLKs, PLK1 is the best characterized; it regulates a number of cell division cycle effects, including the onset of mitosis [Toyoshima-Morimoto et al., Nature, 2001, 410, 215; Roshak et al., Cell. Signalling, 2000, 12, 405], DNA-damage checkpoint activation [Smits et al., Nat. Cell Biol., 2000, 2, 672; van Vugt et al, J. Biol. Chem., 2001, 276, 41656], regulation of the anaphase promoting complex [Sumara et al., Mol. Cell, 2002, 9, 515; Golan et al., J. Biol. Chem., 2002, 277, 15552; Kotani et al, Mol. Cell, 1998, 1, 371], phosphorylation of the proteasome [Feng et al., Cell Growth Differ., 2001, 12, 29], and centrosome duplication and maturation [Dai et al., Oncogene, 2002, 21, 6195].

Specifically, initiation of mitosis requires activation of M-phase promoting factor (MPF), the complex between the cyclin dependent kinase CDK1 and B-type cyclins [Nurse, Nature, 1990, 344, 503]. The latter accumulate during the S and G2 phases of the cell cycle and promote the inhibitory phosphorylation of the MPF complex by WEE1, MIK1, and MYT1 kinases. At the end of the G2 phase, corresponding dephosphorylation by the dual-specificity phosphatase CDC25C triggers the activation of MPF [Nigg, Nat. Rev. Mol. Cell. Biol., 2001, 2, 21]. In interphase, cyclin B localizes to the cytoplasm [Hagting et al., EMBO J., 1998, 17, 4127], it then becomes phosphorylated during prophase and this event causes nuclear translocation [Hagting et al, Curr. Biol., 1999, 9, 680; Yang et al., J. Biol. Chem., 2001, 276, 3604]. The nuclear accumulation of active MPF during prophase is thought to be important for initiating M-phase events [Takizawa et al., Curr. Opin. Cell Biol., 2000, 12, 658]. However, nuclear MPF is kept inactive by WEE1 unless counteracted by CDC25C. The phosphatase CDC25C itself, localized to the cytoplasm during interphase, accumulates in the nucleus in prophase [Seki et al., Mol. Biol. Cell, 1992, 3, 1373; Heald et al., Cell, 1993, 74, 463; Dalal et al., Mol. Cell. Biol., 1999, 19, 4465]. The nuclear entry of both cyclin B [Toyoshima-Morimoto et al., Nature, 2001, 410, 215] and CDC25C [Toyoshima-Morimoto et al., EMBO Rep., 2002, 3, 341] are promoted through phosphorylation by PLK1 [Roshak et al., Cell. Signalling, 2000, 12, 405]. This kinase is an important regulator of M-phase initiation.

In one particularly preferred embodiment, the compounds of the invention are ATP-antagonistic inhibitors of PLK1.

In the present context ATP antagonism refers to the ability of an inhibitor compound to diminish or prevent PLK catalytic activity, i.e. phosphotransfer from ATP to a macromolecular PLK substrate, by virtue of reversibly or irreversibly binding at the enzyme's active site in such a manner as to impair or abolish ATP binding.

In another preferred embodiment, the compound of the invention is administered in an amount sufficient to inhibit PLK2 and/or PLK3.

Mammalian PLK2 (also known as SNK) and PLK3 (also known as PRK and FNK) were originally shown to be immediate early gene products. PLK3 kinase activity appears to peak during late S and G2 phase. It is also activated during DNA damage checkpoint activation and severe oxidative stress. PLK3 also plays an important role in the regulation of microtubule dynamics and centrosome function in the cell and deregulated PLK3 expression results in cell cycle arrest and apoptosis [Wang et al., Mol. Cell. Biol., 2002, 22, 3450]. PLK2 is the least well understood homologue of the three PLKs. Both PLK2 and PLK3 may have additional important post-mitotic functions [Kauselmann et al., EMBO J., 1999, 18, 5528].

In another preferred embodiment, the compound of the invention is administered in an amount sufficient to inhibit at least one aurora kinase. Preferably, the aurora kinase is aurora kinase A, aurora kinase B or aurora kinase C.

A further aspect of the invention relates to a method of treating an aurora kinase-dependent disorder, said method comprising administering to a subject in need thereof, a compound of the invention or a pharmaceutically acceptable salt thereof, as defined above in an amount sufficient to inhibit an aurora kinase.

In another preferred embodiment, the compound of the invention is administered in an amount sufficient to inhibit at least one tyrosine kinase.

Preferably, the tyrosine kinase is Ableson tyrosine kinase (13CR-ABL), FMS-related tyrosine kinase 3 (FLT3), platelet-derived growth factor (PDGOF) receptor tyrosine kinase or vascular endothelial growth factor (VEGF) receptor tyrosine kinase.

A further aspect of the invention relates to a method of treating a tyrosine kinase-dependent disorder, said method comprising administering to a subject in need thereof, a compound of the invention or a pharmaceutically acceptable salt thereof, as defined above in an amount sufficient to inhibit a tyrosine kinase.

Another aspect relates to the use of a compound of the invention for inhibiting a protein kinase.

A further aspect of the invention relates to a method of inhibiting a protein kinase, said method comprising contacting said protein kinase with a compound of the invention.

Preferably, the protein kinase is selected from a CDK, GSK, an aurora kinase, PLK and a tyrosine kinase.

In a preferred embodiment of this aspect, the protein kinase is a cyclin dependent kinase. Preferably, the protein kinase is CDK1, CDK2, CDK3, CDK4, CDK6, CDK7, CDK8 or CDK9, more preferably CDK2.

The compounds of the invention are also useful in the preparation of medicaments for the treatment of various ophthalmic disorders. Preferably, the ophthalmic disorder is glaucoma, exudative age-related macular degeneration (AMD) or proliferative diabetic retinopathy (PDR).

The disease state referred to as glaucoma is characterized by a permanent loss of visual function due to irreversible damage to the optic nerve. The several morphologically or functionally distinct tppes of glaucoma are typically characterized by elevated intraocular pressure (IOP), which is considered to be causally related to the pathological course of the disease, Ocular hypertension is a condition wherein intraocular pressure is elevated, but no apparent loss of visual function has occurred; such patients are considered to be a high risk for the eventual development of the visual loss associated with glaucoma. GSK-3 inhibitors are useful for the treatment of eye diseases such as glaucoma. It has been shown that a component of the Wnt signalling pathway, frizzled related protein (FRP), is differentially expressed in a number of glaucomatous trabecular meshwork cell lines and can disrupt the normal signalling cascade causing an increase in outflow resistance and development of elevated IOP. Hellberg M. R. et al (US20040186159) have shown that through the interaction of GSK-3 with components of the Wnt signalling pathway, inhibition of GSK-3 by pharmacological agents can circumvent the FRP mediated antagonism of the Wnt signaling pathway caused by the elevated levels of FRP and counteract the increase in outflow resistance that results from the increase in production of FRP in individuals with glaucoma.

CTGF is a secreted cytokine which is known to increase extracellular matrix (ECM) production, primarily via increased deposition of collagen I and of fibronectin. Overexpression of CTGF has previously been implicated as a major causative factor in conditions such as scleroderma, fibroproliferative diseases, scarring, etc. in which there is an overaccumulation of ECM components. An overaccumulation of extracellular matrix materials in the region of the trabecular meshwork (TM) is also a hallmark of many forms of glaucoma; such increases are believed to lead to increased resistance to aqueous outflow, and therefore elevated intraocular pressures. Fleenor D L et al (US20050234075) have shown that GSK-3 inhibitors and CDK inhibitors can inhibit both basal and TGF.beta.2-induced CTGF expression in human TM cells therefore compounds of the current invention are useful for the treatment of glaucoma.

The compounds of the invention are also useful in the treatment of AMD and PDR. Exudative age-related macular degeneration (AMD) and proliferative diabetic retinopathy (PDR) are the major causes of acquired blindness in developed countries and are characterized by pathologic posterior segment neovascularization in the eye. The inciting cause in both exudative AMD and PDRis still unknown, however, the elaboration of various proangiogenic growth factors appears to be a common stimulus. Soluble growth factors, such as vascular endothelial growth factor (VEGF), platelet-derived growth factor (PDGF), basic fibroblast growth factor (bFGF or FGF-2), insulin-like growth factor 1 (IGF-1), angiopoietins, etc., have been found in tissues and fluids removed from patients with pathologic ocular angiogenesis. Inhibition or blockade of the activity of these growth factors and of other intracellular enzymes such as aurora kinases has been shown to have an antiangiogenic effect. Thus compounds of the current invention are useful for treating ophthalmic diseases characterised by neovascularization.

Pharmaceutical Compositions

A further aspect of the invention relates to a pharmaceutical composition comprising a compound of the invention admixed with one or more pharmaceutically acceptable diluents, excipients or carriers. Even though the compounds of the present invention (including their pharmaceutically acceptable salts, esters and pharmaceutically acceptable solvates) can be administered alone, they will generally be administered in admixture with a pharmaceutical carrier, excipient or diluent, particularly for human therapy. The pharmaceutical compositions may be for human or animal usage in human and veterinary medicine.

Examples of such suitable excipients for the various different forms of pharmaceutical compositions described herein may be found in the "Handbook of Pharmaceutical Excipients, $2^{nd}$ Edition, (1994), Edited by A Wade and P J Weller.

Acceptable carriers or diluents for therapeutic use are well known in the pharmaceutical art, and are described, for example, in Remington's Pharmaceutical Sciences, Mack Publishing Co. (A. R. Gennaro edit. 1985).

Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s).

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

Salts/Esters

The compounds of the invention can be present as salts or esters, in particular pharmaceutically acceptable salts or esters.

Pharmaceutically acceptable salts of the compounds of the invention include suitable acid addition or base salts thereof. A review of suitable pharmaceutical salts may be found in Berge et al, J Pharm Sci, 66, 1-19 (1977). Salts are formed, for example with strong inorganic acids such as mineral acids, e.g. sulphuric acid, phosphoric acid or hydrohalic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid.

Esters are formed either using organic acids or alcohols/hydroxides, depending on the functional group being esterified. Organic acids include carboxylic acids, such as alkanecarboxylic acids of 1 to 12 carbon atoms which are unsubstituted or substituted (e.g., by halogen), such as acetic acid; with saturated or unsaturated dicarboxylic acid, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Suitable hydroxides include inorganic hydroxides, such as sodium hydroxide, potassium hydroxide, calcium hydroxide, aluminium hydroxide. Alcohols include alkanealcohols of 1-12 carbon atoms which may be unsubstituted or substituted, e.g. by a halogen).

Enantiomers/Tautomers

In all aspects of the present invention previously discussed, the invention includes, where appropriate all enantiomers and tautomers of the compounds of the invention. The person skilled in the art will recognise compounds that possess an optical properties (one or more chiral carbon atoms) or tautomeric characteristics. The corresponding enantiomers and/or tautomers may be isolated/prepared by methods known in the art.

Stereo and Geometric Isomers

Some of the compounds of the invention may exist as stereoisomers and/or geometric isomers—e.g. they may possess one or more asymmetric and/or geometric centres and so may exist in two or more stereoisomeric and/or geometric forms. The present invention contemplates the use of all the individual stereoisomers and geometric isomers of those inhibitor agents, and mixtures thereof. The terms used in the claims encompass these forms, provided said forms retain the appropriate functional activity (though not necessarily to the same degree).

The present invention also includes all suitable isotopic variations of the agent or a pharmaceutically acceptable salt thereof. An isotopic variation of an agent of the present invention or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as $^2$H, $^3$H, $^{13}$C, $^{14}$C, $^{15}$N, $^{17}$O, $^{18}$O, $^{31}$P, $^{32}$P, $^{35}$S, $^{18}$F and $^{36}$Cl, respectively. Certain isotopic variations of the agent and pharmaceutically acceptable salts thereof, for example, those in which a radioactive isotope such as $^3$H or $^{14}$C is incorporated, are useful in drug and/or substrate tissue distribution studies. Tritiated, i.e., $^3$H, and carbon-14, i.e., $^{14}$C, isotopes are particularly preferred for their ease of preparation and detectability. Further, substitution with isotopes such as deuterium, i.e., $^2$H, may afford certain therapeutic advantages resulting from greater metabolic stability, for example, increased in vivo half-life or reduced dosage requirements and hence may be preferred in some circumstances. Isotopic variations of the agent of the present invention and pharmaceutically acceptable salts thereof of this invention can generally be prepared by conventional procedures using appropriate isotopic variations of suitable reagents.

Solvates

The present invention also includes solvate forms of the compounds of the present invention. The terms used in the claims encompass these forms.

Polymorphs

The invention furthermore relates to the compounds of the present invention in their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

Prodrugs

The invention further includes the compounds of the present invention in prodrug form. Such prodrugs are generally compounds of the invention wherein one or more appropriate groups have been modified such that the modification may be reversed upon administration to a human or mammalian subject. Such reversion is usually performed by an enzyme naturally present in such subject, though it is possible for a second agent to be administered together with such a prodrug in order to perform the reversion in vivo. Examples of such modifications include ester (for example, any of those described above), wherein the reversion may be carried out be an esterase etc. Other such systems will be well known to those skilled in the art.

Administration

The pharmaceutical compositions of the present invention may be adapted for oral, rectal, vaginal, parenteral, intramuscular, intraperitoneal, intraarterial, intrathecal, intrabronchial, subcutaneous, intradermal, intravenous, nasal, buccal or sublingual routes of administration.

For oral administration, particular use is made of compressed tablets, pills, tablets, gellules, drops, and capsules. Preferably, these compositions contain from 1 to 250 mg and more preferably from 10-100 mg, of active ingredient per dose.

Other forms of administration comprise solutions or emulsions which may be injected intravenously, intraarterially, intrathecally, subcutaneously, intradermally, intraperitoneally or intramuscularly, and which are prepared from sterile or sterilisable solutions. The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Injectable forms may contain between 10-1000 mg, preferably between 10-250 mg, of active ingredient per dose.

Compositions may be formulated in unit dosage form, i.e., in the form of discrete portions containing a unit dose, or a multiple or sub-unit of a unit dose.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

Depending upon the need, the agent may be administered at a dose of from 0.01 to 30 mg/kg body weight, such as from 0.1 to 10 mg/kg, more preferably from 0.1 to 1 mg/kg body weight.

In an exemplary embodiment, one or more doses of 10 to 150 mg/day will be administered to the patient for the treatment of malignancy.

Combinations

In a particularly preferred embodiment, the one or more compounds of the invention are administered in combination with one or more other active agents, for example, existing anticancer drugs available on the market. In such cases, the compounds of the invention may be administered consecutively, simultaneously or sequentially with the one or more other active agents.

Anticancer drugs in general are more effective when used in combination. In particular, combination therapy is desirable in order to avoid an overlap of major toxicites, mechanism of action and resistance mechanism(s). Furthermore, it is also desirable to administer most drugs at their maximum tolerated doses with minimum time intervals between such doses. The major advantages of combining chemotherapeutic drugs are that it may promote additive or possible synergistic effects through biochemical interactions and also may decrease the emergence of resistance in early tumor cells which would have been otherwise responsive to initial chemotherapy with a single agent. An example of the use of biochemical interactions in selecting drug combinations is demonstrated by the administration of leucovorin to increase the binding of an active intracellular metabolite of 5-fluorouracil to its target, thymidylate synthase, thus increasing its cytotoxic effects.

Numerous combinations are used in current treatments of cancer and leukemia. A more extensive review of medical practices may be found in "Oncologic Therapies" edited by E. E. Vokes and H. M. Golomb, published by Springer.

Beneficial combinations may be suggested by studying the growth inhibitory activity of the test compounds with agents known or suspected of being valuable in the treatment of a particular cancer initially or cell lines derived from that cancer. This procedure can also be used to determine the order of administration of the agents, i.e. before, simultaneously, or after delivery. Such scheduling may be a feature of all the cycle acting agents identified herein.

Assays

Another aspect of the invention relates to the use of a compound of the invention as defined hereinabove in an assay for identifying further candidate compounds that influence the activity of one or more of the following: a CDK, FLT-3, an aurora kinase, GSK-3, PLK and/or a tyrosine kinase.

Preferably, the assay is capable of identifying candidate compounds that are capable of inhibiting one or more of a CDK enzyme, FLT-3, an auroroa kinase, a tyrosine kinase, GSK or a PLK enzyme.

More preferably, the assay is a competitive binding assay.

Preferably, the candidate compound is generated by conventional SAR modification of a compound of the invention.

As used herein, the term "conventional SAR modification" refers to standard methods known in the art for varying a given compound by way of chemical derivatisation.

Thus, in one aspect, the identified compound may act as a model (for example, a template) for the development of other compounds. The compounds employed in such a test may be free in solution, affixed to a solid support, borne on a cell surface, or located intracellularly. The abolition of activity or the formation of binding complexes between the compound and the agent being tested may be measured.

The assay of the present invention may be a screen, whereby a number of agents are tested. In one aspect, the assay method of the present invention is a high through-put screen.

This invention also contemplates the use of competitive drug screening assays in which neutralising antibodies capable of binding a compound specifically compete with a test compound for binding to a compound.

Another technique for screening provides for high throughput screening (HTS) of agents having suitable binding affinity to the substances and is based upon the method described in detail in WO 84/03564.

It is expected that the assay methods of the present invention will be suitable for both small and large-scale screening of test compounds as well as in quantitative assays.

Preferably, the competitive binding assay comprises contacting a compound of the invention with a CDK, FLT-3, an aurora kinase, GSK-3, PLK and/or a tyrosine kinase enzyme in the presence of a known substrate of said enzyme and detecting any change in the interaction between said enzyme and said known substrate.

A further aspect of the invention provides a method of detecting the binding of a ligand to a CDK, FLT-3, an aurora kinase, GSK-3, PLK or a tyrosine kinase enzyme, said method comprising the steps of:
(i) contacting a ligand with a CDK, FLT-3, an aurora kinase, GSK-3, PLK or a tyrosine kinase enzyme in the presence of a known substrate of said enzyme;
(ii) detecting any change in the interaction between said enzyme and said known substrate;
and wherein said ligand is a compound of the invention.

One aspect of the invention relates to a process comprising the steps of:

(a) performing an assay method described hereinabove;
(b) identifying one or more ligands capable of binding to a ligand binding domain; and
(c) preparing a quantity of said one or more ligands.

Another aspect of the invention provides a process comprising the steps of:
(a) performing an assay method described hereinabove;
(b) identifying one or more ligands capable of binding to a ligand binding domain; and
(c) preparing a pharmaceutical composition comprising said one or more ligands.

Another aspect of the invention provides a process comprising the steps of:
(a) performing an assay method described hereinabove;
(b) identifying one or more ligands capable of binding to a ligand binding domain;
(c) modifying said one or more ligands capable of binding to a ligand binding domain;
(d) performing the assay method described hereinabove;
(e) optionally preparing a pharmaceutical composition comprising said one or more ligands.

The invention also relates to a ligand identified by the method described hereinabove.

Yet another aspect of the invention relates to a pharmaceutical composition comprising a ligand identified by the method described hereinabove.

Another aspect of the invention relates to the use of a ligand identified by the method described hereinabove in the preparation of a pharmaceutical composition for use in the treatment of proliferative disorders.

The above methods may be used to screen for a ligand useful as an inhibitor of one or more CDK enzymes, FLT-3, an aurora kinase, GSK-3, PLK or a tyrosine kinase enzyme.

Synthesis

A further aspect of the invention relates to a process for preparing a compound of formula I as defined above, said process comprising the steps of:

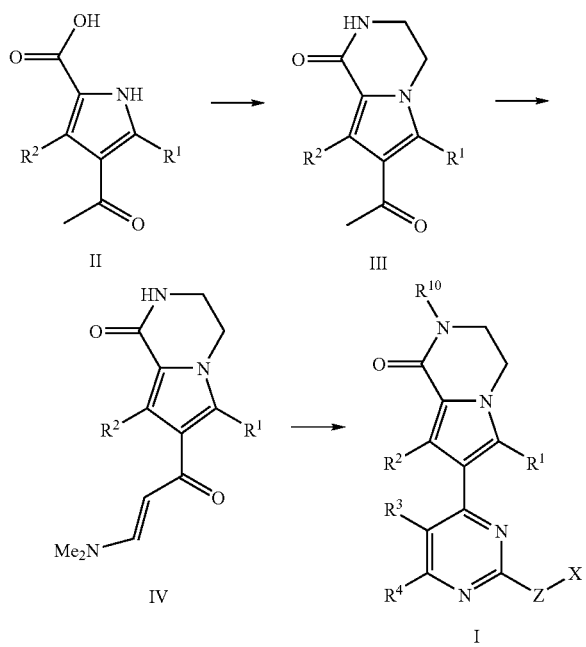

(i) converting a compound of formula II to a compound of formula III;
(ii) converting said compound of formula III to a compound of formula IV;
(iii) converting said compound of formula IV to a compound of formula I.

In one preferred embodiment of the invention, step (i) of the process comprises reacting a compound of formula II with 2-chloroethylamine hydrochloride, V,

to form a compound of formula III.

In a more preferred embodiment of the invention, step (i) is carried out in the presence of carbonyldiimidazole in anhydrous DMF.

In one preferred embodiment of the invention, step (ii) comprises reacting said compound of formula III with a compound of formula VI,

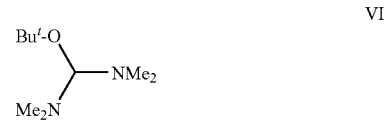

to form a compound of formula IV.

In one preferred embodiment of the invention, step (iii) comprises reacting said compound of formula IV with a compound of formula VII

where Z and X are as defined above, to form a compound of formula I.

More preferably, step (iii) comprises reacting said compound of formula IV with a compound of formula VIIa

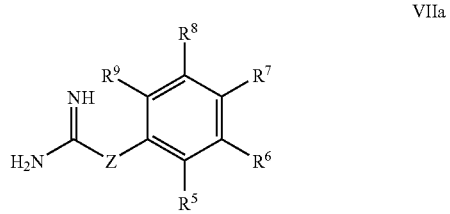

where Z and $R^5$-$R^9$ are as defined above, to form a compound of formula Ia as defined above.

One particularly preferred embodiment of the invention relates to a process for preparing 2-anilino-4-(6,8-dimethyl-3,4-dihydropyrrolo[1,2-a]pyrazin-1(2H)-one) pyrimidines.

The preferred initial route via coupling of the pyrrole acid precursor is detailed below in Scheme 1.

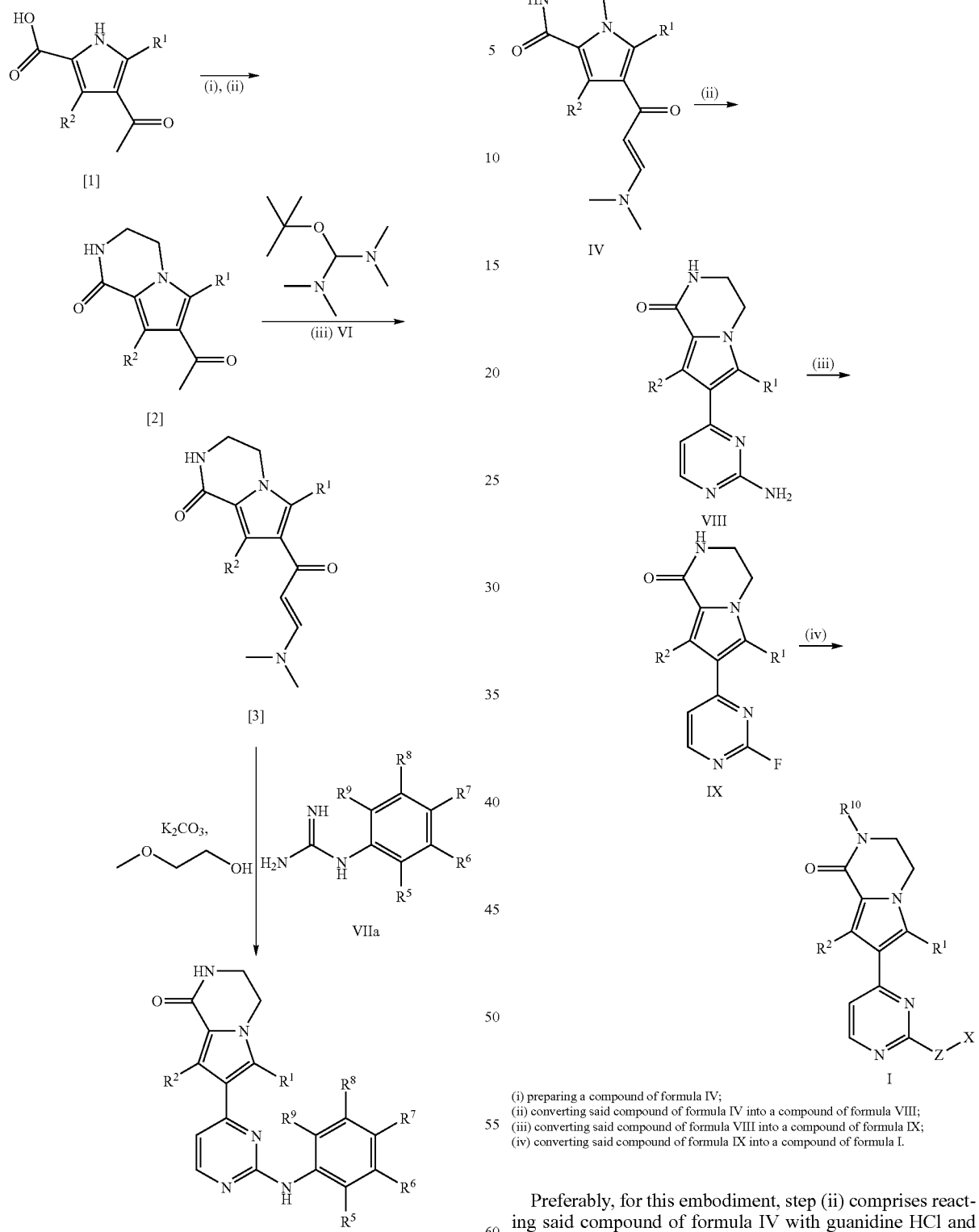

(i) preparing a compound of formula IV;
(ii) converting said compound of formula IV into a compound of formula VIII;
(iii) converting said compound of formula VIII into a compound of formula IX;
(iv) converting said compound of formula IX into a compound of formula I.

Preferably, for this embodiment, step (ii) comprises reacting said compound of formula IV with guanidine HCl and sodium ethoxide in ethanol.

Preferably, for this embodiment, step (iii) comprises reacting said compound of formula VIII with HF/pyridine and t-butyl nitrite.

Preferably, for this embodiment, Z is NH and step (iv) comprises reacting said compound of formula IX with $NH_2$—X.

In an alternative aspect, the invention provides a process for preparing compounds of formula I which comprises the steps of:

In one highly preferred embodiment, step (iv) comprises reacting said compound of formula IX with an aniline of formula XI,

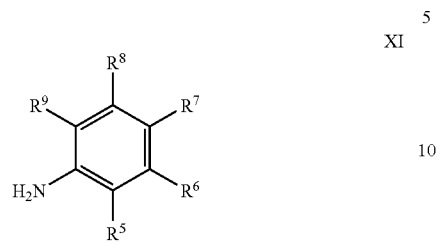

More preferably, said compound of formula IX is reacted with an aniline of formula XI in presence of trifluoroacetic acid in 2,2,2-trifluoroethanol.

In an alternative embodiment, step (iv) comprises reacting said compound of formula IX with an alkyl halide, $R^{10}$-Hal, and converting the product so formed into a compound of formula I (where $R^{10} \neq H$ and Z is NH) by treating with $NH_2$—X.

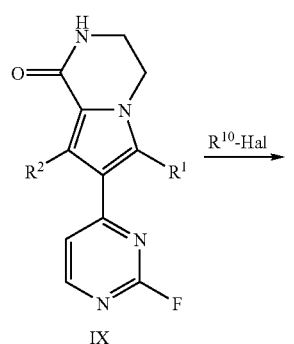

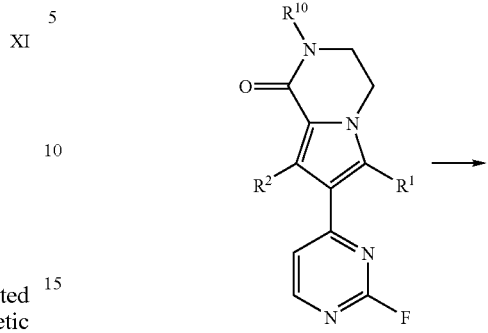

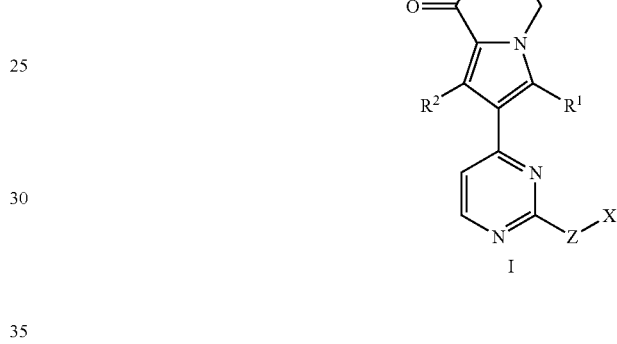

In one highly preferred embodiment, the compounds of the invention are prepared in accordance with Scheme 2 below.

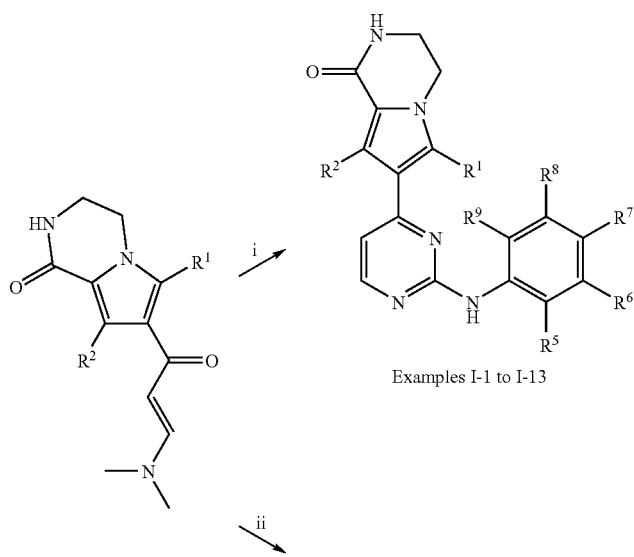

Examples I-1 to I-13

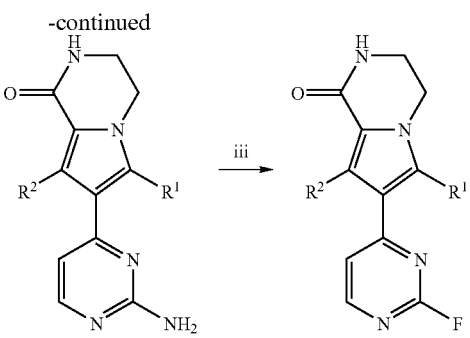

Reagents:
(i) Aryl guanidines, DBU, pyridine, 100° C., 18 h.
(ii) Guanidine HCl, sodium ethoxide, ethanol, 77° C. overnight.
(iii) HF/pyridine, t-butyl nitrite, -5° C. Preferably $R^1$ and $R^2$ = Me.

In another highly preferred embodiment, the compounds of the invention are prepared in accordance with Scheme 3 below.

In another highly preferred embodiment, the compounds of the invention are prepared in accordance with Scheme 4 below.

Scheme 3

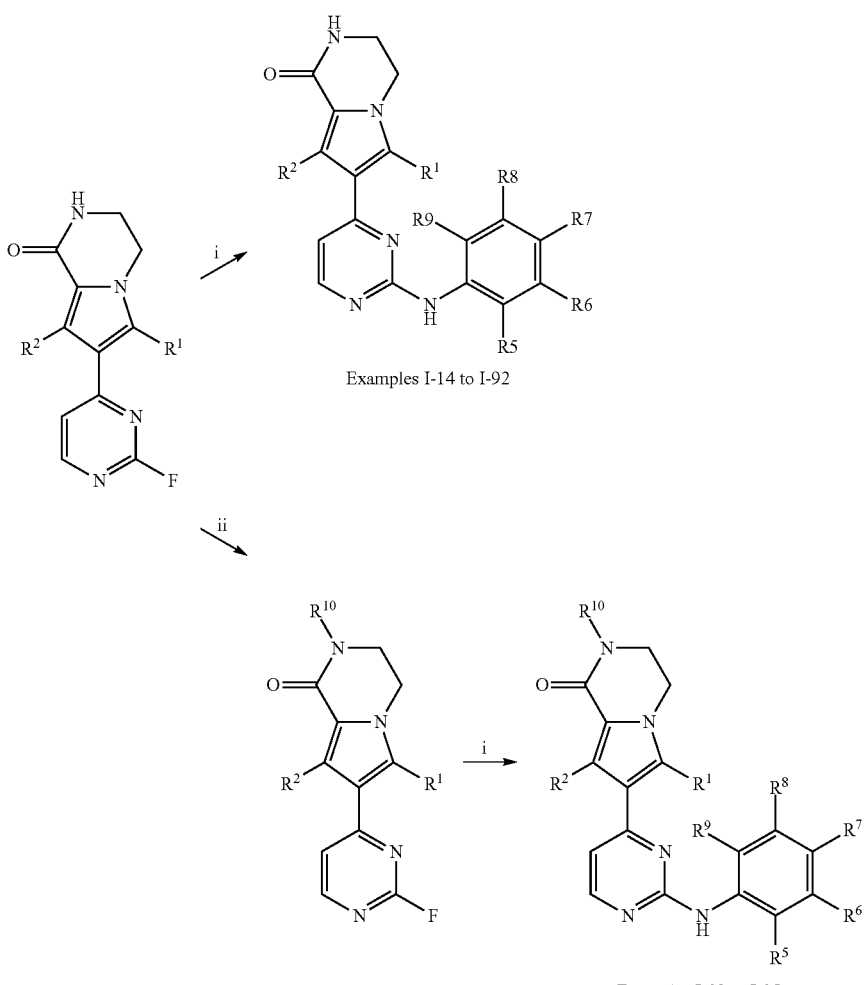

Reagents:
i. Anilines, trifluoroacetic acid, 2,2,2-trifluoroethanol, reflux 4-12 h.
ii. NaH, DMF, alkyl halide, -70° C. - rt. Preferably $R^1$ and R = Me.

Scheme 4

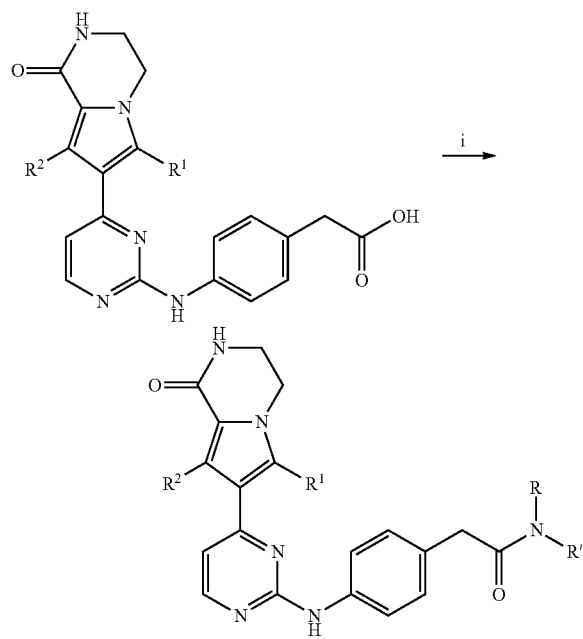

Examples I-96 to I-104

Reagents: i. EDCl, HOBt, THF, rt 16 h. Preferably R$^1$ and R$^2$ = Me.

In another highly preferred embodiment, the compounds of the invention are prepared in accordance with Scheme 5 below.

Scheme 5

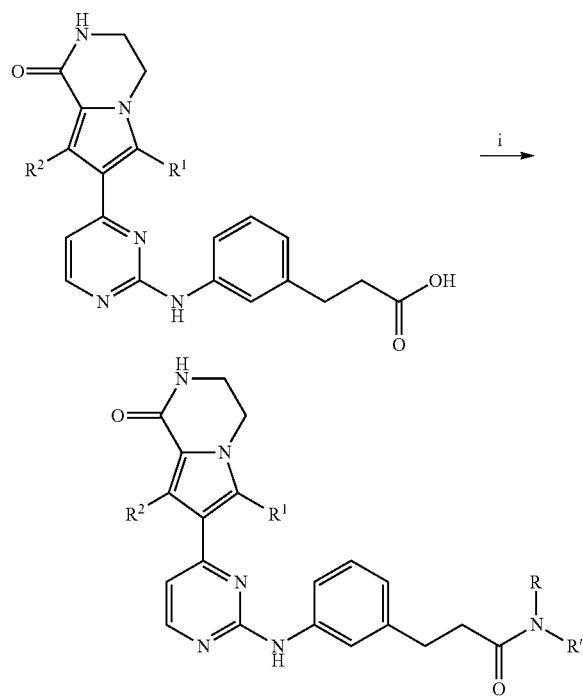

Examples I-105 to I-113

Reagents: i. EDCl, HOBt, THF, rt 16 h. Preferably R$^1$ and R$^2$ = Me.

In yet another highly preferred embodiment, the compounds of the invention are prepared in accordance with Scheme 6 below.

Scheme 6

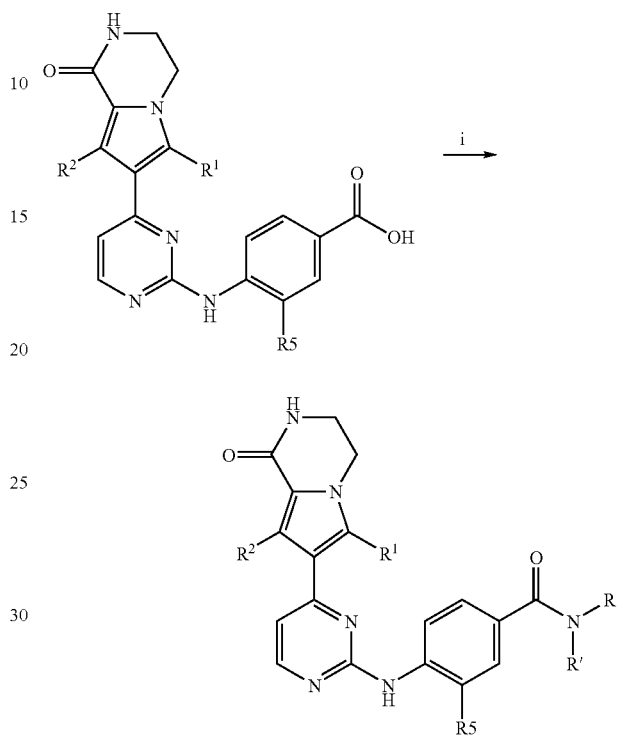

Examples I-114 to I-115

Reagents: i. TBTU, rt. Preferably R$^1$ and R$^2$ = Me.

The skilled person will appreciate that the steps shown in Schemes 4, 5 and 6 can be readily adapted to provide compounds bearing the substituent at other positions on the phenyl ring, compounds bearing additional substituents on the phenyl ring, and compounds with alternative X groups (i.e. for example bicyclic groups).

The present invention is further described by way of example.

EXAMPLES

General

NMR spectra were recorded using a Varian INOVA-500 instrument. Chemical shifts are reported in parts per million relative to internal tetramethylsilane standard. Mass spectra were obtained using a Waters ZQ2000 single quadrupole mass spectrometer with electrospray ionization (ESI). Analytical and preparative RP-HPLC was performed using Vydac 218TP54 (250×4.6 mm) and 218TP1022 (250×22 mm) columns, respectively. Linear gradient elution using H$_2$O/MeCN systems (containing 0.1% CF$_3$COOH) at flow rates of 1 mL/min (analytical) and 9 mL/min (preparative) was performed. Purity was assessed by integration of chromatograms (λ=254 nm). Silica gel (EM Kieselgel 60, 0.040-0.063 mm,

Merck) or ISOLUTE pre-packed columns (Jones Chromatography Ltd. UK) were used for flash chromatography.

7-Acetyl-6,8-dimethyl-3,4-dihydropyrrolo[1,2-a]pyrazin-1(2H)-one [2]

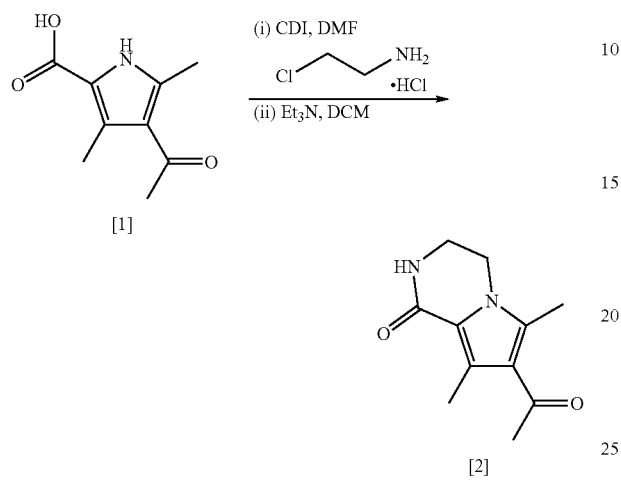

4-Acetyl-3,5-dimethylpyrrole carboxylic acid [1] (3.000 g, 16.55 mmol), was taken up in anhydrous DMF (20 mL) and cooled to 0° C. Carbonyldiimidazole (4.027 g, 24.82 mmol) was added to this slurry and stirred until the evolution of gas ceased and a clear solution formed. 2-Chloroethyl amine hydrochloride (5.760 g, 49.65 mmol) was added in one portion. The reaction mixture was left to stir overnight at room temperature. Removal of the DMF under reduced pressure and the residue extracted into dichloromethane (3×20 mL) from ice/water (10 mL). The organic layers were washed with dilute HCl (5 mL), sat., water (5 mL) and brine (5 mL) before drying over magnesium sulfate and concentrated under vacuum. The residue contained a mixture of target product [2] and uncyclised pyrrole amide (see structures [6] and [2] below), which was carried on to the next step without further purification.

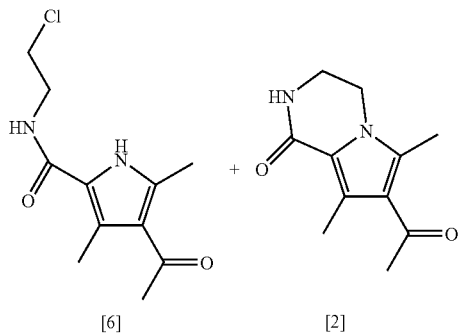 [SMILES: CC(=O)c1c(C)[nH]c(C(=O)NCCCl)c1C ; CC(=O)c1c(C)c2n(c1C)CCNC2=O]

The crude mixture was taken up in dichloromethane (30 mL) and treated with triethylamine (5 mL) and stirred overnight at room temperature. The next day the reaction mixture was washed with water (20 mL) and dried over magnesium sulfate. Concentration under reduced pressure followed by silica column chromatography of the residue gave the target compound (2.52 g, 12.21 mmol, 74%).

$^1$H NMR (d6-DMSO) δ: 2.32 (3H, s, CH$_3$), 2.42 (3H, s, CH$_3$), 2.45 (3H, s, COCH$_3$), 3.86 (2H, t, CH$_2$N, J=9.3), 4.29 (2H, t, CH$_2$NH, J=9.3), 11.61 (1H, s, CONH); C$_{11}$H$_{14}$N$_2$O$_2$ requires 206.24, m/z=206.67; HPLC R$_t$=10.05 min (0-62-20)

7-[(2E)-3-dimetdylamino)prop-2-enoyl]-6,8-dimethyl-3,4-dihydropyrrolo[1,2-a]pyrazin-1(2H)-one [3]

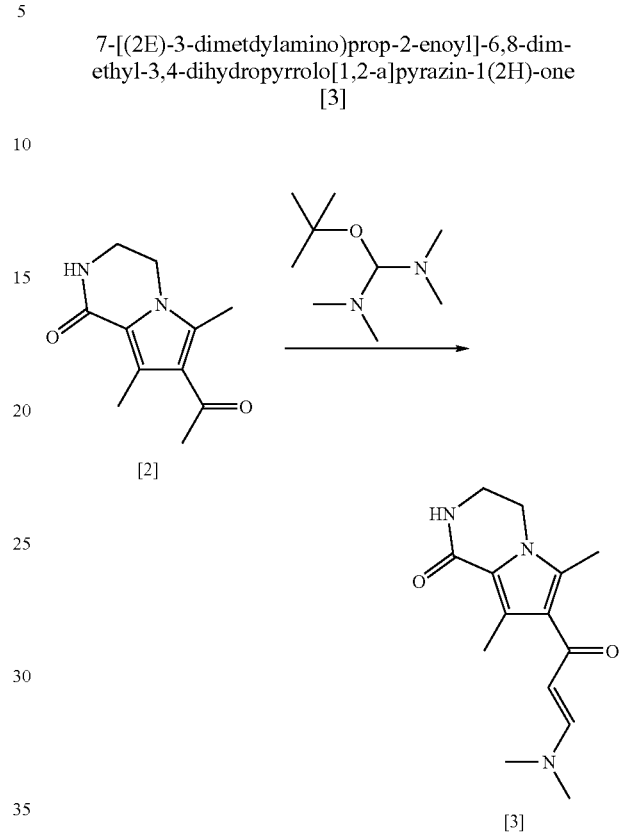

7-Acetyl-6,8-dimethyl-3,4-dihydropyrrolo[1,2-a]pyrazin-1(2H)-one [2] (596 mg, 2.890 mmol) was combined with Brederick's reagent (656 μL, 3.18 mmol) and heated to 95° C. for 8 hours. After cooling the reaction mixture was columned over silica gel to yield the target product [3] (335 mg, 1.282 mmol, 40% yield).

$^1$H NMR (d6-DMSO) δ: 2.29 (3H, s, CH$_3$), 2.30 (3H, s, CH$_3$), 2.94 (6H, broad singlet, N(CH$_3$)$_2$), 3.86 (2H, t, CH$_2$N, J=9.3), 4.27 (2H, t, CH$_2$NH, J=9.3), 5.22 (1H, d, CH=CH, J=12.6), 7.39 (1H, d, CH=CH, J=12.6), 11.23 (1H, s, CONH); C$_{11}$H$_{14}$N$_2$O$_2$ requires 261.32, m/z—261.90; HPLC R$_t$=9.39 min (0-62-20)

Synthesis of Compound [I-2]

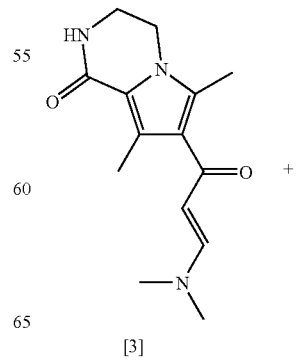

+

-continued

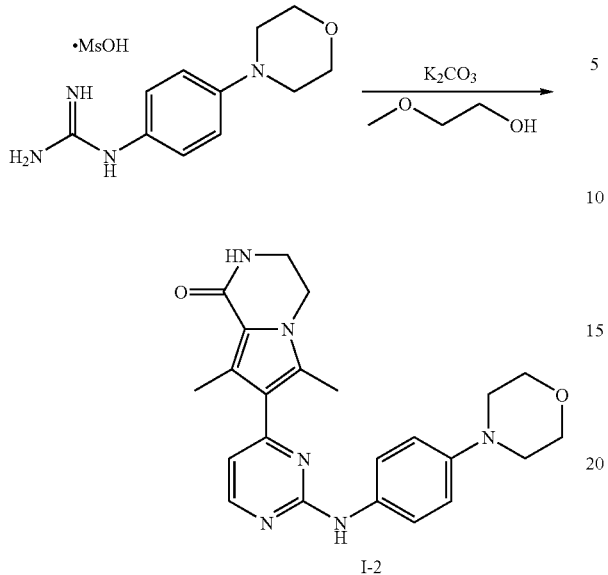

7-[(2E)-3-dimethylamino)prop-2-enoyl]-6,8-dimethyl-3,4-dihydropyrrolo[1,2-a]pyrazin-1-(2H)-one [3] (167 mg, 0.639 mmol), 4-(N-morpholine)-phenyl guanidine methanesulfonic acid (164 mg, 0.639 mmol) and potassium carbonate (89 mg, 0.639 mmol) were combined in 2-methoxy ethanol (4 mL) and heated to 190° C. for a period of 30 minutes in a CEM microwave. After cooling, the inorganics were filtered off and the filtrate concentrated to dryness. This residue was purified on a 10 g SLS pre-packed silica gel column. Pooling of the desired fractions gave the target compound (114 mg, 0.274 mmol, 43% yield).

$^1$H NMR (d6-DMSO) δ: 2.38 (3H, s, CH$_3$), 2.42 (3H, s, CH$_3$), 3.02 (4H, m, CH$_2$NCH$_2$), 3.72 (4H, m, CH$_2$OCH$_2$), 3.89 (2H, t, CH$_2$N, J=9.3), 4.31 (2H, t, CH$_2$NH, J=9.3), 6.71 (1H, d, ArH, J=5.4), 6.87 (2H, d, ArH, J=8.8), 7.60 (2H, d, ArH, J=8.8), 8.31 (1H, d, ArH, J=5.4), 9.11 (1H, s, NH), 11.44 (1H, s, CONH); C$_{23}$H$_{26}$N$_6$O$_2$ requires 418.50, m/z=418.98; HPLC R$_f$=11.92 min (0-62-20).

Compounds I-1 and I-3 were synthesised by an analogous route.

Compound I-1

$^1$H NMR (d$_4$-CD$_3$OD) δ: 2.42 (3H, s, CH$_3$), 2.43 (3H, s, CH$_3$), 3.96 (2H, t, CH$_2$N, J=9.3), 4.40 (2H, t, CH$_2$NH, J=9.3), 6.80 (1H, d, ArH, J=5.4), 7.03 (2H, d, ArH, J=8.2), 7.65 (2H, d, ArH, J=8.2), 8.29 (1H, d, ArH, J=5.4); C$_{19}$H$_{18}$FN$_5$O requires 351.38, m/z=352.03 mz/+1; HPLC R$_f$=12.52 min (0-62-20).

Compound I-3

$^1$H NMR (d6-DMSO) δ: 2.35 (3H, s, CH$_3$), 2.39 (3H, s, CH$_3$), 2.85 (4H, m, CH$_2$NCH$_2$), 3.65 (4H, m, CH$_2$OCH$_2$), 3.70 (3H, s, OCH$_3$), 3.86 (2H, t, CH$_2$N, J=9.3), 4.27 (2H, t, CH$_2$NH, J=9.3), 6.70 (1H, d, ArH, J=5.4), 6.76 (1H, d, ArH, J=8.3), 7.32 (1H, s, ArH), 7.35 (1H, d, ArH, J=8.3), 8.30 (1H, d, ArH, J=5.4), 9.12 (1H, s, NH), 11.42 (1H, s, CONH) C$_{24}$H$_{28}$O$_3$N$_6$ requires 448.52, m/z=449.41 mz/+1; HPLC R$_f$=11.79 min (0-62-20).

Additional Experimental

Preparation of Starting Materials

7-[(2E)-3-dimethylamino)prop-2-enoyl]-6,8-dimethyl-3,4-dihydropyrrolo[1,2-a]pyrazin-1 (2H)-one Step 1

4-Acetyl-3,5-dimethyl-1H-pyrrole-2-carboxylic acid (2-chloro-ethyl)-amide

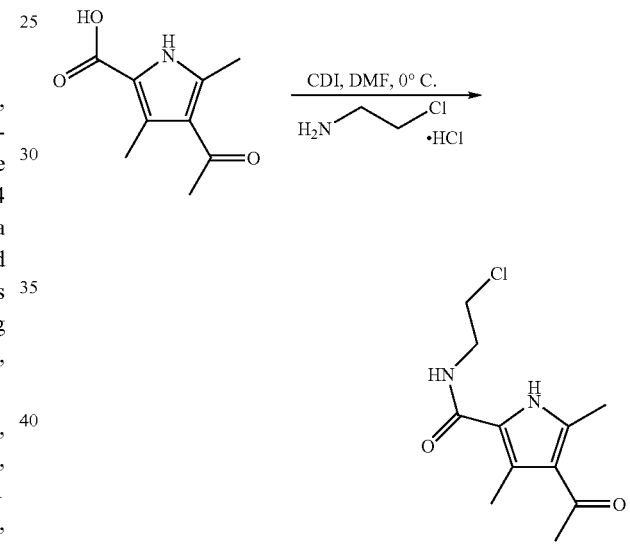

4-Acetyl-3,5-dimethylpyrrole carboxylic acid (15.731 g, 86.82 mmol), was taken up in anhydrous DMF (40 mL) and cooled to 0° C. Carbonyldiimidazole (14.512 g, 86.82 mmol) was added to this slurry and stirred until the evolution of gas ceased and a clear solution formed. 2-Chloroethyl amine hydrochloride (10.574 g, 91.16 mmol) was added in one portion. The reaction mixture was left to stir overnight at room temperature. The reaction mixture was extracted in water (50 mL) from DCM (4×20 mL). The aqueous layer (containing precipitate) was filtered off and washed with cold water. The white solid was found to be the target compound. (10.316 g, 42.51 mmol, 49% yield).

$^1$H NMR (d6-DMSO) δ: 2.32 (3H, s, CH$_3$), 2.42 (3H, s, CH$_3$), 2.45 (3H, s, COCH$_3$), 3.55 (2H, q, CH$_2$N, J=5.8), 3.70 (2H, t, CH$_2$NH, J=5.8), 11.61 (1H, s, CONH); C$_{11}$H$_{14}$N$_2$O$_2$ requires 242.70, m/z=207.56 (M$^+$−Cl); HPLC R$_f$=13.14 min (0-60-20)

Step 2

7-Acetyl-6,8-dimethyl-3,4-dihydro-2H-pyrrolo[1,2-a]pyrazin-1-one

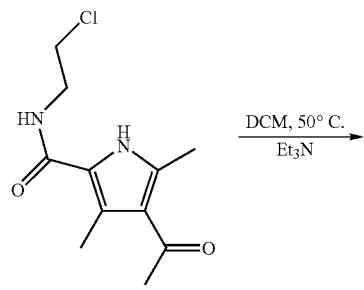

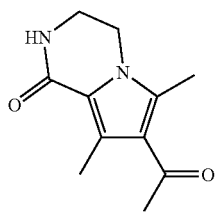

4-Acetyl-3,5-dimethyl-1H-pyrrole-2-carboxylic acid (2-chloro-ethyl)-amide (12.664 g, 52.18 mmol) was slurried in DCM (100 mL) and Et₃N (20 mL) and heated to 50° C. for 16 hours. After cooling to room temperature and removal of solvent, the residue was treated with cold water. The resulting off white precipitate filtered off and shown to be the target compound (10.424 g, 50.54 mmol, 97% yield).

$^1$H NMR (d6-DMSO) δ: 2.32 (3H, s, CH$_3$), 2.42 (3H, s, CH$_3$), 2.45 (3H, s, COCH$_3$), 3.87 (2H, t, CH$_2$N, J=9.3), 4.29 (2H, t, CH$_2$NH, J=9.3), 11.61 (1H, s, CONH); C$_{11}$H$_{14}$N$_2$O$_2$ requires 206.24, m/z=207.14; HPLC R$_t$=9.19 min (0-60-20)

Step 3

7-((E)-3-Dimethylamino-acryloyl)-6,8-dimethyl-3,4-dihydro-2H-pyrrolo[1,2-a]pyrazin-1-one

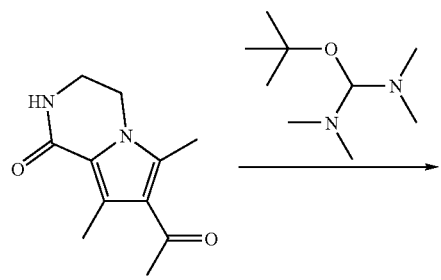

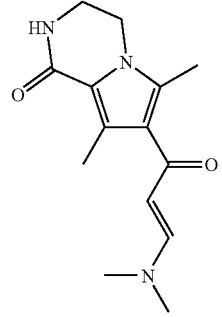

7-Acetyl-6,8-dimethyl-3,4-dihydro-2H-pyrrolo[1,2-a]pyrazin-1-one (6.692 g, 32.49 mmol) was combined with Brederick's reagent (13.42 mL, 64.98 mmol) and heated to 95° C. for 10 hours. After cooling the reaction mixture was treated with acetone (2 mL) and the resulting yellow precipitate filtered off and washed with 2:1 EtOAc:Me$_2$CO to provide the target compound (6.496 g, 24.86 mmol, 77% yield).

$^1$H NMR (d6-DMSO) δ: 2.29 (3H, s, CH$_3$), 2.30 (3H, s, CH$_3$), 2.94 (6H, broad singlet, N(CH$_3$)$_2$), 3.86 (2H, t, CH$_2$N, J=9.3), 4.27 (2H, t, CH$_2$NH, J=9.3), 5.22 (1H, d, CH=CH, J=12.6), 7.39 (1H, d, CH=CH, J=12.6), 11.23 (1H, s, CONH); C$_{11}$H$_{14}$N$_2$O$_2$ requires 261.32, m/z—262.24; HPLC R$_t$=8.77 min (0-60-20)

Preparation of Examples

Method A

Example I-2

6,8-Dimethyl-7-[2-(4-morpholin-4-yl-phenylamino)-pyrimidin-4-yl]-3,4-dihydro-2H-pyrrolo[1,2-a]pyrazin-1-one

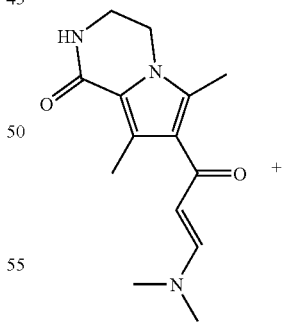

+

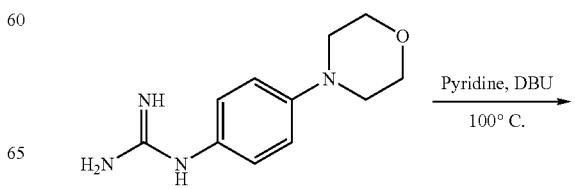

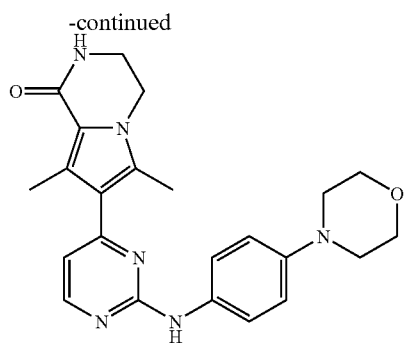

7-((E)-3-Dimethylamino-acryloyl)-6,8-dimethyl-3,4-dihydro-2H-pyrrolo[1,2-a]pyrazin-1-one (6.009 g, 22.99 mmol), 4-(N-morpholine)-phenyl guanidine methanesulfonic acid (7.275 g, 22.99 mmol) and DBU (3.439 mL, 22.99 mmol) were combined in pyridine (60 mL) and heated to 100° C. for a period of 18 hours. After cooling, the reaction mixture was concentrated under reduced pressure and the residue treated with EtOAc containing 30% MeOH. The resulting tan coloured amorphous solid was filtered off and washed (crop1=4.423 g, 10.56 mmol; crop2=0.656 g, 1.56 mmol; Total yield=53%).

$^1$H NMR (d6-DMSO) δ: 2.38 (3H, s, CH$_3$), 2.42 (3H, s, CH$_3$), 3.02 (4H, m, CH$_2$NCH$_2$), 3.72 (4H, m, CH$_2$OCH$_2$), 3.89 (2H, t, CH$_2$N, J=9.3), 4.31 (2H, t, CH$_2$NH, J=9.3), 6.71 (1H, d, ArH, J=5.4), 6.87 (2H, d, ArH, J=8.8), 7.60 (2H, d, ArH, J=8.8), 8.31 (1H, d, ArH, J=5.4), 9.11 (1H, s, NH), 11.44 (1H, s, CONE; C$_{23}$H$_{26}$N$_6$O$_2$ requires 418.49 m/119.98; HPLC R=11.29 min (0-60-20)

The following examples were prepared by Method A as above using the appropriate starting materials:

Example I-1

7-[2-(4-Fluoro-phenylamino)-pyrimidin-4-yl]-6,8-dimethyl-3,4-dihydro-2H-pyrrolo[1,2-a]pyrazin-1-one $^1$H NMR (CD3OD): 2.42 (3H, s, CH3), 2.44 (3H, s, CH3), 3.96 (2H, t, J 9.3, CH2), 4.34 (2H, t, J 9.3, CH2), 6.80 (1H d, 35.0 Hz, pyr-H), 7.01 (2H, dd, J 8.0 Hz, 2×Ar—H), 7.65 (2H, dd, J 8.0, 5.0 Hz, 2×Ar—H), 8.30 (1H, d, J 5.0 Hz, pyr-H); MS (+ve): 352.03; tR=12.52 min (0_60_20)

Example I-3

7-[2-(3-Methoxy-4-morpholin-4-yl-phenylamino)-pyrimidin-4-yl]-6,8-dimethyl-3,4-dihydro-2H-pyrrolo[1,2-a]pyrazin-1-one $^1$H NMR (DMSO): 2.35 (3H, s, CH3), 2.39 (3H, s, CH3), 2.85 (4H, dd, J 4.5 Hz, 2×CH2), 3.66 (4H, dd, J 4.5 Hz, 2×CH2), 3.70 (3H, s, OCH3), 3.85 (2H, t, J 9.0 Hz, CH2), 4.27 (2H, t, J 9.0 Hz, CH2), 6.71 (1H, d, J 5.3, pyr-H), 6.76 (1H, d, J 8.5 Hz, Ar—H), 7.32 (1H, d, J 2.5 Hz, Ar—H), 7.34 (1H, dd, J 8.5, 2.5 Hz, Ar—H), 8.30 (1H, d, J 5.3 pyr-H), 9.12 (1H, s, NH), 11.42 (1H, s, NH); MS (+ve): 449.41; tR=11.79 min (0_60_20).

Example I-4

7-[2-(4-Methoxy-phenylamino)-pyrimidin-4-yl]-6,8-dimethyl-3,4-dihydro-2H-pyrrolo[1,2-a]pyrazin-1-one $^1$H (DMSO): 2.37 (3H, s, CH3), 2.41 (3H, s, CH3), 3.71 (3H, s, OCH3), 3.90 (2H, t, J 9.0 Hz, CH2), 4.32 (2H, t, J 9.0 Hz, CH2), 6.73 (1H, d, J 5.5 Hz, pyr-H), 6.85 (2H, dd, J 7.0, 2.0 Hz, 2×Ar—H), 7.64 (2H, dd, J 7.0, 2.0 Hz, 2×Ar—H), 8.32 (1H, d, J 5.5 Hz, pyr-H), 9.18 (1H, s, NH, 11.48 (1H, s, NH); m/s (+ve) 363.69

Example I-5

6,8-Dimethyl-7-[2-(3-nitro-phenylamino)-pyrimidin-4-yl]-3,4-dihydro-2H-pyrrolo[1,2-a]pyrazin-1-one $^1$H (DMSO): 2.42 (3H, s, CH3), 2.45 (3H, s, CH3), 3.91 (2H, t, J 9.0 Hz, CH2), 4.33 (2H, t, J 9.0 Hz, CH2), 6.93 (1H, d, J 5.0 Hz, pyr-H), 7.55 (1H, dd, J 9.0 Hz, Ar—H), 7.77 (1H, dd, J 9.0, 2.0 Hz, Ar—H), 8.08 (1H, dd, J 9.0, 2.0 Hz, Ar—H), 8.47 (1H, d, J 5.0 Hz, pyr-H), 8.95 (1H, d, J 2.0 Hz, Ar—H), 9.80 (1H, s, NH), 11.57 (1H, s, NH); M/S (+ve) 378.76; HPLC rt=15.22 (0_60_20)

Example I-6

7-[2-(4-Dimethylamino-phenylamino)-pyrimidin-4-yl]-6,8-dimethyl-3,4-dihydro-2H-pyrrolo[1,2-a]pyrazin-1-one M/S (+ve) 377.51

Example I-7

7-{2-[4-(4-Acetyl-piperazin-1-yl)-phenylamino]-pyrimidin-4-yl}-6,8-dimethyl-3,4-dihydro-2H-pyrrolo[1,2-a]pyrazin-1-one $^1$H (DMSO): 2.03 (3H, s, CH3), 2.38 (3H, s, CH3), 2.42 (3H, s, CH3), 2.99 (2H, dd, J 5.5 Hz, CH2), 3.06 (2H, dd, J 5.5 Hz, CH2), 3.56 (4H, dt, J 5.5 Hz, 2×CH2), 3.90 (2H, t, J 9.0 Hz, CH2), 4.31 (2H, t, J 9.0 Hz, CH2), 6.72 (1H, d, J 5.5 Hz, pyr-H), 6.90 (2H, d, J 9.5 Hz, 2×Ar—H), 7.61 (2H, d, J 9.5 Hz, 2×Ar—H), 8.32 (1H, d, J 5.5 Hz, pyr-H), 9.13 (1H, s, NH), 11.45 (1H, s, NH); M/S (+ve) 460.60; HPLC rt-10.41 (0_60_20)

Example I-8

7-{2-[4-(4-Acetyl-piperazin-1-yl)-3-methyl-phenylamino]-pyrimidin-4-yl}-6,8-dimethyl-3,4-dihydro-2H-pyrrolo[1,2-a]pyrazin-1-one $^1$H NMR (DMSO) 2.05 (3H, s, CH3), 2.22 (3H, s, CH3), 2.40 (3H, s, CH3), 2.71 (2H, t, d J=5.4 Hz, CH2), 2.79 (2H, t, J 5.4 Hz, CH2), 3.52 (4H, t, J=5.4 Hz, CH2), 3.89 (4H, t, J=5.4 Hz, CH2), 6.75 (1H, d, J=5.4 Hz, pyrim-H), 6.91 (1H, d, J=8 Hz, aromatic-H), 7.52 (1H, m, aromatic-H), 7.60 (1H, d, J=2.4 Hz, aromatic-H), 8.45 (1H, d, J=5.4 Hz, pyrim-H), 9.17 (1H, s, NH), 11.49 (1H, s, NH).

M/S (+ve) 473.82.

Example I-9

7-{-2-[t(4-Ace-piperazin-1-yl)-3-methoxy-phenylamino]-pyrimidin-4-yl}-6,8-dimethyl-3,4-dihydro-2H-pyrrolo[1,2-a]pyrazin-1-one $^1$H NMR (DMSO) 2.01 (3H, s, CH3), 2.28 (3H, s, CH3), 2.44 (3H, s, CH3), 2.84 (2H, t, J=4.9 Hz, CH2), 2.90 (2H, t, J=4.9 Hz, CH2), 3.54 (4H, t, J=6.84 Hz, CH2), 3.91 (2H, t, J=9.3, CH2), 4.32 (2H, t, J=9.3 Hz, CH2), 6.83 (1H, d, J=5.2 Hz, pyrim-H), 6.91 (1H, d, J=8.3 Hz, aromatic-H), 7.41 (1H, d, J=7.8 Hz, aromatic-H), 7.44 (1H, s, aromatic H), 8.43 (1H, d, J=5.2 Hz, pyrim-H), 9.18 (1H, s, NH), 11.49 (1H, s, NH).

HPLC: at 254 nm, R$_T$=12.02, 100%, M/S (+VE) 489.67

Example I-10

7-{2-[4-((2R,6S)-2,6-Dimethyl-morpholin-4-yl)-phenylamino]-pyrimidin-4-yl}-6,8-dimethyl-3,4-dihydro-2H-pyrrolo[1,2-a]pyrazin-1-one $^1$H NMR (DMSO) 1.10 (3H, s, CH3), 1.12 (3H, s, CH3), 2.23 (3H, s, CH3), 2.38 (3H, s, CH3), 2.42 (3H, s, CH3), 3.72 (2H, m, mozph-H), 3.90 (2H, m, CH2), 4.32 (2H, m, CH2), 6.75 (1H, d, J=5.4 Hz, pyrim-H), 6.92 (1H, d, J=5.4 Hz, pyrim-H), 7.51 (1H, m, aromatic-H), 7.59 (1H, m, aromatic-H), 8.35 (1H, d, J=5.4 Hz, pyrim-H), 9.15 (1H, s, NH), 11.49 (1H, s, NH). HPLC: at 254 nm, RT=15.15, 94.53% (0_60_20) M/S (+ve) 460.89

Example I-11

7-[2-(1H-Indazol-6-ylamino)-pyrimidin-4-yl]-6,8-dimethyl-3,4-dihydro-2H-pyrrolo[1,2-a]pyrazin-1-one $^1$H NMR (DMSO): 2.43 (3H, s, CH3), 2.46 (3H, s, CH3), 3.91 (2H, t, J 9.5 Hz, CH), 4.32 (2H, t, J 9.5 Hz, CH2), 6.83 (1H, d, J 5.5 Hz, pyr-H), 7.29 (1H, d, J 8.5 Hz, Ar—H, 7.56 (1H, d, J 8.5 Hz, Ar—H), 7.89 (1H, s, Ar—H), 8.34 (1H, s, Ar—H), 8.43 (1H, d, J 8.5 Hz, Ar—H), 9.55 (1H, s, NH), 11.51 (1H, s, NH), 12.80 (1H s, NH); tR=12.86 min (0_60_20) M/S (+ve) 373.54

Example I-12

7-[4-(6,8-Dimethyl-1-oxo-1,2,3,4-tetrahydro-pyrrolo[1,2-a]pyrazin-7-yl)-pyrimidin-2-ylamino]-4H-benzo[1,4]oxazin-3-one $^1$H NMR (DMSO): 2.38 (3H, s, CH3), 2.42 (3H, s, CH3), 3.90 (2H, t, J 9.3 Hz, CH2), 4.31 (2H, t, J 9.3 Hz, CH2), 4.52 (2H, s, CH2), 6.77 (1H, d, J 4.8 Hz, pyr-H), 6.78 (1H, d, J 9.0 Hz, Ar—H), 7.26 (1H, dd, J 9.0, 2.5 Hz, Ar—H), 7.60 (1H, d, J 2.5 Hz, Ar—H), 8.35 (1H, d, J 4.8 Hz, pyr-H), 9.33 (1H, s, NH), 10.52 (1H, s, NH), 11.47 (1H, s, NH); tR=12.17 min (0_60_20) MS (+ve) 404.90

Example I-13

7-[2-(4-Diethylamino-phenylamino)-pyrimidin-4-yl]-6,8-dimethyl-3,4-dihydro-2H-pyrrolo[1,2-]pyrazin-1-one M/S(+ve) 405.60; HPLC rt=10.97 (0_60_20)

Example I-13a 6,8-Dimethyl-7-[2-(6-morpholin-4-yl-pyridin-3-ylamino)-pyrimidin-4-yl]-3,4-dihydro-2H-pyrrolo[1,2-a]pyrazin-1-one

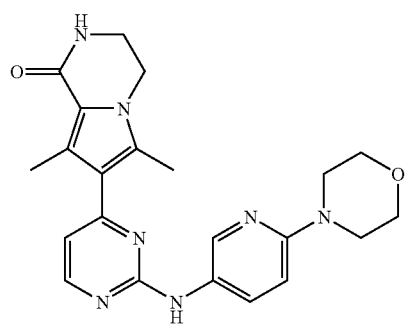 [SMILES: Cc1c(-c2ccnc(Nc3ccc(N4CCOCC4)nc3)n2)c(C)n2c1C(=O)NCC2]

$^1$H NMR (DMSO): 2.36 (3H, s, CH3), 2.40 (3H, s, CH3), 3.34 (2H, dd, J 4.5 Hz, CH2), 3.70 (2H, dd, J 4.5 Hz, CH2), 3.89 (2H, t, J 9.3 Hz, CH2), 4.31 (2H, t, 39.3 Hz, CH2), 6.73 (1H, d, J 5.0, pyrim-H), 6.81 (1H, d, J 9.3 Hz, Ar—H), 7.93 (1H, dd, J 9.3, 2.5 Hz, Ar—H), 8.31 (1H, d, J 5.0, pyrim-H), 8.43 (1, d, J 2.5 Hz, Ar—H), 9.13 (1H, s, NH), 11.45 (1H, s, NH); R$_t$=11.60 min (0_60_20).

Example I-13b

7-[2-(6-Methoxy-pyridin-3-ylamino)-pyrimidin-4-yl]-6,8-dimethyl-3,4-dihydro-2H-pyrrolo[1,2-a]pyrazin-1-one

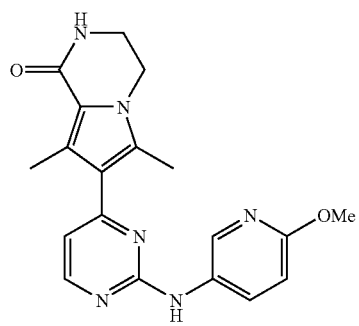 [SMILES: COc1ccc(Nc2nccc(-c3c(C)c4n(c3C)CCNC4=O)n2)cn1]

$^1$H NMR (DMSO): 2.36 (3H, s, CH3), 2.41 (3H, s, CH3), 3.80 (3H, s, OCH3), 3.89 (2H, t, J=9.5 Hz, CH2), 4.31 (2H, t, J=9.5 Hz, CH2), 6.76-6.79 (2H, m incl J=9.0, 5.0, PheH, PyrH), 8.03 (1H, dd, J 9.0, 2.5 Hz, PheH), 8.34 (1H, d, J=5.0 Hz, PyrH), 8.46 (1H, d, J=2.5 Hz, PheH), 9.29 (1H bs, NH), 11.49 (1H, bs, NM. HPLC Rt=10.895 0_60_20 100% Mass=364+ve

Preparation of Intermediates

Synthesis of 7-(2-Amino-pyrimidin-4-yl)-6,8-dimethyl-3,4-dihydro-2H-pyrrolo[1,2-a]-pyrazin-1-one

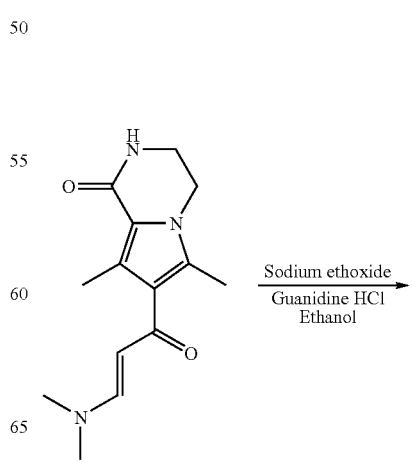

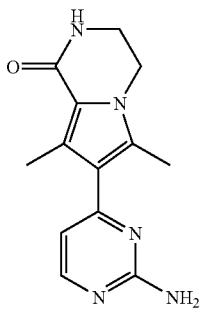

Guanidine hydrochloride (105.3 g) was added to a solution of sodium ethoxide (75.0 g) in ethanol (2660 mL) at room temperature under nitrogen. A solution of 7-((E)-3-(dimethylamino)acryloyl)-3,4-dihydro-6,8-dimethylpyrrolo-1,2-a)pyrazin-1(2H)-one 1 (288 g) in ethanol (3990 mL) was then added and the resulting suspension heated at 77° C. overnight. The solvent was then removed in vacuo and the remaining solid was slurried in water (4000 mL). The crude solid was filtered and the filter cake washed with water (4×1000 mL), diethyl ether (2×1000 mL) and pulled dry. The crude product was then slurried in ethanol (900 mL), filtered, washed with ethanol (2×400 mL), diethyl ether (3×400 mL) and pulled dry. Further drying in a vacuum oven at 45° C. yielded the title compound as an off-white solid (228.6 g, 80%).

$^1$H NMR (DMSO): δ 2.37 (s, 3H), 2.40 (s, 3H), 3.88 (t, 2H, J=9.2 Hz), 4.30 (t, 2H, J=9.2 Hz), 6.32 (2H, s, —NH$_2$), 6.54 (d, 1H, J=5.3 Hz), 8.14 (d, 1H, J=5.3 Hz), 11.35 (bs, 1H). MS (+ve) 258.

Preparation of 7-(2-Fluoro-pyrimidin-4-yl)-6,8-dimethyl-3,4-dihydro-2H-pyrrolo [1,2-a]pyrazin-1-one

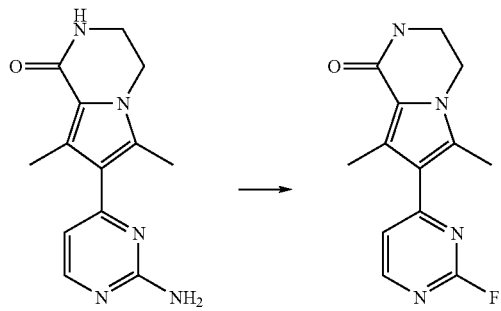 [SMILES: Cc1c(-c2ccnc(N)n2)c(C)n2c1C(=O)NCC2 ; Cc1c(-c2ccnc(F)n2)c(C)n2c1C(=O)NCC2]

60% HF/Pyridine solution was prepared by the careful, dropwise addition of pyridine (28.8 ml, 0.354M) to 70% HF/pyridine (150 ml, 5.76M) under nitrogen in a PFA flask, keeping the internal temperature<−25° C. 7-(2-Aminopyrimidin-4-yl)-6,8-dimethyl-3,4-dihydro-2H-pyrrolo[1,2-a] pyrazin-1-one (32.4 g, 0.126M) was added in small portions, keeping the internal temperature<−25° C. The cooling bath was removed and the mixture's temperature was allowed to warm to ca. −10° C., by which time a homogeneous solution was obtained. The flask was immersed in an ice-acetone bath and tert-butyl nitrite (21.6 ml, 90% w/w, 0.164M) added dropwise over a period of 45 min, keeping the internal temperature<−5° C. A gentle evolution of gas and a mild exotherm was observed. The cooling bath was removed and the reaction mixture stirred a further 1.5 h. The mixture was poured into ice-water (1.5 L) and the mixture basified by addition of solid K$_2$CO$_3$ (~400 g). The mixture was extracted with ethyl acetate (3×1 L). The combined organics were washed with brine (2×500 ml), dried (MgSO$_4$), filtered and evaporated to a pale yellowish solid. Dried under vacuum at 40° C. 30.3 g (92%) obtained. NMR (DMSO): δ 2.45 (s, 3H), 2.49 (s, 3H), 3.91 (t, 2H, J=9.3 Hz), 4.33 (t, 2H, J=9.3 Hz), 7.47 (t, 1H, J=4.9 Hz), 8.62 (dd, 1H, J=5.4 Hz, 2.4 Hz), 11.75 (bs, 1H). IR (ATR): ν$_{co}$str 1633 cm$^{-1}$.

Preparation of 7-(2-Fluoro-pyrimidin-4-yl)-2,6,8-trimethyl-3,4-dihydro-2H-pyrrolo[1,2-a]pyrazin-1-one

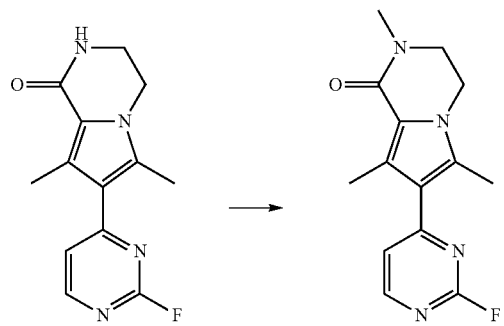 [SMILES: Cc1c(-c2ccnc(F)n2)c(C)n2c1C(=O)NCC2 ; Cc1c(-c2ccnc(F)n2)c(C)n2c1C(=O)N(C)CC2]

7-(2-Fluoropyrimidin-4-yl)-6,8-dimethyl-3,4-dihydro-2H-pyrrolo[1,2-a]pyrazin-1-one (250 mg, 0.96 mmol) was dissolved in DMF (5 ml) and cooled in an ice-acetone bath. NaH (95% w/w, 27 mg, 1.06 mmol) was added in three portions, producing a precipitate and an evolution of gas. The mixture was stirred with cooling for 20 min, during which time the precipitate dissolved. Iodomethane (66 μl, 1.06 mmol) was added and the mixture stirred with cooling. After 1 h the cooling bath was removed and the mixture stirred a further hour. Tlc (EtOAc×2) shows no starting material remaining. The reaction mixture (now an orange suspension) was evaporated. The solid residue was treated with sat NaHCO$_3$ (10 ml) and water (20 ml) and extracted with EtOAc (3×25 ml). The combined organics were washed (brine), dried (MgSO$_4$), filtered and evaporated to give the product as a light amber solid. 241 mg (92%) obtained. NMR (DMSO) δ 2.38 (s, 3H), 2.40 (s, 3H), 3.79 (d, 3H, J=3.4 Hz), 3.91-3.95 (m, 2H), 4.29-4.33 (m, 2H), 7.46 (m, 1H), 8.67 (m, 1H). IR (ATP): ν$_{co}$str 1643 cm$^{-1}$.

In a similar manner 2-Ethyl-7-(2-fluoro-pyrimidin-4-yl)-6,8-dimethyl-3,4-dihydro-2H-pyrrolo[1,2-a]pyrazin-1-one was prepared using ethyl iodide as the alkylating agent.

Method B

General method for coupling of fluoropyrimidines with anilines, (see Whitfield, H. et al, Chem. Commun., 2003, 2802-2803):

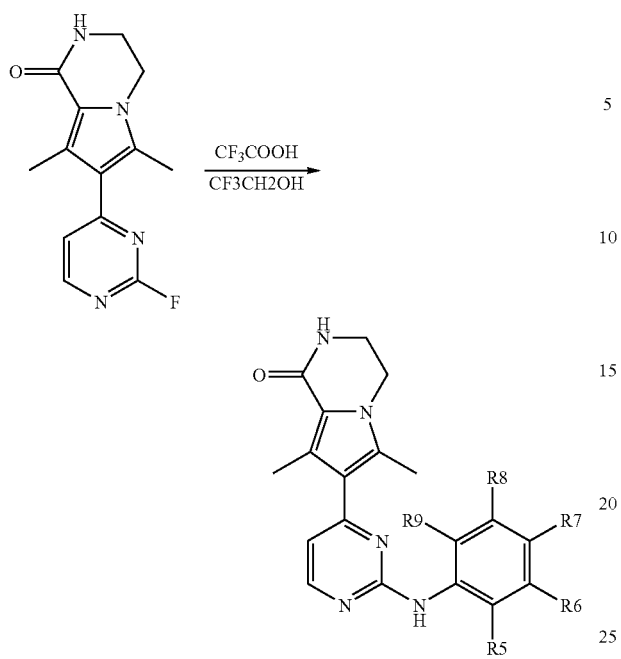

7-(2-Fluoropyrimidin-4-yl)-6,8-dimethyl-3,4-dihydropyrrolo[1,2-a]pyrazin-1(2H)-one (1 eq), the appropriate aniline (1-3.6 eq) and trifluoroacetic acid (5 eq) were added to 5-10 mL of trifluoroethanol in a round-bottomed flask and the resulting mixture heated to reflux for 4-12 h. The progress of the reaction was monitored by HPLC and when no starting material remained the reaction mixture was cooled, evaporated under reduced pressure and the residue purified by column chromatography (product eluted by 10:1 EtOAc/MeOH). The fractions containing the product were combined, evaporated under reduced pressure and then further dried in vacuo. The product was collected by suction filtration using MeOH (1-2 mL), washed with $Et_2O$ (5 mL) and dried in a dessicator.

If necessary compounds were purified by flash chromatography or RP-preparative HPLC.

Method B

The following compounds were prepared by reaction of 7-(2-fluoropyrimidin-4-yl)-6,8-dimethyl-3,4-dihydro-2H-pyrrolo[1,2-a]pyrazin-1-one with an the appropriate aniline

Example I-14

7-[2-(4-Bromo-phenylamino)-pyrimidin-4-yl]-6,8-dimethyl-3,4-dihydro-2H-pyrrolo[1,2-a]pyrazin-1-one m/e 412.42, 414.46 (MH+ isotopes); HPLC R.T. 14.40 mins (10-70-20)

Example I-15

7-{2-[3-(2-Hydroxy-ethanesulfonyl)-phenylamino]-pyrimidin-4-yl}-6,8-dimethyl-3,4-dihydro-2H-pyrrolo[1,2-a]pyrazin-1-one $^1$H NMR (DMSO): 2.41 (3H, s, CH3), 2.44 (3H, s, CH3), 3.38 (2H, t, J 6.5 Hz, CH2), 3.67 (2H, m, incl J 6.5, 5.5 Hz, CH2OH), 3.90 (2H, t, J 9.0 Hz, —CH2N—), 4.30 (2H, t, J 9.0 Hz, —CH2N—), 4.87 (1H, t, J 5.5 Hz, OH), 6.89 (1H, d, J 5.5 Hz, pyrimidine H), 7.41 (1H, dd, J 8.0, 1.0 Hz, aryl-H), 7.53 (1H, dd, J 8.0 Hz, aryl-H), 8.10 (1H, dd, J 8.0, 1.0 Hz, aryl-H), 8.40 (1H, s, aryl-H), 8.44 (1H, d, J 5.5 Hz, pyrimidine H), 9.80 (1H, s, NH), 11.52 (1H, s, CONH); MS (+ve): 442.31; tR=10.69 min (10__70__20)

Example I-16

5-[4-(6,8-Dimethyl-1-oxo-1,2,3,4-tetrahydro-pyrrolo[1,2-a]pyrazin-7-yl)-pyrimidin-2-ylamino]-benzo[b]thiophene-2-carboxylic acid $^1$H NMR (DMSO): 2.74 (s, 6H, 2×CH3), 4.33 (t, J=9.5 Hz, 2H, CH2), 5.13 (t, J=9.5 Hz, 2H, CH2), 7.16 (d, J=5 Hz, 1H, pyr-H), 8.03 (d, J=9 Hz, 1H, phe-H), 8.17 (d, J=9 Hz, 1H, phe-H), 8.24 (s, 1H, thio-H), 8.76 (d, J=5 Hz, 1H, pyr-H), 8.77 (s, 1H, phe-H); MS (+ve): 434.49;

Example I-17

7-[2-(4-Hydroxy-phenylamino)-pyrimidin-4-yl]-6,8-dimethyl-3,4-dihydro-2H-pyrrolo[1,2-a]pyrazin-1-one $^1$H NMR (CD3OD): 2.55 (S, 3H, CH3), 2.56 (s, 3H, CH3), 4.21 (t, J±9.5 Hz, 2H, CH2), 5.06 (t, J=9.5 Hz, 2H, CH2), 6.87 (d, J=9 Hz, 2H, phe-H), 7.06 (d, J=6.5 Hz, 1H, pyr-H), 7.32 (d, J=9 Hz, 2H, phe-H), 8.24 (d, J=6.5 Hz, 1H, pyr-H); MS (+ve): 350.52; tR=9.40 min (0__60__20)

Example I-18

4-[4-(6,8-Dimethyl-1-oxo-1,2,3,4-tetrahydro-pyrrolo[1,2-a]pyrazin-7-yl)-pyrimidin-2-ylamino]-N-isopropyl-2-methoxy-benzenesulfonamide $^1$H NMR (DMSO): 1.01 (s, 3H, CH3), 1.02 (s, 3H, CH3), 2.57 (s, 6H, 2×CH3), 325 (bs, 1H, CM), 3.91 (s, 3H, OCH3), 4.16 (t, J=9 Hz, 2H, CH2), 4.99 (t, J=9 Hz, 2H, CH2), 6.96 (d, J=8.5 Hz, 1H phe-H), 7.66-7.70 (m, 3H, 2×phe-H and 1×NH), 8.62 (d, J=5 Hz, 1H, pyr-H); MS (+ve): 485.48; tR=14.74 min (0__60__20)

Example I-19

4-[4-(6,8-Dimethyl-1-oxo-1,2,3,4-tetrahydro-pyrrolo[1,2-a]pyrazin-7-yl)-pyrimidin-2-ylamino]-N-isopropyl-benzenesulfonamide $^1$H NMR (DMSO): 0.89-0.92 (m, 6H, 2×CH3), 2.40 (s, 6H, 2×CH3), 3.01 (m, 1H, CH), 4.08 (t, J=9 Hz, 2H CH2), 4.94 (t, J=9 Hz, 2H, CH2), 6.96 (d, J=5 Hz, 1H, pyr-H), 7.32 (d, J=6 Hz, 1H, NH), 7.66 (d, J=9 Hz, 2H, phe-H), 7.92 (d, J=9 Hz, 2H, phe-H), 8.53 (d, J=5 Hz, 1H, pyr-H); MS (+ve): 455.55; tR=1436 min (0__60__20).

Example I-20

N-{4-[4-(6,8-Dimethyl-1-oxo-1,2,3,4-tetrahydro-pyrrolo[1,2-a]pyrazin-7-yl)-pyrimidin-2-ylamino]-phenyl}-methanesulfonamide $^1$H NMR (DMSO): 2.48 (s, 6H, 2×CH3), 2.93 (S, 3H, CH3), 4.17 (t, J=9.5 Hz, 2H, CH2), 5.02 (t, J=9.5 Hz, 2H, CH2), 6.82 (d, J=5 Hz, 1H, pyr-H), 7.19 (d, J=9 Hz, 2H, phe-H), 7.62 (d, J=9 Hz, 2H, phe-H), 8.38 (d, J=5 Hz, 1H, pyr-H); MS (+ve): 427.52; tR=10.72 min (0__60__20).

Example I-21

N-(3-Diethylamino-propyl)-4-[4-(6,8-dimethyl-1-oxo-1,2,3,4-tetrahydro-pyrrolo[1,2-a]pyrazin-7-ylo-pyrimidin-2-ylamino]-2-methyl-benzenesulfonamide $^1$H NMR (CD3OD): 1.30 (t, J=7.5 Hz, 6H, 2×CH2CH3), 1.86-1.89 (m, 2H, CH2), 2.55 (s, 3H, CH3), 2.56 (s, 3H, CH3), 3.02 (dd, J=6.5 Hz, 2H, CH2), 3.15-3.20 (m, 6H, CH2 and 2×CH2CH3), 4.21 (dd, J=9.5 Hz, 2H, CH2), 5.07 (dd, J=9.5 Hz, 2H, CH2), 6.92 (d, J 5 Hz, 1H, pyr-H), 7.34 (d, J=8 Hz, 1H, phe-H), 7.82 (dd, J=2.5 and 8 Hz, 1H, phe-H), 8.44 (d, J=2.5 Hz, 1H, phe-H), 8.49 (d, J=5 Hz, 1H, phe-H); MS (+ve): 540.50; tR=11.56 min (0__60__20).

Example I-22

7-{2-[3-Methoxy-4-(piperidine-1-sulfonyl)-phenylamino]-pyrimidin-4-yl}-6,8-dimethyl-3,4-dihydro-2H-pyrrolo[1,2-a]pyrazin-1-one $^1$H NMR (CD3OD): 1.52-1.41 (m, 2H, piperid-H), 1.59-1.63 (m, 4H, piperid-H), 2.55 (s, 3H, CH3), 2.56 (s, 3H, CH3), 3.15 (dd, J=5.5 Hz, 4H, piperid-H), 3.91 (s, 3H, OCH3), 4.21 (dd, J=9.5 Hz, 2H, CH2), 5.07 (dd, J=9.5 Hz, 2H, CH2), 6.98 (d, J=5 Hz, 1H, pyr-H), 7.50 (dd, J=2 and 8.5 Hz, 1H, phe-H), 7.69 (d, J=9 Hz, 1H, phe-H), 7.72 (d, J=2 Hz, 1H, phe-H), 8.56 (d, J=5 Hz, 1H, pyr-H); tR=16.31 min (0__60__20); MS (+ve)

Example I-23

N-(2-Dimethylamino-ethyl)-4-[4-(6,8-dimethyl-1-oxo-1,2,3,4-tetrahydro-pyrrolo[1,2-a]pyrazin-7-yl)-pyrimidin-2-ylamino]-2-methoxy-benzenesulfonamide $^1$H NMR (CD3OD): 2.55 (s, 3H, CH3), 2.56 (s, 3H, CH3), 2.95 (s, 6H, 2×NCH3), 3.17-3.20 (m, 2H, CH2), 3.28-3.29 (m, 2H, CH2), 3.98 (s, 3H, OCH3), 4.20 (dd, J=9.5 Hz, 2H, CH2), 5.07 (dd, J=9.5 Hz, 2H, CH2), 7.00 (d, J=5.5 Hz, 1H, pyr-H), 7.52 (dd, J=2 and 9 Hz, 1H, phe-H), 7.75 (d, J=9 Hz, 1H, phe-H), 7.79 (d, J=2 Hz, 1H, phe-H), 8.55 (d, J=5 Hz, 1H, pyr-H); tR=11.08 min (0__60__20); MS (+ve): 514.39.

Example I-24

7-{2-[3-Methoxy-4-(4-methyl-piperazine-1-sulfonyl)-phenylamino]-pyrimidin-4-yl}-6,8-dimethyl-3,4-dihydro-2H-pyrrolo[1,2-a]pyrazin-1-one $^1$H NMR (CD3OD): 2.54 (s, 3H, CH3), 2.56 (s, 3H, CH3), 2.93 (s, 3H, CH3), 3.05 (bs, 2H, piperid-H), 3.16 (bs, 2H, piperid-H), 3.58 (bs, 2H, piperid-H), 3.94 (s, 3H, CH3), 3.98 (bs, 2H, piperid-H), 4.21 (dd, J=9.5 Hz, 2H, CH2), 5.07 (dd, J=9.5 Hz, 2H, CH2), 7.00 (d, J=5 Hz, 1H, pyr-H), 7.52 (dd, J=2 and 8.5 Hz, 1H, phe-H), 7.74 (d, J=8.5 Hz, 1H, phe-H), 7.79 (d, J=2 Hz, 1H, phe-H), 8.55 (d, J=5 Hz, 1H, pyr-H); tR=11.62 min (0__60__20); MS (+ve): 524.20.

Example I-25

[4-(6,8-Dimethyl-1-oxo-1,2,3,4-tetrahydro-pyrrolo[1,2-a]pyrazin-7-yl)-pyrimidin-2-ylamino]-benzoic acid $^1$H NMR DMSO): 2.77 (s, 3H, CH3), 2.80 (s, 3H, CH3), 4.32 (t, J=9.5 Hz, 2H, CH2), 5.06 (t, J=9 Hz, 2H, CH2), 7.20 (d, J=5 Hz, 1H, pyr-H), 7.69 (t, J=8 Hz, 1H, phe-H), 7.82 (d, J=7.5 Hz, 1H, phe-H), 8.27 (d, J=8 Hz, 1H, phe-H), 8.77-8.78 (m, 2H, phe-H and pyr-H); tR=11.8 min (0__60__20).

Example I-26

4-[4-(6,8-Dimethyl-1-oxo-1,2,3,4-tetrahydro-pyrrolo[1,2-a]pyrazin-7-yl)-pyrimidin-2-ylamino]-benzoic acid $^1$H NMR DMSO): 2.53 (s, 3H, CH3), 2.55 (s, 3H, CH3), 4.11 (t, J=9.5 Hz, 2H, CH2), 4.86 (t, J=9.5 Hz, 2H, phe-H), 7.02 (d, J=5 Hz, 1H, pyr-H), 7.91 (d, J=9 Hz, 2H, phe-H), 7.96 (d, J=9 Hz, 2H, phe-1), 8.58 (d, J=5 Hz, 1H, pyr-H);

Example I-27

4-[4-(6,8-Dimethyl-1-oxo-1,2,3,4-tetrahydro-pyrrolo[1,2-a]pyrazin-7-yl)-pyrimidin-2-ylamino]-3-methoxy-benzoic acid $^1$H NMR DMSO: 2.46 (s, 3H, CH3), 2.50 (s, 3H, CH3), 3.94 (s, 3H, OMe), 4.05 (t, J=8 Hz, 2H, CH2), 4.79 (t, J=8 Hz, 2H, CH2), 7.00 (bs, 1H, pyr-H), 7.52 (s, 1H, phe-H), 7.59 (d, J=7.5 Hz, 1H, phe-H), 8.21 (s, 1H, NH, 8.45 (d, J=7.5 Hz, 1H, phe-H), 8.53 (bs, 1H, pyr-H); tR=12.97 min (0__60__20); MS (+ve): 408.51.

Example I-28

7-[2-(3-Hydroxy-4-methoxy-phenylamino)-pyrimidin-4-yl]-6,8-dimethyl-3,4-dihydro-2H-pyrrolo[1,2-a]pyrazin-1-one $^1$H NMR DMSO: 2.46 (s, 3H, CH3), 2.47 (s, 3H, CH3), 3.73 (s, 3H, OMe), 4.10 (t, J=9.5 Hz, 2H, CH2), 4.95 (t, J=9.5 Hz, 2H, CH2), 6.82-9.84 (m, 2H, phe-H and pyr-H), 7.07 (d, J=9 Hz, 1H, phe-H), 7.25 (s, 1H, phe-H), 8.42 (d, J=5 Hz, 1H, pyr-H), 8.39 (bs, 1H, NH); tR=10.30 min (0__60__20); MS (+ve): 380.54.

Example I-29

7-[2-(Benzo-[1,3]dioxol-5-ylamino)-pyrimidin-4-yl]-6,8-dimethyl-3,4-dihydro-2H-pyrrolo[1,2-a]pyrazin-1-one $^1$H NMR DMSO: 2.44 (s, 3H, CH3), 2.45 (s, 3H, CH3), 4.05 (t, J=9 Hz, 2H, CH2), 4.80 (t, I=9 Hz, 2H, CH2), 5.96 (s, 2H, OCH2O), 6.82-6.84 (m, 2H, phe-H and pyr-H), 7.11 (d, J=8 Hz, 1H, phe-E, 7.49 (s; 1H, phe-H), 8.42 (d, J=5 Hz, 1H, py-H); tR=11.61 min (0__60__20); MS (+ve): 378.50

Example I-30

6,8-Dimethyl-7-[2-(3-trifluoromethox-phenylamino)-primidin-4-yl]-3,4-dihydro-2H-1-pyrrolo[1,2-a]pyrazin-1-one $^1$H NMR DMSO: 1.56-1.57 (m, 2H, piperid-H), 1.67-1.72 (m, 4H, piperid-H), 2.47 (s, 3H, CH3), 2.81 (t, J=5 Hz, 4H, piperid-H), 4.04 (t, J=9 Hz, 2H, CH2), 4.76 (t, J=9 Hz, 2H, CH2), 6.94 (d, J=5.5 Hz, 1H, pyr-H), 6.98 (t, J=7.5 Hz, 1H, phe-H), 7.10 (t, J=8 Hz, 1H, phe-H), 7.20 (d, J=7 Hz, 1H, phe-H), 8.35 (d, J=8 Hz, 1H, phe-H), 8.41 (bs, 1H, NH), 8.82 (d, J=5 Hz, 1H, pyr-H); tR=11.38 min (0__60__20); MS (+ve): 417.60.

Example I-31

7-[2-(3-Hydroxy-phenylamino)-pyrimidin-4-yl]-6,8-dimethyl-3,4-dihydro-2H-pyrrolo[1,2-a]pyrazin-1-one $^1$H NMR DMSO: 2.47 (s, 6H, 2×NCH3), 4.08 (t, J=9.5 Hz, 2H, CH2), 4.89 (t, I=9.5 Hz, 2H, CH2), 6.36 (d, J=8 Hz, 1H, phe-H), 6.86 (d, J=5 Hz, 1H, pyr-H), 7.03 (dd, J=8 Hz, 1H, phe-H), 7.14 (d, J=8 Hz, 1H, phe-H), 7.32 (s, 1H, phe-H), 8.46 (d, J=5 Hz, 1H, pyr-H), 9.42 (bs, 1H, NH); tR=10.34 min (0__60__20); MS (+ve): 350.52.

Example I-32

7-[2-(3-Methanesulfonyl-phenylamino)-pyrimidin-4-yl]-6,8-dimethyl-3,4-dihydro-2H-pyrrolo[1,2-a]pyrazin-1-one $^1$H NMR DMSO: 2.48 (s, 3H, CH3), 2.51 (s, 3H, CH3), 3.17 (s, 3H, SO$_2$CH3), 4.10 (t, J 9.5 Hz, 2H, CH2), 4.97 (t, J=9 Hz, 2H, CH2), 6.98 (d, J=5 Hz, 1H, pyr-H), 7.48 (d, J=8 Hz, 1H, phe-H), 7.56 (t, J=8 Hz, 1H, phe-H), 8.02 (d, J=8 Hz, 1H, phe-H), 8.50 (s, 1H, phe-H), 8.55 (d, J=5 Hz, 1H, pyr-H); tR=12.26 min (0__60__20); MS (+ve): 412.49.

Example I-33

7-[2-(4-Methanesulfonyl-phenylamino)-pyrimidin-4-yl]-6,8-dimethyl-3,4-dihydro-2H-pyrrolo[1,2-a]pyrazin-1-one $^1$H NMR DMSO: 2.36 (s, 3H, CH3), 3.01 (s, 3H, CH3), 3.96 (t, J=9.5 Hz, 2H, CH2), 4.81 (t, J=9 Hz, 2H, CH2), 6.90 (d, J=5 Hz, 1H, pyr-H), 7.68 (d, J=9 Hz, 2H, phe-H), 7.91 (d, J=9 Hz, 2H, phe-H), 8.44 (d, J=5 Hz, 1H, pyr-H); tR=12.69 min (0__60-20); MS (+ve): 412.49.

Example I-34

3-{3-[4-(6,8-Dimethyl-1-oxo-1,2,3,4-tetrahydro-pyrrolo[1,2-a]pyrazin-7-yl)-pyrimidin-2-ylamino]-phenyl}-propionic acid $^1$H NMR DMSO: 2.47 (s, 6H, 2×CH3), 2.51-2.53 (m, 2H, CH2), 2.78 (t, J=7.5 Hz, 2H, CH2), 4.05 (t, J=9.5 Hz, 2H, CH2), 4.80 (t, J=9.5 Hz, 2H, CH2), 6.82 (d, J=7.5 Hz, 1H, phe-H), 6.86 (d, J=5 Hz, 1H, pyr-H), 7.18 (dd, J=8 Hz, 1H, phe-H), 7.60-7.63 (m, 2H, phe-H), 8.46 (d, J=5 Hz, 1H, pyr-H), 9.45 (s, 1H, NH); tR=11.40 min (0__60__20); MS (+ve): 406.54.

Example I-35

8-Dimethyl-7-{2-[3-(morpholine-4-sulfonyl)-phenylamino]-pyrimidin-4-yl}-3,4-dihydro-2H-pyrrolo[1,2-a]pyrazin-1-one $^1$H NMR DMSO: 2.50 (s, 3H, CH3), 2.52 (s, 3H, CH3), 2.89 (t, J=4.5 Hz, 4H, morph-H), 3.63 (t, J=4.5 Hz, 4H, morph-H), 4.12 (t, J=19.5 Hz, 2H, Ch2), 4.93 (t, J=9.5 Hz, 2H, CH2), 7.01 (d, J=5 Hz, 1H, pyr-H), 7.32 (d, J=8 Hz, 1H, phe-H), 7.60 (dd, J=8 Hz, 1H, ph-H), 8.09 (d, J=8 Hz, 1H, phe-H), 8.33 (s, 1H, phe-H), 8.58 (d, J=5 Hz, 1H, pyr-H); tR=13.75 min (0__60__20); MS (+ve): 483.54.

Example I-36

6,8-Dimethyl-7-{2-[4-methyl-3-(morpholine-4-sulfonyl)-phenylamino]-pyrimidin-4-yl}-3,4-dihydro-2H-pyrrolo[1,2-a]pyrazin-1-one $^1$H NMR DMSO: 2.61 (s, 3H, CH3), 2.63 (s, 3H, CH3), 2.66 (s, 3H, CH3), 3.18 (t, J=4.5 Hz, 4H, morph-H), 3.75 (t, J=4.5 Hz, 4H, morph-H), 4.25 (t, J=9.5 Hz, 2H, CH2), 5.08 (t, J=9.5 Hz, 2H, CH2), 7.09 (d, J=5 Hz, 1H, pyr-H), 7.51 (d, J=8.5 Hz, 1H, phe-H), 8.11 (d, J=8 Hz, 1H, phe-H), 8.45 (s, 1H, phe-H), 8.67 (d, J=5 Hz, 1H, pyr-H); tR=14.15 min (0__60__20) min; MS (+ve): 497A6

Example I-37

6,8-Dimethyl-7-[2-(4-thiomorpholin-4-yl-phenylamino)-pyrimidin-4-yl]-3,4-dihydro-2H-pyrrolo[1,2-a]pyrazin-1-one $^1$H NMR DMSO: 2.44 (s, 3H, CH3), 2.45 (s, 3H, CH3), 2.70 (t J 4.5 Hz, 4H, thiomorph-H), 3.41 (t, J=4.5 Hz, 4H, thiomorph-H), 4.03 (t, J=9.5 Hz, 2H, CH2), 4.74 (t, J=9.5 Hz, 2H, CH2), 6.79 (d, J=5 Hz, 1H, pyr-H), 6.91 (d, J=8.5 Hz, 2H, phe-H), 7.60 (d, J=8.5 Hz, 2H, phe-H), 8.39 (d, J=5 Hz, 1H, pyr-H), 9.30 (bs, 1H, NH); tR=10.99 min (0__60__20); MS (+ve): 435.52.

Example I-38

4-[4-(6,8-Dimethyl-1-oxo-1,2,3,4-tetrahydro-pyrrolo[1,2-a]pyrazin-7-yl)-pyrimidin-2-ylamino]-N-(2-methoxy-ethyl)-benzenesulfonamide $^1$H NMR CD3OD: 2.54 (s, 3H, CH3), 2.55 (s, 3H, CH3), 3.04 (t, J=5.5 Hz, 2H, CH2), 3.27 (s, 3H, OCH3), 3.39 (t, J=5.5 Hz, 2H, CH2), 4.21 (t, J=9.5 Hz, 2H, CH2), 5.07 (t, J=9.5 Hz, 2H, CH2), 6.98 (d, J=5 Hz, 1H, pyr-H), 7.77 (d, J=9 Hz, 2H, phe-H), 7.95 (d, J=9 Hz, 2H, CH2), 8.53 (d, J=5 Hz, 1H, pyr-H); tR=12.93 min (0__60__20); MS (+ve): 471.47.

Example I-39

6,8-Dimethyl-7-(2-p-tolylamino-pyrimidin-4-yl)-3,4-dihydro-2H-pyrrolo[1,2-a]pyrazin-1-one $^1$H NMR DMSO: 2.46 (s, 3H, CH3), 2.47 (s, 3H, CH3), 4.09 (t, J=9.5 Hz, 2H, CH2), 4.94 (t, J=9.5 Hz, 2H, CH2), 6.85 (d, J=5 Hz, 1H, pyr-H), 7.08 (d, J=8.5 Hz, 2H, phe-H), 7.62 (d, J=8.5 Hz, 2H, phe-H), 8.45 (d, J=5 Hz, 1H, pyr-H), 9.47 (bs, 1H, NH); tR=12.80 min (0__60__20); MS (+ve): 348.50.

Example I-40

2-{4-[4-(6,8-Dimethyl-1-oxo-1,2,3,4-tetrahydro-pyrrolo[1,2-a]pyrazin-7-yl)-pyrimidin-2-ylamino]-phenyl}-propionic acid $^1$H NMR CD3OD: 1.46 (d, J=7 Hz, 3H, CH2CH3), 2.51 (s, 3H, CH3), 2.53 (s, 3H, CH3), 3.69 (q, J=7 Hz, 2H, CH2CH3), 4.17 (t, J=9.5 Hz, 2H, CH2), 4.97 (t, J=9.5 Hz, 2H, CH2), 6.84

(d, J=5 Hz, 1H, pyr-H), 7.26 (d, J=9 Hz, 2H, phe-H), 7.65 (d, J=9 Hz, 2H, phe-H), 8.41 (d, J=5 Hz, 1H, pyr-H); tR=11.58 min (0__60__20); MS (+ve): 406.53.

Example I-41

{3-[4-(6,8-Dimethyl-1-oxo-1,2,3,4-tetrahydro-pyrrolo[1,2-a]pyrazin-7-yl)-pyrimidin-2-ylamino]-phenoxy}-acetic acid $^1$H NMR DMSO: 2.41 (s, 3H, CH3), 2.42 (s, 31 CH3), 3.90 (t, J=9 Hz, 2H, CH2), 4.32 (t, J=9 Hz, 2H, CH2), 4.60 (s, 2H, CH2), 6.45 (d, J=7.5 Hz, 1H, phe-H), 6.81 (d, J=5 Hz, 1H, pyr-H), 7.15 (dd, J=8 Hz, 1H, phe-H), 7.42 (d, J=7.5 Hz, 1H, phe-H), 7.48 (s, 1H, phe-H), 8.39 (d, J=5 Hz, 1H, pyr-H), 9.38 (bs, 1H, NH); tR=11.16 min (0__60__20).

Example I-42

N-{3-[4-(6,8-Dimethyl-1-oxo-1,2,3,4-tetrahydro-pyrrolo[1,2-a]pyrazin-7-yl)-pyrimidin-2-ylamino]-phenyl}-methanesulfonamide $^1$H NMR CD3OD: 2.53 (s, 3H, CH3), 2.53 (s, 3H, CH3), 2.97 (s, 3H, CH3), 4.19 (t, J=9.5 Hz, 2H, CH2), 5.03 (t, J=9.5 Hz, 2H, CH2), 6.87-6.89 (m, 2H, phe-H and pyr-H), 7.26 (t, J=8 Hz, 1H, phe-H), 7.42 (d, J=8 Hz, 1H, phe-H), 7.80 (s, 1H, phe-H), 8.46 (d, J=5 Hz, 1H, pyr-H); tR=11.23 min (0__60__20); MS (+ve): 427.52.

Example I-43

4-[4-(6,8-Dimethyl-1-oxo-1,2,3,4-tetrahydropyrrolo[1,2-a]pyrazin-7-yl)-pyrimidin-2-ylamino]-2-methoxy-N-methyl-benzenesulfonamide $^1$H NMR CD3OD: 2.45 (s, 3H, CH3), 2.47 (s, 3H, CH3), 2.48 (s, 3H, CH3), 3.91 (s, 3H, CH3), 4.15 (t, J=9.5 Hz, 2H, CH2), 5.00 (t, J=9.5 Hz, 2H, CH2), 6.85 (d, J=5 Hz, 1H, pyr-H), 7.42 (d, J=8.5 Hz, 1H, phe-H), 7.63 (d, J=8.5 Hz, 1H, phe-H), 7.67 (s, 1H, phe-H), 8.43 (d, J=5 Hz, 1H, pyr-H); MS (+ve): 457.46.

Example I-44

6,8-Dimethyl-7-{2-[4-(2-oxo-oxazolidin-3-yl)-phenylamino]-pyrimidin-4-yl}-3,4-dihydro-2H-pyrrolo[1,2-a]pyrazin-1-one $^1$H NMR (CDCl$_3$): 2.18 (s, 3H, CH3), 2.43 (s, 3H, CH3), 4.10 (4H, m, pyrrolopyrazinone CH2 and oxazolidine, CH2), 4.46 (4H, m, pyrrolopyrazinone CH2 and oxazolidine, CH2), 6.78 (1H, d, J=5.40 Hz, pyrimidine H), 7.22 (1H, s, NH), 7.45 (2H, d, J=7.80 Hz, aryl-H), 7.63 (2H, d, J=8.70 Hz, aryl-H), 8.41 (1H, d, J=5.40 Hz, pyrimidine H). C22H24N6O3 expected 418.45; found [M+1]+419.58. HPLC: R.T 9.575 mins (10__70__20)

Example I-45

7-[2-(4H-Benzo[1,3]dioxin-6-ylamino)-pyrimidin-4-yl]-6,8-dimethyl-3,4-dihydro-2H-pyrrolo[1,2-a]pyrazin-1-one $^1$H NMR (DMSO): 2.38 (s, 3H), 2.42 (s, 3H), 3.89 (t, 2H, J=9.3 Hz), 4.31 (t, 2H, J=9.3 Hz), 4.84 (s, 2H), 5.21 (s, 2H), 6.75 (d, 1H, J=5.4 Hz), 6.77 (d, 1H, J=8.8 Hz), 7.45 (dd, 1H, J=8.8, 2.4 Hz), 7.51 (d, 1H, 2.4 Hz), 8.33 (d, 1H, 5.4 Hz), 9.21 (bs, 1H), 11.47 (bs, 1H).

Example I-46

6,8-Dimethyl-7-{2-[3-(2-methyl-pyrimidin-4-yl)-phenylamino]-pyrimidin-4-yl}-3,4-dihydro-2H-pyrrolo[1,2-a]pyrazin-1-one $^1$H NMR (DMSO): 2.41 (s, 3H), 2.45 (s, 3H), 2.65 (s, 3H), 3.90 (t, 2H, J=9.3 Hz), 4.32 (t, 2H, J=9.3 Hz), 6.85 (d, 1H, J=4.9 Hz), 7.43 (t, 1H, J=7.8 Hz), 7.69 (d, 1H, J=7.8 Hz), 7.76 (d, 1H, J=5.4 Hz), 7.93 (dd, 1H, J=7.3, 1.0 Hz), 8.42 (d, 1H, J=5.4 Hz), 8.71 (s, 1H), 8.72 (d, 1H, 5.4 Hz), 9.59 (bs, 1H), 11.49 (bs, 1H).

Example I-47

N-{2-Chloro-4-[4-(6,8-dimethyl-1-oxo-1,2,3,4-tetrahydro-pyrrolo[1,2-a]pyrazin-7-yl)-pyrimidin-2-ylamino]-phenyl}-acetamide $^1$H NMR (DMSO): 2.04 (s, 3H), 2.41 (s, 3H), 2.45 (s, 3H), 3.90 (t, 2H, J=9.3 Hz), 4.32 (t, 2H, J=9.3 Hz), 6.85 (d, 1H, J=5.4 Hz), 7.45 (d, 1H, J=8.8 Hz), 7.55 (dd, 1H, J=8.8, 2.4 Hz), 8.17 (d, 1H, J=2.4 Hz), 8.41 (d, 1H, J=5.3 Hz), 9.39 (bs, 1H), 9.59 (bs, 1H), 11.52 (bs, 1H).

Example I-48

6,8-Dimethyl-7-[2-(2-methyl-1H-indol-5-ylamino)-pyrimidin-4-yl]-3,4-dihydro-2H-pyrrolo[1,2-a]pyrazin-1-one $^1$H NMR (DMSO): 2.35 (s, 3H), 2.37 (s, 3H), 2.42 (s, 3H), 3.89 (t, 2H, J=9.3 Hz), 4.31 (t, 2H, J=9.3 Hz), 6.00 (bs, 1H), 6.68 (d, H, J=5.4 Hz), 7.13 (d, 1H, 8.3 Hz), 7.21 (dd, 1H, J=8.3, 1.9 Hz), 7.81 (d, H, J=1.5 Hz), 8.30 (d, 1H, J=5.4 Hz), 8.98 (bs, 1H), 10.69 (bs, 1H), 11.42 (bs, 1H).

Example I-49

6,8-Dimethyl-7-[2-(3-oxazol-5-yl-phenylamino)-pyrimidin-4-yl]-3,4-dihydro-2H-pyrrolo[1,2-a]pyrazin-1-one $^1$H NMR (DMSO): 2.40 (s, 3H), 2.49 (s, 3H), 3.90 (t, 2H, J=9.8 Hz), 4.32 (t 2H, J=9.3 Hz), 6.85 (d, 1H, J=5.9 Hz), 7.30 (d, 1H, J=7.3 Hz), 7.37 (t, 1H, J=7.8 Hz), 7.56 (s, 1H), 7.79 (m, 1H), 8.19 (t, 1H, J=1.9 Hz), 8.41-8.42 (m, 2H), 9.54 (bs, 1H), 11.49 (bs, 1H).

Example I-50

6,8-Dimethyl-7-{2-[4-(morpholine-4-sulfonyl)-phenylamino]-pyrimidin-4-yl}-3,4-dihydro-2H-pyrrolo[1,2-a]pyrazin-1-one $^1$H NMR (DMSO): 2.41 (s, 3H), 2.43 (s, 3H), 2.86 (t, 4H, J=4.9 Hz), 3.59 (t, 4H, J=4.9 Hz), 3.90 (t, 2H, =9.3 Hz), 4.32 (t, 3H, J=9.3 Hz), 6.89 (d, 1H, J=4.9 Hz), 7.25 (dd, 1H, J=7.8, 1.0 Hz), 7.55 (t, 1H, J=7.8 Hz), 8.10 (dd, 1H, J=8.3, 2.0 Hz), 8.27 (d, 1H, J=1.9 Hz), 8.44 (d, 1H, J=5.4 Hz), 9.8 (bs, 1H), 11.51 (s, 1H). MS (ES): m/z 483.29 (MH+) C23H26N6O4S=482.57

Example I-51

6,8-Dimethyl-7-{2-[4-(2-morpholin-4-yl-ethoxy)-phenylamino]-pyrimidin-4-yl}-3,4-dihydro-2H-pyrrolo[1,2-a]pyrazin-1-one $^1$H NMR (DMSO): 2.37 (s, 3H), 2.41 (s, 3H), 2.66 (t, 2H, J=5.9 Hz), 3.31 (m, 4H), 3.57 (t, 4H, J=5.4 Hz), 3.89 (t, 2H, J-9.3 Hz), 4.03 (t, 2H, J=5.9 Hz), 4.31 (t, 2H, J=5.9 Hz), 4.31 (t, 2H, J=9.3 Hz), 6.73 (d, 1H, J=4.9 Hz), 6.86 (d, 2H, J=9.3 Hz), 8.32 (d, 1H, J=4.9 Hz), 9.16, (1 s, 1H), 11.45 (bs, 1H). MS ES): m/z 463.54 (MH+) C25H30N6O3=462.56

Example I-52

6,8-Dimethyl-7-[2-(4-oxazol-5-yl-phenylamino)-pyrimidin-4-yl]-3,4-dihydro-2H-pyrrolo[1,2-a]pyrazin-1-one $^1$H NMR DMSO): 2.41 (s, 3H), 2.45 (s, 3H), 3.90 (t, 2H, J=9.3 Hz), 4.32 (t, 2H, J=8.8 Hz), 6.85 (d, 1H, J=5.4 Hz), 7.53 (s, 1H, 7.63 (d, 2H, J=8.8 Hz), 7.92 (d, 2H, J=8.8 Hz), 8.36 (s, 1H), 8.42 (d, 1H, J=4.9 Hz), 9.63 (bs, 1H), 11.52 (bs, 1H). MS (ES): m/z 401.61 (MH+) C22H20N6O2=400.44.

Example I-53

6,8-Dimethyl-7-[2-(3-pyrimidin-5-yl-phenylamino)-pyrimidin-4-yl]-3,4-dihydro-2H-pyrrolo[1,2-a]pyrazin-1-one $^1$H NMR (DMSO) 2.38 (s, 3H), 2.42 (s, 3H), 3.89 (t, 2H, J=9.3 Hz), 4.31 (t, 2H, J=9.3 Hz), 6.85 (d, 1H, J=5.4 Hz), 7.34 (m, 1H), 7.45 (t, 1H, J=7.8 Hz), 7.94 (m, 1H), 8.15 (m, 1H), 8.42 (d, 1H, H=5.4 Hz), 9.07 (s, 2H), 9.20 (s, 1H), 9.54 (bs, 1H), 11.49 (bs, 1H). MS ES): m/z 412.55 (MH+) C23H21N7O=411.47.

Example I-54

6,8-Dimethyl-7-[2-(4-pyridin-4-ylmethyl-phenylamino)-pyrimidin-4-yl]-3,4-dihydro-2H-pyrrolo[1,2-a]pyrazin-1-one $^1$H NMR (DMSO): 2.38 (s, 3H), 2.42 (s, 3H), 3.89 (t, 2H, J=9.3 Hz), 4.31 (t, 2H, J=9.3 Hz), 6.78 (d, 1H, J=4.9 Hz), 7.14 (d, 2H, 8.5 Hz), 7.23 (d, 2H, J=5.9 Hz), 7.70 (d, 2H, J=8.8 Hz), 8.35 (d, 1H, J=5.9 Hz), 8.44 (d, 2H, J=5.9 Hz), 9.32 (bs), 11.47 (bs, 1H). MS ES): m/z 425.54 (MH+) C25H24N6O=424.51

Example I-55

6,8-Dimethyl-7-{2-[4-(pyrrolidine-1-sulfonyl)-phenylamino]-pyrimidin-4-yl}-3,4-dihydro-2H-pyrrolo[1,2-a]pyrazin-1-one $^1$H NMR (DMSO): 1.62-1.65 (m, 4H), 2.41 (s, 3H), 2.44 (s, 3H), 3.14 (t, 4H, J=6.8 Hz), 3.9 (t, 2H, J=9.3 Hz), 4.32 (t, 2H, J=9.3 Hz), 6.88 (d, 1H, J=5.4 Hz), 7.31 (d, 1H, J=7.8 Hz), 7.51 (t, 1H, J=7.8 Hz), 8.09 (dd, 1H, J=7.8, 1.5 Hz), 8.30 (t, 1H, J=1.9 Hz), 8.43 (d, 1H, J=5.4 Hz), 9.75 (bs, 1H), 11.51 (bs, 1H). MS ES): m/z 467.25 (MH+) C23H26N6O3S=466.57.

Example I-56

6,8-Dimethyl-7-{2-[4-(piperidine-1-sulfonyl)-phenylamino]-pyrimidin-4-yl}-dihydro-2H-pyrrolo[1,2-a]pyrazin-1-one $^1$H NMR (DMSO): 1.34-1.35 (m, 2H), 1.52-1.54 (m, 4H), 2.42 (s, 3H), 2.45 (s, 3H), 2.85 (t, 4H, J=5.4 Hz), 3.90 (t, 2H, J=9.3 Hz), 4.32 (t, 2H, J=9.3 Hz), 6.93 (d, 1H, J=5.4 Hz), 7.62 (d, 2H, J=8.8 Hz), 8.03 (d, 2H, J=8.8 Hz), 8.46 (d, 1H, J=5.4 Hz), 9.94 (bs, 1H), 11.55 (is, 1H). MS ES): m/z 481.45 (MH+) C24H28N6O3S=480.59.

Example I-57

7-[2-(4-Benzyloxy-phenylamino)-pyrimidin-4-yl]-6,8-dimethyl-3,4-dihydro-2H-pyrrolo[1,2-a]pyrazin-1-one $^1$H NMR (DMSO): 2.37 (s, 3H), 2.41 (s, 3H, 3.89 (t, 2H, J=9.3 Hz), 4.31 (t, 2H, J=9.3 Hz), 5.05 (s, 2H), 6.74 (d, 1H, J=5.4 Hz), 6.94 (d, 2H, J=8.8 Hz), 7.32 (t, 1H, J=7.3 Hz), 7.38 (t, 2H, J=7.3 Hz), 7.44 (d, 2H, J=7.3 Hz), 7.64 (d, 2H, J=8.8 Hz), 8.32 (d, 1H, J=4.9 Hz), 9.17 (bs, 1H), 11.46 (bs, 1H). MS(ES): m/z 440.57 (MH+) C26H25N5O2=438.51.

Example I-58

7-[2-(3-Benzoyl-phenylamino)-pyrimidin-4-yl]-6,8-dimethyl-3,4-dihydro-2H-pyrrolo[1,2-a]pyrazin-1-one $^1$H NMR (DMSO): 2.36 (s, 3H), 2.40 (s, 3H), 3.90 (t, 2H, J=9.3 Hz), 4.31 (2H, J=9.3 Hz), 6.84 (d, 1H J 4.9 Hz), 7.25 (d, 1H, J=7.8 Hz), 7.45 (t, 1H, J=8.3 Hz), 7.53 (t, 2H, J=7.8 Hz), 7.65 (t, 1H, J=7.8 Hz), 7.75 (d, 2H, J=7.3 Hz), 8.07 (dd, 1H, J=8.3, 2.0 Hz), 8.27 (t, 1H, J 2.0 Hz), 8.40 (d, H, J=4.9 Hz), 9.65 (bs, 1H), 11.47 (bs, 1H). MS (ES): m/z 438.53 (MH+) C26H23N5O2=437.49

Example I-59

N-{3-[4-(6,8-Dimethyl-1-oxo-1,2,3,4-tetrahydro-pyrrolo[1,2-a]pyrazin-7-yl)-pyrimidin-2-ylamino]-phenyl}-acetamide $^1$H NMR (DMSO): 2.02 (s, 3H), 2.39 (s, 3H), 2.43 (s, 3H), 3.90 (t, 2H, J=9.3 Hz), 4.31 (t, 2H, J=9.3 Hz), 6.81 (d, 1H, J=5.4 Hz), 7.15 (t, 2H, J=7.8 Hz), 7.20 (d, 1H, J=7.8 Hz), 7.49 (d, 1H, J=8.3 Hz), 7.85 (bs, H1), 8.36 (d, 1H, J=5.4 Hz), 9.34 (bs, 1H), 11.43 (bs, 1H). MS (ES): m/z 391.55 (MH+) C21H22N6O2=390.45.

Example I-60

6,8-Dimethyl-7-[2-(4-[1,2,3]thiadiazol-4-yl-phenylamino)-pyrimidin-4-yl]-3,4-dihydro-2H-pyrrolo[1,2-a]pyrazin-1-one $^1$H NMR (DMSO): 2.43 (s, 31), 2.47 (s, 3H), 3.91 (t, 2H, J=9.8 Hz), 4.32 (t, 2H, J=9.3 Hz), 6.87 (d, 1H, J=5.4 Hz), 7.98 (d, 2H, J=8.8 Hz), 8.05 (d, 2H. J 8.8 Hz), 8.44 (d, 1H, J=5.4

Hz), 9.46 (s, 1H), 9.67 (bs, 1H), 11.53 (bs, 1H). MS (ES): M/z 418.50 (MH+) C21H19N7OS=417.50.

Example I-61

6,8-Dimethyl-7-[2-(4-trifluoromethoxy-phenylamino)-pyrimidin-4-yl]-3,4-dihydro-2H, pyrrolo[1,2-a]pyrazin-1-one ¹H NMR (DMSO): 2.40 (s, 3), 2.43 (s, 3H), 3.90 (t, 2H, J=9.3 Hz), 4.32 (t 2H, J=9.8 Hz), 6.85 (d, 1H, J=5.4 Hz), 7.27 (d, 2H, J=7.8 Hz), 7.88 (d, 2H, J=8.8 Hz), 8.40 ((d, 1H, J=5.4 Hz), 9.60 (bs, 1H-, 11.51 (bs, 1H). MS ES): m/z 418.50 (MH+) C20H18F3N5O2.

Example I-62

7-[2-(3,4-Dihydro-2H-benzo[b][1,4]dioxepin-7-ylamino)-pyrimidin-4-yl]-6,8-dimethyl-3,4-dihydro-2H-pyrrolo[1,2-a]pyrazin-1-one ¹H NMR (DMSO): 2.04-2.08 (m, 2H), 2.39 (s, 3H), 2.42 (s, 3H), 3.90 (t, 2H, J=9.3 Hz), 4.03 (t, 2H, J=5.4 Hz), 4.08 (t, 2H, J=5.4 Hz), 4.31 (t 2H, J=9.3 Hz), 6.77 (d, 1H, J=5.4 Hz), 6.86 (d, 1H, J=8.8 Hz), 7.25 (dd, 1H, J=8.8, 2.9 Hz), 7.58 (d, 1H, J=2.9 Hz), 8.35 (d, 1H, J=5.4 Hz), 9.28 (bs, 1H), 11.47 (bs, 1H).

Example I-63

7-[2-(2,2-Dioxo-2,3-dihydro-1H-2-benzo[c]thiophen-5-ylamino)-pyrimidin-4-yl]-6,8-dimethyl-3,4-dihydro-2H-pyrrolo[1,2-a]pyrazin-1-one ¹H NMR DMSO): 2.40 (s, 3H), 2.44 (s, 3), 3.90 (t, 2H, J=9.3 Hz), 4.32 (t, 2H, J=9.3 Hz), 4.39 (s, 2H), 4.45 (s, 21, 6.84 (d, 1H, 5.5 Hz), 7.26 (d, 1H, J=8.3 Hz), 7.73 (dd, 1H, J=7.8, 1.5 Hz), 7.87 (s, 1H), 8.40 (d, 1H, J=5.4 Hz), 9.56 (bs, 1H), 11.51 (bs, 1H).

Example I-64

7-[2-(3-Chloro-4-fluoro-phenylamino)-pyrimidin-4-yl]-6,8-dimethyl-3,4-dihydro-2H-pyrrolo[1,2-a]pyrazin-1-one ¹H NMR D6 dmso 2.39 (3H, s, CH3); 2.43 (3H, s, CH3); 3.89 (2H, t J=9.45 Hz, —CH2N—); 4.31 (2H, t J=9.45 Hz, —CH2N—); 6.85 (1H, d, J=5.4 Hz, pyrimidine H); 7.32 (1H, t J=9 Hz, aryl-H); 7.61 (1H, m, aryl-H); 8.21 (1H, dd J=9 Hz and 2.7 Hz, aryl H); 8.41 (1H, d, J=5.4 Hz, pyrimidine H); 9.63 (1H, s, NH); 11.53 (1H, s, CONH C19H17ClFN5O MWt=385.83. (M+1)+ found 386 (388).

Example I-65

7-[2-(2-Fluoro-phenylamino)-pyrimidin-4-yl]-6,8-dimethyl-3,4-dihydro-2H-pyrrolo[1,2-a]pyrazin-1-one ¹H NMR D6 dmso 2.30 (3H, s, CH3); 2.36 (3H, s, CH3); 3.87 (2H, t J=9.45 Hz, —CH2N—); 4.29 (2H, t J 9.45 Hz, —CH2N—); 6.79 (1H, d, J=5.4 Hz, pyrimidine H); 7.15 (1H, m, aryl-H); 7.73 (1H, m, aryl-H); 8.31 (1H, d J=5.4 Hz, pyrimidine H); 8.78 (1H, s, NH); 11.44 (1H, s, CONH) C19H18FN5O MWt=351.39. (M+1)+ found 352.

Example I-66

7-[2-(2,4-Difluoro-phenylamino)-pyrimidin-4-yl]-6,8-dimethyl-3,4-dihydro-2H-pyrrolo[1,2-a]pyrazin-1-one ¹H NMR D6 dmso 2.28 (3H, s, CH3); 2.32 (3H, s, CH3); 3.89 (2H, t J=9.45 Hz, —CH2N—); 4.29 (2H, t J=9.45 Hz, —CH2N—); 6.77 (1H, d, J=5.4 Hz, pyrimidine H); 7.05 (1H, m, aryl-H); 7.26 (1H, m, aryl-H); 7.63 (1H, m, aryl-H); 8.29 (1H, d J=5.4 Hz, pyrimidine H); 8.81 (1H, s, NH); 11.44 (1H, s, CONH) C19H17F2N5O MWt=369.38. (M+1)+ found 370.

Example I-67

7-[2-(3-Chloro-4-methoxy-phenylamino)-pyrimidin-4-yl]-6,8-dimethyl-3,4-dihydro-2H-pyrrolo[1,2-a]pyrazin-1-one ¹H NMR D6 dmso 2.40 (3H, s, CH3); 2.44 (3H, s, CH3); 3.90 (2H, t J=9.30 Hz, —CH2N—); 4.32 (2H, t J=9.30 Hz, —CH2N—); 6.79 (1H, d, J=5.3 Hz, pyrimidine H); 7.93 (1H, d J=4.65 Hz, aryl-H); 7.57 (1H, dd J=2.70 and 9.0 Hz, aryl-H); 8.40 (1H, d J=2.7 Hz, aryl-H); 8.37 (1H, d J=5.34 Hz, pyrimidine H); 9.38 (1H, s, NM; 11.50 (1H, s, CONH) C20H20ClN5O2 MWt=397.87. (M+1)+ found 398 and 400.

Example I-68

6,8-Dimethyl-7-[2-(4-trifluoromethyl-phenylamino)-pyrimidin-4-yl]-3,4-dihydro-2H-pyrrolo[1,2-a]pyrazin-1-one C20H18F3N5O MWt=401.39. (M+1)+ found 402.

Example I-69

7-[2-(3-Chloro-phenylamino)-pyrimidin-4-yl]-6,8-dimethyl-3,4-dihydro-2H-pyrrolo[1,2-a]pyrazin-1-one ¹H NMR D6 dmso 2.42 (3H, s, CH3); 2.46 (3H, s, CH3); 3.91 (2H, t J=9.23 Hz, —CH2N—); 4.33 (2H, t J=9.23 Hz, —CH2N—); 6.87 (1H, d, J=5.4 Hz, pyrimidine H); 6.95 (1H, m, aryl-H) 7.28 (1H, t J=8.1 Hz, aryl-H); 7.62 (1H, d J=8.4, aryl-H); 8.15 (1H, s, aryl-H); 8.43 (1H, d J=5.4 Hz, pyrimidine H); 9.65 (1H, s, NH); 11.54 (1H, s, CONH) C19H18ClN5O MWt=367.84. (M+1)+ found 360 and 370.

Example I-70

{4-[4-(6,8-Dimethyl-1-oxo-1,2,3,4-tetrahydro-pyrrolo[1,2-a]pyrazin-7-yl)-pyrimidin-2-ylamino]-phenyl}-acetic acid ¹H NMR D6 dmso 2.39 (3H, s, —CH3), 2.43 (3H, s, —CH3); 2.55 (2H, t J=7.7 Hz, —CH2); 2.74 (2H, t J=7.7 Hz; —CH2); 2.80 (3H, s, NMe); 2.91 (3H, s, NMe); 3.89 (2H, t J=9.3 Hz, —CH2-); 4.31 (2H, t J=9.3 Hz, —CH2-); 6.78 (2H, m aryl CH and pyrimidine CH); 7.15 (1H, t J=7.95, aryl CH); 7.61 (2H, m, aryl CH); 8.36 (1H, d J=5.4 Hz, pyrimidine CH);

9.29 (1H, s, —NH); 11.47 (1H, s, —NH) C24H28N6O2 MWt 432.53 (M+1)+ found 433

Example I-71

6,8-Dimethyl-7-{2-[4-(2-methyl-thiazol-4-yl)-phenylamino]-pyrimidin-4-yl}-3,4-dihydro-2H-pyrrolo[1,2-a]pyrazin-1-one C23H22N6OS MWt 430.54 found (M+1)+ 431

Example I-72

6,8-Dimethyl-7-[2-(4-pyrazol-1-yl-phenylamino)-pyrimidin-4-yl]-3,4-dihydro-2H-pyrrolo[1,2-a]pyrazin-1-one $^1$H NMR D6 dmso 2.45 (3H, s, —CH3), 2.49 (3H, s, —CH3); 3.94 (2H, t J=9.2 Hz, —CH2-); 4.36 (2H, t J=9.2 Hz, —CH2-); 6.34 (1H, t J=2.25 Hz, pyrazole-H); 6.87 (1H, d J=5.1 Hz, pyrimidine CH); 7.72 (1H, t J=1.8 Hz, pyrazole CH); 7.76 (2H, d J=9.0 Hz, aryl CH); 7.95 (2H, d J=9.0 Hz, aryl CH); 8.42 (1H, d J=2.4 Hz, pyrazole-H); 9.59 (1H, s, —NH); 11.66 (1H, s, —NH) C22H21N7O MWt 399.46 found (M+1)+ 400

Example I-73

6,8-Dimethyl-7-[2-(4-[1,2,4]triazol-1-yl-phenylamino)-pyrimidin-4-yl]-3,4-dihydro-2H-pyrrolo[1,2-a]pyrazin-1-one C21H20N8O MWt400.45 found (M+1)+ 401

Example I-74

6,8-Dimethyl-7-[2-(4-pyrrol-1-yl-phenylamino)-pyrimidin-4-yl]-3,4-dihydro-2H-pyrrolo[1,2-a]pyrazin-1-one C23H22N6O MWt 398.47 found (M+1)+ 399

Example I-75

7-{2-[4-(2,3-Dihydro-imidazo[2,1-b]thiazol-6-yl)-phenylamino]-pyrimidin-4-yl}-6,8-dimethyl-3,4-dihydro-2H-pyrrolo[1,2-a]pyrazin-1-one C24H23N7OS MWt 457.56 found (M+1)+ 458

Example I-76

7-[2-(3-Methoxy-4-methylamino-phenylamino)-pyrimidin-4-yl]-6,8-dimethyl-3,4-dihydro-2H-pyrrolo[1,2-a]pyrazin-1-one $^1$H (DMSO): 2.37 (3H, s, CH3), 2.41 (3H, s, CH3), 2.69 (3H, s, CH3), 3.73 (3H, s, OCH3), 3.89 (2H, t, J 9.5 Hz, CH2), 4.30 (2H, t, J 9.5 Hz, CH2), 4.65 (1H, br s, NH), 6.40 (1H, d, J 8.5 Hz, Ar—H), 6.67 (1H, d, J 5.0 Hz, pyr-H), 7.17 (1H, d, J 2.0 Hz, Ar—H), 7.21 (1H, dd, J 8.5, 2.0 Hz, Ar—H), 8.28 (1H, d, J 5.0 Hz, pyr-H), 8.87 (1H, s, NM, 11.42 (1H, s, NH); MS (+ve): 393.00; tR=10.2 min (10-70-20)

Example I-77

4-[4-(6,8-Dimethyl-1-oxo-1,2,3,4-tetrahydro-pyrrolo[1,2-a]pyrazin-7-yl)-pyrimidin-2-ylamino]-benzonitrile $^1$H (DMSO): 2.47 (3H, s, CH3), 2.50 (3H, s, CH3), 4.06 (2H, t, J 9.0 Hz, CH2), 4.80 (2H, t, J 9.0 Hz, CH2), 7.02 (1H, d, J 5.5 Hz, pyr-H), 7.74 (2H, d, J 8.5 Hz, 2×Ar—H), 8.00 (2H, d, J 8.5 Hz, 2×Ar—H), 8.56 (1H, d, J 5.5 Hz, pyr-H), 10.11 (1H, s, NH), 12.39 (1H, s, NH); MS (+ve): 359.20; tR=15.15 min (10_70_20)

Example I-78

6,8-Dimethyl-7-[2-(4-pyridin-3-yl-phenylamino)-pyrimidin-4-yl]-3,4-dihydro-2H-pyrrolo[1,2-a]pyrazin-1-one C24H22N6O MWt=410.48. (M+1)+ found 411

Example I-79

6,8-Dimethyl-7-{2-[4-(4-methyl-4H-[1, 2, 4]triazol-3-yl)-phenylamino]-pyrimidin-4-yl}-3,4-dihydro-2H-pyrrolo[1,2-]pyrazin-1-one C22H22N8O MWt=414.47. (M+1)+ found 415

Example I-80

7-{2-[4-(3,5-Dimethyl-pyrazol-1-yl)-phenylamino]-pyrimidin-4-yl}-6,8-dimethyl-3,4-dihydro-2H-pyrrolo[1,2-a]pyrazin-1-one C24H25N7O MWt=427.51. (M+1)+ found 428

Example I-81

1-{4-[4-(6,8-Dimethyl-1-oxo-1,2,3,4-tetrahydro-pyrrolo[1,2-a]pyrazin-7-yl)-pyrimidin-2-ylamino]-phenyl}-5-methyl-1H-pyrazole-4-carboxylic acid ethyl ester C26H27N7O3 MWt=485.55. (M+1)+ found 486

Example I-82

7-[2-(4-Isoxazol-5-yl-phenylamino)-pyrimidin-4-yl]-6,8-dimethyl-3,4-dihydro-2H-pyrrolo[1,2-]pyrazin-1-one $^1$H NMR D6 dmso 2.42 (3H, s, —CH3), 2.45 (3H, s, —CH3); 3.89 (2H, t J=9.2 Hz, —CH2-); 4.32 (2H, t J=9.2 Hz, —CH2-); 6.85 (1H, d J=1.95 Hz, oxazole-H); 6.89 (1H, d J=5.7 Hz, pyrimidine CH); 7.78 (2H, d J=8.8 Hz, aryl CH); 7.98 (2H, d J=8.8 Hz, aryl CH); 8.42 (1H, d J=5.4 Hz, pyrimidine-H); 8.56 (1H, d J=1.95 Hz, oxazole-CH); 9.75 (1H, s, —NH); 11.53 (1H, s, —NH) C22H20N6O2 MWt=400.44. (M+1)+ found 401

Example I-83

2-(4-{4-[4-(6,8-Dimethyl-1-oxo-1,2,3,4-tetrahydro-pyrrolo[1,2-a]pyrazin-7-yl)-pyrimidin-2-ylamino]-phenyl}-thiazol-2-yl)-acetamide C24H23N7O2S MWt=473.56. (M+1)+ found 474

Example I-84

4-{4-[4-(6,8-Dimethyl-1-oxo-1,2,3,4-tetrahydro-pyrrolo[1,2-a]pyrazin-7-yl)-pyrimidin-2-ylamino]-phenyl}-thiazol-2-yl)-acetonitrile $^1$H NMR D6 dmso 2.41 (3H, s, —CH3), 2.45 (3H, s, —CH3); 3.89 (2H, t J=9.2 Hz, —CH2-); 4.31 (2H, t J=9.2 Hz, —CH2-); 4.60 (2H, s, —CH2CN); 6.83 (1H, d J=5.1 Hz, pyrimidine CH); 7.66 (4H, ABq, aryl CH); 7.94 (1H, s, thiazole CH); 8.40 (1H, d J=5.1 Hz, pyrimidine-H); 9.56 (1H, s, —NH); 11.53 (1H, s, —NH) C24H21N7OS MWt=455.55. (M+1)+ found 456

Example I-85

7-[2-(2,4-Dimethoxy-phenylamino)-pyrimidin-4-yl]-6,8-dimethyl-3,4-dihydro-2H-pyrrolo[1,2-a]pyrazin-1-one $^1$H NMR (DMSO): 2.32 (s, 3H), 2.71 (s, 3H), 3.75 (s, 3H), 3.79 (s, 3H), 3.88 (t, 2H, J=9.3 Hz), 4.30 (t, 2H, J=9.3 Hz), 6.50 (dd, 1H, J=8.8, 2.9 Hz), 6.61 (d, 1H, J=2.4 Hz), 6.72 (d, 1H, J=4.9 Hz), 7.78-7.79 (m, 2H), 8.28 (d, 1H, J=5.4 Hz), 11.43 (bs, 1H). MS (ES): m/z 394.56 (MH+) C21H23N5O3=393.45.

Example I-86

7-[2-(2-Chloro-4-fluoro-phenylamino)-pyrimidin-4-yl]-6,8-dimethyl-3,4-dihydro-2H-pyrrolo[1,2-a]pyrazin-1-one C19H17ClFN5O MWt=385.83. (M+1)+ found 385+387

Example I-87

7-[2-(5-Chloro-2-methoxy-phenylamino)-pyrimidin-4-yl]-6,8-dimethyl-3,4-dihydro-2H-pyrrolo[1,2-a]pyrazin-1-one C20H20ClN5O2 MWt=397.87. (M+1)+ found 398+400

Example I-88

7-[2-(5-Fluoro-2-methyl-phenylamino)-pyrimidin-4-yl]-6,8-dimethyl-3,4-dihydro-2H-pyrrolo[1,2-a]pyrazin-1-one 1H (DMSO): 2.22 (3H, s, CH3), 2.33 (3H, s, CH3), 2.38 (3H, s, CH3), 3.89 (2H, t, J 9.5 Hz, CH2), 4.30 (2H, t, J 9.5 Hz, CH2), 6.80 (2H, m, pyr-H) and Aryl-H, 7.19 (1H, t, J 7.5 Hz, Ar—H), 7.63 (1H, dd, J 11.4, 2.07 Hz, Ar—H), 8.34 (1H, d, J 5.0 Hz, pyr-H), 8.51 (1H, s, NH), 11.46 (1H, s, NH); MS (+ve): 366

Example I-89

6,8-Dimethyl-7-[2-(4-p-tolyloxy-phenylamino)-pyrimidin-4-yl]-3,4-dihydro-2H-pyrrolo[1,2-a]pyrazin-1-one 1H NMR (DMSO): 2.276 (s, 3H CH3), 2.45 (s, 6H, 2×CH3), 4.05 (t, 2H, J=9.5 Hz, CH2), 4.81 (t, 2H, J=9.5 Hz, CH2), 6.85-6.89 (m, 3H, 2×PheH, 1PyrH), 6.97 (d, 2H, J=9.0 Hz, 2×PheH), 7.17 (d, 2H, 1=9.0 Hz, 2×PheH), 7.74 (d, 2H, J=9.5 Hz, 2×PheE), 8.45 (d, 1H, J=5.0 Hz, PyrH), 9.52 (bs, 1H, NH), 12.21 (bs, 1H, NM mass+ve 440.64 HPLC rt—16.93 0__20-60

Example I-90

N-(2-Diethylamino-ethyl)-4-[4-(6,8-dimethyl-1-oxo-1,2,3,4-tetrahydro-pyrrolo[1,2-a]pyrazin-7-yl)-pyrimidin-2-ylamino]-2-methyl-benzenesulfonamide $^1$H NMR (CD3OD): δ 1.31 (t, J=7.5 Hz, 6H, 2×CH$_3$), 2.55 (s, 6H, 2×CH$_3$), 2.62 (s, 3H, CH$_3$), 3.23-3.29 (m, 8H, 4×CH$_2$), 4.21 (dd, J=9.5 Hz, 2H, CH$_2$), 5.07 (dd, J=9.5 Hz, 2H, CH$_2$), 6.98 (d, J=5.5 Hz, 1H, pyr-H), 7.38 (d, J=8.5 Hz, 1H, phe-B), 7.83 (dd, J=2.5 and 8.5 Hz, 1H, phe-B), 8.42 (d, J=2.5 Hz, 1H, phe-B), 8.48 (d, J=5.5 Hz, 1H, pyr-H); $t_R$=11.48 min (0__60__20); MS (+ve): 526.47.

Example I-91

N-(3-Dimethylamino-propyl)-4-[4-(6,8-dimethyl-1-oxo-1,2,3,4-tetrahydro-pyrrolo[1,2-a]pyrazin-7-yl)-pyrimidin-2-ylamino]-2,N-dimethyl-benzenesulfonamide $^1$H NMR (CD$_3$OD): δ 2.01-2.07 (m, 2H, CH$_2$), 2.54 (s, 6H, 2×CH$_3$), 2.57 (s, 3H, CH$_3$), 2.89 (s, 3H, CH$_3$), 2.92 (s, 6H, 2×CH$_3$), 3.21 (dd, J=6.5 Hz, 2H, CH$_2$), 3.38 (dd, J=6.5 Hz, 2H, CH$_2$), 4.21 (dd, J=9.5 Hz, 2H, CH$_2$), 5.07 (dd, J=9.5 Hz, 2H, CH$_2$), 6.96 (d, J=5.5 Hz, 1H, pyr-H), 7.36 (d, J=8 Hz, 1H, phe-H), 7.81 (dd, J=2.5 and 8.5 Hz, 1H, phe-H), 8.33 (d, J=2 Hz, 1H, phe-f), 8.49 (d, J=5.5 Hz, 1H, pyr-H); $t_R$=11.89 min (0__60__20); MS (+ve): 526.53.

Example I-92

1-{4-[4-(6,8-Dimethyl-1-oxo-1,2,3,4-tetrahydro-pyrrolo[1,2-a]pyrazin-7-yl)-pyrimidin-2-ylamino]-phenyl}-3,5-dimethyl-1H-pyrazole-4-carboxylic acid ethyl ester C27H29N7O3 MWt=499 (M+1)+ found 500

N-Methyl compounds—prepared from 7-(2-Fluoro-pyrimidin-4-yl)-2,6,8-trimethyl-3,4-dihydro-2H-pyrrolo[1,2-a]pyrazin-1-one and the appropriate aniline.

Example I-93

2,6,8-Trimethyl-7-{2-[3-(2-methyl-pyrimidin-4-yl)-phenylamino]-pyrimidin-4-yl}-3,4-dihydro-2H-pyrrolo[1,2-a]pyrazin-1-one $^1$H NMR (DMSO): 2.35 (s, 3H), 2.40 (s, 3H), 2.65 (s, 3H), 3.80 (s, 3H), 3.92 (t, 2H, J=9.3 Hz), 4.29 (t, 2H, J=9.3 Hz), 6.81 (d, 1H, 5.4 Hz), 7.43 (t, 1H, J=7.8 Hz), 7.70 (m, 1H), 7.75

(d, 1 h, J=5.4 Hz), 7.96 (dd, 1H, J=7.8, 1.5 Hz), 8.45 (d, 1H, J=4.9 Hz), 8.70 (d, 1H, J=1.9 Hz), 8.73 (d, 1H, J=5.4 Hz), 9.66 (bs, 1H).

Example I-94

7-[2-(2,2-Dioxo-2,3-dihydro-1H-2-benzo[c]thiophen-5-ylamino)-pyrimidin-4-yl]-2,6,8-trimethyl-3,4-dihydro-2H-pyrrolo[1,2]pyrazin-1-one $^1$H NMR (DMSO): 2.32 (s, 3H), 2.41 (s, 3 h), 3.80 (s, 3H), 3.92 (t, 2H J=9.8 Hz), 4.30 (t, 2 h, J=9.3 Hz), 4.40 (s, 2H), 4.47 (s, 2H), 6.81 (d, 1H, J=4.9 Hz), 7.26 (d, 1H, J=8.3 Hz), 7.71 (dd, 1H, J=8.3, 1.9 Hz), 7.93 (d, 1H J=1.0 Hz), 8.43 (d, 1H J=4.9 Hz), 9.66 (bs, 1H).

N-Ethyl compounds prepared from 2-Ethyl-7-(2-fluoro-pyrimidin-4-yl)-6,8-dimethyl-3,4-dihydro-2H-pyrrolo[1,2-a]pyrazin-1-one and the appropriate aniline.

Example I-95

2-Ethyl-6,8-dimethyl-7-{2-[3-(2-methyl-pyrimidin-4-yl)-phenylamino]-pyrimidin-4-yl}-3,4-dihydro-2H-pyrrolo[1,2-a]pyrazin-1-one $^1$H NMR (DMSO): 1.31 (t, 3H, J=7.3 Hz), 2.44 (s, 3H), 2.46 (s, 3H), 2.81 (s, 3H), 4.07 (t, 2H, J=9.3 Hz), 4.37-4.40 (m, 4H), 6.80 (d, 1H, J=5.4 Hz), 7.48 (t, 1H, J=7.8 Hz), 7.52 (d, 1H, J=5.4 Hz), 7.74 (d, 1H, J=7.3 Hz), 7.87 (d, 1H J=7.8 Hz), 8.38 (d, 1H, J=5.4 Hz), 8.44 (d, 1H, J=1.9 Hz), 8.68 (d, 1H, J=4.9 Hz).

Example I-95a

7-{2-[6-(4-Fluoro-phenoxy)-pyridin-3-ylamino]-pyrimidin-4-yl}-6,8-dimethyl-3,4-dihydro-2H-pyrrolo[1,2-a]pyrazin-1-one

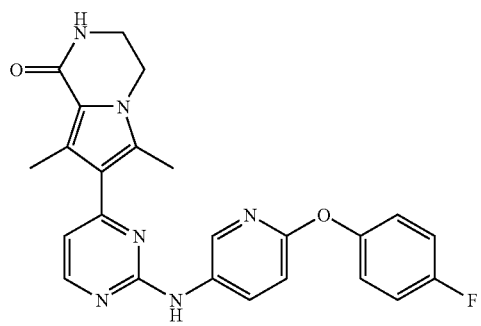 [SMILES: Cc1c(-c2ccnc(Nc3ccc(Oc4ccc(F)cc4)nc3)n2)c(C)n2c1C(=O)NCC2]

MS+ve 445.4

Example I-95b 6,8-Dimethyl-7-{2-[4-(1H-tetrazol-5-yl)-phenylamino]-pyrimidin-4-yl}-3,4-dihydro-2H-pyrrolo[1,2-a]pyrazin-1-one

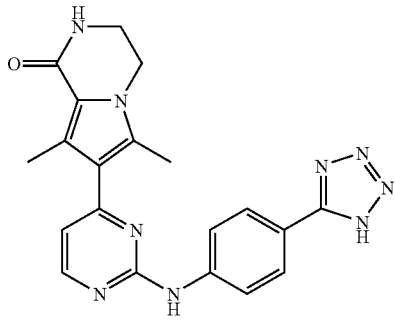 [SMILES: Cc1c(-c2ccnc(Nc3ccc(-c4nnn[nH]4)cc3)n2)c(C)n2c1C(=O)NCC2]

Prepared by reaction of 7-(2-fluoropyrimidin-4-yl)-6,8-dimethyl-3,4-dihydro-2H-pyrrolo[1,2-a]pyrazin-1-one with 4-(1H-tetrazol-5-yl)-phenylamine.

1H (DMSO): δ 2.45 (3H, s, CH3), 2.47 (3H, s, CH3), 4.01 (2H, t, J=9.0, CH2), 4.72 (2H, t, J=9.0, CH2), 6.93 (1H, d, J=5.0, pyrim-H), 7.92 (2H, d, J=9.0, 2×Ar—H), 7.99 (2H, d, J=9.0, 2×Ar—H), 8.50 (1H, d, J=5.0, pyrim-H), 9.90 (1H, s, NH), 12.11 (1H, br s, NH); HPLC: R$_t$=13.22 min (10_70_20).

Example I-95c 6,8-Dimethyl-7-{2-[3-piperidine-1-sutfonyl)-phenylamino]-pyrimidin-4-yl}-3,4-dihydro-2H-pyrrolo[1,2-a]pyrazin-1-one

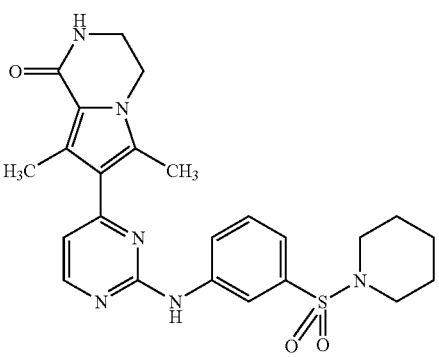 [SMILES: Cc1c(-c2ccnc(Nc3cccc(S(=O)(=O)N4CCCCC4)c3)n2)c(C)n2c1C(=O)NCC2]

Prepared by reaction of 7-(2-fluoropyrimidin-4-yl)-6,8-dimethyl-3,4-dihydro-2H-pyrrolo[1,2-a]pyrazin-1-one with 3-piperidine-1-sulfonyl)-phenylamine $^1$H NMR (CD$_3$OD): δ 1.41-1.45 (m, 2H, piperid-H, 1.57-1.61 (m, 4H, piperid-H), 2.54 (s, 3H, CH$_3$), 2.55 (s, 3H, CH$_3$), 2.97 (t, J=5.5 Hz, 4H, piperid-H), 4.22 (dd, J=9.5 Hz, 2H, CH$_2$), 5.08 (dd, J=9.5 Hz, 2H, CH$_2$), 6.96 (d, J=5 Hz, 1H, pyr-H), 7.38 (d, J=8 Hz, 1H, pheH), 7.52 (dd, J=8 Hz, 1H, phe-H), 7.82 (d, J=8 Hz, 1H, phe-H), 8.45 (s, 1H, phe-H), 8.51 (d, J=5.5 Hz, 1H, pyr-H)

R$_t$=16.056 min (0_60_20) (100%) MS+ve: 481.52. .

Method S1

Amide Synthesis

Example I-96

2-{4-[4-(6,8-Dimethyl-1-oxo-1,2,3,4-tetrahydro-pyrrolo[1,2-a]pyrazin-7-yl)-pyrimidin-2-ylamino]-phenyl}-N-(2-methoxy-ethyl)-acetamide

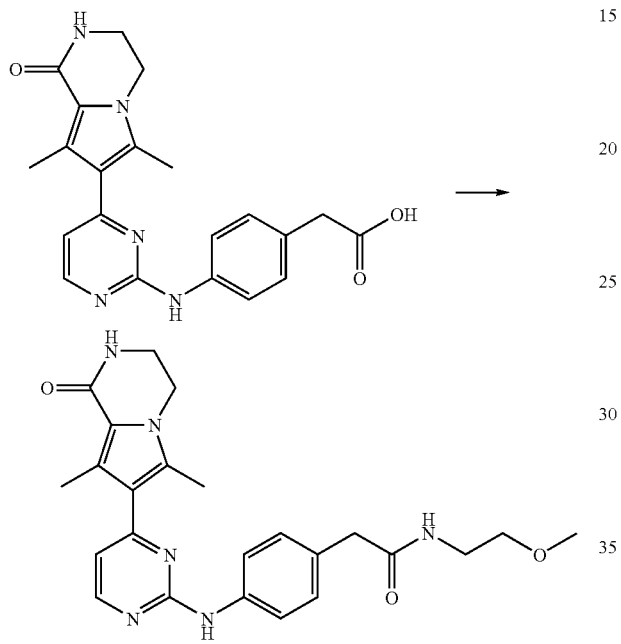

A solution of the pyrimidine acid Example I-70 {4-[4-(6,8-dimethyl-1-oxo-1,2,3,4-tetrahydro-pyrrolo[1,2-a]pyrazin-7-yl)-pyrimidin-2-ylamino]-phenyl}-acetic acid (0.05 g), EDCI (1.2 eq., 0.028 g) and HOBt (1.2 eq., 0.02 g) in THF (3 mL) was stirred at room temperature under nitrogen for 1 hour. 2-Methoxyethylamine (1.2 eq., 0.013 mL) was then added and the resulting reaction stirred at room temperature for 16 hours. Water (5 mL) was added and the solvent removed under vacuum to leave an aqueous suspension which was extracted with dichloromethane (2×2 mL). The combined organics were stripped to yield the crude product as a yellow oil (0.0656 g). Purification of the crude material (prep. HPLC) produced the title compound as a white solid (0.0269 g, 47%, with a purity of 98.37% by LCMS.

Prep. HPLC Lunar C18(2) 5% MeCN in water (0.1% formic acid) to 95% MeCN in water (0.1% formic acid) over 1 hour. Isolation of the product from the prep. HPLC product fractions was achieved by basification (0.5M NaOH, ~2 mL), removal of the solvent under vacuum, extraction of the remaining aqueous with dichloromethane (2×2 mL) and evaporation to give the title compound.

C24H28N6O3 MWt 448.53 (M+1)+ found 449

The following compounds were also prepared from Example I-96 in a similar manner by reaction with an appropriate amine:

Example I-97

N-(2-Dimethylamino-ethyl)-2-{4-[4-(6,8-dimethyl-1-oxo-1,2,3,4-tetrahydro-pyrrolo[1,2-a]pyrazin-7-yl)-pyrimidin-2-ylamino]-phenyl}-N-methyl-acetamide $^1$H NMR D6 dmso 2.13 (6H, s, NMe2); 2.30 (2H, m, —CH2N—); 2.38 (3H, s, —CH3), 2.42 (3H, s, —CH3); 2.82 and 2.96 (2H total, s×2, —CONCH3- rotamers); 3.37 (2H, m, —CONCH2-; 3.59 (2H, s×2, aryl-CH2-CO— rotamers); 3.89 (2H, t J=9.3 Hz, —CH2-); 4.31 (2H, t J-9.3 Hz, —CH2-); 6.77 (1H, d J=5.1 Hz, pyrimidine CH); 7.09 (2H, d J=8.4 Hz, aryl CH); 7.70 (2H, d J=8.4 Hz, aryl CH); 8.35 (1H, d J=5.1 Hz, pyrimidine CH); 9.32 (1H, s, —NH); 11.48 (1H, s, —NH) C26H33N7O2 MWt 475.60 (M+1)+ found 476

Example I-98

N-(3-Dimethylamino-propyl)-2-{4-[4-(6,8-dimethyl-1-oxo-1,2,3,4-tetrahydro-pyrrolo[1,2-a]pyrazin-7-yl)-pyrimidin-2-ylamino]-phenyl}-N-methyl-acetamide C27H35N7O2 MWt 489.63 (M+1)+ found 490

Example I-99

6,8-Dimethyl-7-{2-[4-(2-morpholin-4-yl-2-oxo-ethyl)-phenylamino]-pyrimidin-4-yl}-3,4-dihydro-2H-pyrrolo[1,2-a]pyrazin-1-one C25H28N6O3 MWt 460.54 (M+1)+ found 461

Example I-100

7-(2-{4-[2-(4-Acetyl-piperazin-1-yl)-2-oxo-ethyl]-phenylamino}-pyrimidin-4-yl)-6,8-dimethyl-3,4-dihydro-2H-pyrrolo[1,2-a]pyrazin-1-one C27H31N7O3 MWt 501.59 (M+1)+ found 502

Example I-101

6,8-Dimethyl-7-(2-{4-[2-(4-methyl-piperazin-1-yl)-2-oxo-ethyl]-phenylamino}-pyrimidin-4-yl)-3,4-dihydro-2H-pyrrolo[1,2-a]pyrazin-1-one $^1$H NMR D6 dmso 2.17 (7H, m, piperazine —CH2 and NCH3); 2.38 (3H, s, —CH3); 2.42 (3H, s, CH3); 3.44 (4H, m, piperazine —CH2's); 3.61 (2H, s, arylCH2CO—); 3.89 (2H, t J=9.15 Hz, —CH2); 4.31 (2H, t J=9.15, —CH2); 6.77 (1H, d J=5.1 Hz, pyrimidine CH); 7.09 (2H, d J=8.7 Hz, aryl H); 7.68 (2H, d J=8.7 Hz, aryl H); 8.35 (1H, d J=5.1 Hz, pyrimidine H), 9.32 (1H, s, NH); 11.47 (1H, s, CONH) C26H31N7O2 MWt 473.58 found (M+1)+ 474

Example I-102

2-{4-[4-(6,8-Dimethyl-oxo-1,2,3,4-tetrahydro-pyrrolo[1,2-a]pyrazin-7-yl)-pyrimidin-2-ylamino]-phenyl}-acetamide C21H22N6O2 MWt 390.45 found (M+1)+ 391

Example I-103

2-{4-[4-(6,8-Dimethyl-1-oxo-1,2,3,4-tetrahydro-pyrrolo[1,2-a]pyrazin-7-yl)-pyrimidin-2-ylamino]-phenyl}-N-methyl-acetamide C22H24N6O2 MWt 404.48 found (M+1)+ 405

Example I-104

2-{4-[4-(6,8-Dimethyl-1-oxo-1,2,3,4-tetrahydro-pyrrolo[1,2-a]pyrazin-7-yl)-pyrimidin-2-ylamino]-phenyl}-N,N-dimethyl-acetamide $^1$H NMR D6 dmso 2.38 (3H, s, —CH3), 2.42 (3H, s, —CH3); 2.81 (3H, s, —CONCH3); 2.98 (3H, s, —CONCH3); 3.59 (2H, s, aryl-CH2-CO—); 3.89 (2H, t J=9.3 Hz, —CH2-); 4.31 (2H, t J=9.3 Hz, —CH2-); 6.77 (1H, d J=5.6 Hz, pyrimidine CH); 7.09 (2H, d J=8.4 Hz, aryl CH); 7.68 (2H, d J=8.4 Hz, aryl CH); 8.35 (1H, d J=5.6 Hz, pyrimidine CH); 9.31 (1H, s, —NH); 11.47 (1H, s, —NH) C23H26N6O2 MWt 418.50 found (M+1)+ 419

The following compounds were prepared from Example I-34 3-{3-[4-(6,8-dimethyl-1-oxo-1,2,3,4-tetrahydro-pyrrolo[1,2-a]pyrazin-7-yl)-pyrimidin-2-ylamino]-phenyl}-propionic, acid and the appropriate amine by reaction in a similar manner described above:

Example I-105

3-{3-[4-(6,8-Dimethyl-1-oxo-1,2,3,4-tetrahydro-pyrrolo[1,2-a]pyrazin-7-yl)-pyrlmidin-2-ylamino]-phenyl}-N-(2-methoxy-ethyl)-propionamide C25H30N6O3 MWt 462.56. (M+1)+ found 463

Example I-106

N-(2-Dimethylamino-ethyl)-3-{3-[4-(6,8-dimethyl-1-oxo-1,2,3,4-tetrahydro-pyrrolo[1,2-a]pyrazin-7-yl)-pyrimidin-2-ylamino-]-phenyl}-N-methyl-propionamide C27H35N7O2 MWt 489.63. (M+1)+ found 490

Example I-107

N-(3-Dimethylamino-propyl)-3-{3-[4-(6,8-dimethyl-1-oxo-1,2,3,4-tetrahydro-pyrrolo[1,2-a]pyrazin-7-yl)-pyrimidin-2-ylamino]-phenyl}-N-methyl-propionamide C28H37N7O2 MWt 503.65. (M+1)+ found 504

Example I-108

6,8-Dimethyl-7-{2-[3-(3-morpholin-4-yl-3-oxo-propyl)-phenylamino]-pyrimidin-4-yl}-3,4-dihydro-2H-pyrrolo[1,2-a]pyrazin-1-one C26H30N6O3 MWt 474.57. (M+1)+ found 475

Example I-109

7-(2-{3-[3-(4-Acetyl-piperazin-1-yl)-3-oxo-propyl]-phenylamino}-pyrimidin-4-yl)-6,8-dimethyl-3,4-dihydro-2H-pyrrolo[1,2-a]pyrazin-1-one C28H33N7O3 Mwt 515.62 (M+1)+ found 516

Example I-110

6,8-Dimethyl-7-(2-{3-[3-(4-methyl-piperazin-1-yl)-3-oxo-propyl]-phenylamino}-pyrimidin-4-yl)-3,4-dihydro-2H-pyrrolo[1,2-a]pyrazin-1-one $^1$H NMR D6 dmso 2.13 (3H s, piperazine NMe); 2.19 (4H, m, piperazine —CH2-); 2.39 (3H, s, —CH3), 2.43 (3H, s, —CH3); 2.56 (2H, t J=7.7 Hz, —CH2); 2.75 (2H, t J=7.7 Hz; —CH2); 3.35 (2H, t J=4.87, piperazine —CH2); 3.42 (2H, t J=4.87 Hz, piperazine —CH2); 3.89 (2H, t J=9.2 Hz, —CH2-); 4.31 (2H, t J=9.2 Hz, —CH2-); 6.77 (2H, d J=5.1 Hz, aryl CH pyrimidine CH); 7.09 (2H, d J=8.7 Hz, aryl CH); 7.68 (2H, t J=8.7, aryl CH); 8.35 (1H, d J=5.1 Hz, pyrimidine CH); 9.32 (1H, s, —NH); 11.47 (1H, s, —NH) C27H33N7O2 MWt 487.61 (M+1)+ found 488

Example I-111

3-{3-[4-(6,8-Dimethyl-1-oxo-1,2,3,4-tetrahydro-pyrrolo[1,2-a]pyrazin-7-yl)-pyrimidin-2-ylamino]-phenyl}-propionamide C22H24N6O2 Mwt 404.48 (M+1)+ found 405

Example I-112

3-{3-[4-(6,8-Dimethyl-1-oxo-1,2,3,4-tetrahydro-pyrrolo[1,2-a]pyrazin-7-yl)-pyrimidin-2-ylamino]-phenyl}-N-methyl-propionamide C23H26N6O2 MWt 418.50 (M+1)+ found 419

Example I-113

3-{3-[4-(6,8-Dimethyl-1-oxo-1,2,3,4-tetrahydro-pyrrolo[1,2-a]pyrazin-7-yl)-pyrimidin-2-ylamino]-phenyl}-N,N-dimethyl-propionamide $^1$H NMR D6 dmso 2.39 (3H, s, —CH3), 2.43 (3H, s, —CH3); 2.55 (2H, t J=7.7 Hz, —CH2); 2.74 (2H, t J=7.7 Hz; —CH2); 2.80 (3H, s, NMe); 2.91 (3H, s, NMe); 3.89 (2H, t J=9.3 Hz, —CH2-); 4.31 (2H, t J=9.3 Hz, —CH2-); 6.78 (2H, m aryl CH and pyrimidine CH); 7.15 (1H, t J 7.95, aryl CM); 7.61 (2H, m, aryl CM); 8.36 (1H, d J=5.4 Hz, pyrimidine CH); 9.29 (1H, s, —NH); 11.47 (1H, s, —NH) C24H28N6O2 MWt 432.53 (M+1)+ found 433

Method S2

By reaction of Example I-27 4-[4-(6,8-Dimethyl-1-oxo-1,2,3,4-tetrahydro-pyrrolo[1,2-a]pyrazin-7-yl)-pyrimidin-2-ylamino]-3-methoxy-benzoic acid and 4-amino-1-methylpiperidine as described above but using TBTU as the coupling agent.

Example I-114

4-[4-(6,8-Dimethyl-1-oxo-1,2,3,4-tetrahydro-pyrrolo[1,2-a]pyrazin-7-yl)-pyrimidin-2-ylamino]-3-methoxy-N-(1-methyl-piperidin-4-yl)-benzamide $^1$H NMR CDCl$_3$: 1.53 (2H, m, piperidine CH); 1.98 (2H, m, piperidine CH); 2.11 (2H, m, piperidine CH); 2.24 (3H, s, NCH3); 2.41 (3H, s, CH3); 2.43 (3H, s, CH3); 2.76 (2H, m, piperidine CH); 3.91 (3H, s, OCH3); 3.94 (3H, m, —NCH2- & piperidine NCH); 4.33 (2H, t, J=9.3 Hz —NCH2-); 5.91 (1H, d, J=8.0 Hz, CHNHCO); 6.72 (1H, d, J=4.5 Hz, pyrimidine H); 7.18 (1H, d, J=8.5 Hz, aryl CH); 7.39 (1H, s, aryl CH); 7.85 (1H, s, NHAr), 8.34 (1H, d, J=4.0 Hz, pyrimidine CH); 8.61 (1H, d, I=8.5 Hz, aryl CH) C27H33N7O3 MWt=503.61. [M+1]+ found 504. Anal. HPLC Rt 12.75 min (0-60-20)

By reaction of Example I-26 4-[4-(6,8-dimethyl-1-oxo-1,2,3,4-tetrahydro-pyrrolo[1,2-a]pyrazin-7-yl)-pyrimidin-2-ylamino]-benzoic acid and 4-amino-1-methylpiperidine as described above but using TBTU as the coupling agent.

Example I-115

4-[4-(6,8-Dimethyl-1-oxo-1,2,3,4-tetrahydro-pyrrolo[1,2-a]pyrazin-7-yl)-pyrimidin-2-ylamino]-N-(1-methyl-piperidin-4-yl)-benzamide $^1$H NMR CDCl$_3$: 1.54 (2H, m, piperidine CH); 1.98 (2H, m, piperidine CH); 2.12 (2H, m, piperidine CH); 2.25 (3H, s, NCH3); 2.36 (3H, s, CH3); 2.43 (3H, s, CH3); 2.79 (2H, m, piperidine CH); 3.92 (3H, m, —NCH2- & piperidine NCH); 4.33 (2H, t, J=9.3 Hz —NCH2-); 5.94 (1H, d, J=8.0 Hz, CHNHCO); 6.74 (1H, d, J=5 Hz, pyrimidine H); 7.63 (1H, s, NHAr), 7.67 (4H, m, aryl CH), 8.33 (1H, d, J=5 Hz, pyrimidine CH); C26H31N7O2 MWt=473.57 [M-113]+ fragment found 360; Anal. HPLC Rt=9.04 min (10-70-20)

Kinase Assays

The compounds of the invention above were investigated for their ability to inhibit the enzymatic activity of various protein kinases. This was achieved by measurement of incorporation of radioactive phosphate from ATP into appropriate polypeptide substrates. Recombinant protein kinases and kinase complexes were produced or obtained commercially. Assays were performed using 96-well plates and appropriate assay buffers (typically 25 mM β-glycerophosphate, 20 mM MOPS, 5 mM EGTA, 1 mM DTT, 1 mM Na$_3$VO$_3$, pH 7.4), into which were added 2-4 μg of active enzyme with appropriate substrates. The reactions were initiated by addition of Mg/ATP mix (15 mM MgCl$_2$+100 μM ATP with 30-50 kBq per well of [γ-$^{32}$P]-ATP) and mixtures incubated as required at 30° C. Reactions were stopped on ice, followed by filtration through p81 filterplates or GF/C filterplates (Whatman Polyfiltronics, Kent, UK). After washing 3 times with 75 mM aq orthophosphoric acid, plates were dried, scintillant added and incorporated radioactivity measured in a scintillation counter (TopCount, Packard Instruments, Pangbourne, Berks, UK). Compounds for kinase assay were made up as 10 mM stocks in DMSO and diluted into 10% DMSO in assay buffer. Data was analysed using curve-fitting software (GraphPad Prism version 3.00 for Windows, GraphPad Software, San Diego Calif. USA) to determine IC$_{50}$ values (concentration of test compound which inhibits kinase activity by 50%).

CDK 7 and 9 Assays

CTD peptide substrate (biotinyl-Ahx-(Tyr-Ser-Pro-Thr-Ser-Pro-Ser)$_4$-NH$_2$; 1-2 mg/mL) and recombinant human CDK7/cyclin H, CDK9/cyclin T1, or CDK9/cyclin K (0.5-2 μg) were incubated for 45 min at 30° C. in the presence of varying amounts of test compound in 20 mM MOPS pH 7.2, 25 mM β-glycerophosphate, 5 mM EGTA, 1 mM DTT, 1 mM sodium vanadate, 15 mM MgCl$_2$, and 100 μM ATP (containing a trace amount of $^{32}$PγATP) in a total volume of 25 μL in a 96-well microtiter plate. The reaction was stopped by placing the plate on ice for 2 min. Avidin (50 μg) was added- to each well, and the plate was incubated at room temp for 30 min. The samples were transferred to a 96-well P81 filter plate, and washed (4×200 μL per well) with 75 mM phosphoric acid. Microscint 40 scintillation liquid (50 μL) was added to each well, and the amount of $^{32}$P incorporation for each sample was measured using a Packard Topcount microplate scintillation counter.

Aurora-A (Human) Kinase Assay

This was achieved by measurement of incorporation of radioactive phosphate from ATP into Kemptide substrate (LRRASLG), upon phosphorylation by commercially obtained aurora-A (human, Upstate; Dundee, UK). Assays were performed using 96-well plates and appropriate assay buffers (20 mM Tris, 25 mM β-glycerophosphate, 5 mM EGTA, 1 mM DTT, 1 mM sodium vanadate, pH 7.5), into which were added 2-5 ng of active enzyme with 500 μM substrate (Kemptide). The reactions were initiated by addition of MATP mix (15 mM MgCl$_2$+100 μM ATP with 15-25 kBq per well of [γ-$^{32}$P]-ATP) and mixtures incubated for 30 min at 30° C. Reactions were stopped by addition of an equal volume of 75 mM aq orthophosphoric acid, followed by filtration through p81 filterplates (Whatman Polyfiltronics, Kent, UK). After washing 4 times with 75 mM aq orthophosphoric acid, plates were dried, scintillant added and incorporated radioactivity measured in a scintillation counter (TopCount, Packard Instruments, Pangbourne, Berks, UK). Compounds for kinase assay were made up as 10 mM stocks in DMSO and diluted into 10% DMSO in assay buffer. Data was analysed using curve-fitting software (XLfit version 4.0.2, IDBS, Guildford, Surrey, UK) to determine IC$_{50}$ values (concentration of test compound which inhibits kinase activity by 50%).

Aurora-B (Human) Kinase Assay

This was achieved by measurement of incorporation of radioactive phosphate from ATP into Kemptide substrate (LRRASLG), upon phosphorylation by commercially obtained aurora-B (human, Upstate, Dundee, UK). Assays were performed using 96-well plates and appropriate assay buffers (20 mM Tris, 25 mM O-glycerophosphate, 5 mM EGTA, 1M DTT, 1 mM sodium vanadate, pH 7.5), into which were added 75 ng of pre-activated enzyme with 500 μM substrate (Kemptide). The reactions were initiated by addition of MgATP mix (15 mM MgCl$_2$+100 μM ATP with 15-25 kBq per well of [γ-$^{32}$P]-ATP) and mixtures incubated for 60 min at 30° C. Reactions were stopped by addition of an equal volume of 75 mM aq orthophosphoric acid, followed by filtration through p81 filterplates (Whatman Polyfiltronics, Kent, UK). After washing 4 times with 75 mM aq orthophosphoric acid, plates were dried, scintillant added and incorporated radioactivity measured in a scintillation counter (TopCount, Packard Instruments, Pangbourne, Berks, UK). Compounds for kinase assay were made up as 10 mM stocks in DMSO and diluted into 10% DMSO in assay buffer. Data was analysed using curve-fitting software (XLfit version 4.0.2, IDBS, Guildford, Surrey, UK) to determine IC$_{50}$ values (concentration of test compound which inhibits kinase activity by 50%).

Pre-Activation of Aurora-B (Human)

Aurora-B (human, Upstate, Dundee, UK) was pre-activated immediately prior to kinase assay in appropriate buffers (20 mM Tris, 25 mM β-glycerophosphate, 5 mM EGTA, 1 mM DTT, 1 mM sodium vanadate, pH 7.5) by incubating 15 µg of enzyme with 4 µg INCENP (Upstate, Dundee, UK) in the presence of MgATP mix (15 mM $MgCl_2$+100 µM ATP) for 15 min at 30° C.

Flt3 Kinase Assay

This was achieved by measurement of incorporation of radioactive phosphate from ATP into myelin basic protein (MBP) substrate, upon phosphorylation by commercially obtained Flt-3 (Upstate, Dundee, UK). Assays were performed using 96-well plates and appropriate assay buffers (20 mM Tris, 25 mM β-glycerophosphate, 5 mM EGTA, 1 mM DTT, 1 mM sodium vanadate, pH 7.5), into which were added 5 ng of active enzyme with 0.4 mg/ml substrate (MBP). The reactions were initiated by addition of MgATP mix (15 mM $MgCl_2$+100 µM ATP with 15-25 kBq per well of [γ-$^{32}$P]-ATP) and mixtures incubated for 30 min at 30° C. Reactions were stopped by addition of an equal volume of 75 mM aq orthodophosphoric acid, followed by filtration through p81 filterplates (Whatman Polyfiltronics, Kent, UK). After washing 4 times with 75 mM aq orthophosphoric acid, plates were dried, scintillant added and incorporated radioactivity measured in a scintillation counter (TopCount, Packard Instruments, Pangbourne, Berks, UK). Compounds for kinase assay were made up as 10 mM stocks in DMSO and diluted into 10% DMSO in assay buffer. Data was analysed using curve-fitting software (XLfit version 4.0.2, IDBS, Guildford, Surrey, UK) to determine $IC_{50}$ values (concentration of test compound which inhibits kinase activity by 50%).

MTT Cytotoxicity Assay

The compounds of the invention were subjected to a standard cellular proliferation assay using cell lines A2870 and MiaPaCa (obtained from The European Collection of Cell Cultures). Standard 72-h MTT (thiazolyl blue; 3-[4,5-dimethylthiazol-2-yl]-2,5-diphenyltetrazolium bromide) assays were performed (Haselsberger, K.; Peterson, D. C.; Thomas, D. G.; Darling, J. L. Anti Cancer Drugs 1996, 7, 331-8; Loveland, B. E.; Johns, T. G.; Mackay, I. R.; Vaillant, F.; Wang, Z. X.; Hertzog, P. J. Biochemistry International 1992, 27, 501-10). In short: cells were seeded into 96-well plates according to doubling time and incubated overnight at 37° C. Test compounds were made up in DMSO and a 1/3 dilution series prepared in 100 µL cell media, added to cells (in triplicates) and incubated for 72 ho at 37° C. MTT was made up as a stock of 5 mg/mL in cell media and filter-sterilised. Media was removed from cells followed by a wash with 200 µL PBS. MTT solution was then added at 20 µL per well and incubated in the dark at 37° C. for 4 h. MTT solution was removed and cells again washed with 200 µL PBS. MT dye was solubilised with 200 mL per well of DMSO with agitation. Absorbance was read at 540 nm and data analysed using curve-fitting software (GraphPad Prism version 3.00 for Windows, GraphPad Software, San Diego Calif. USA) to determine $IC_{50}$ values (concentration of test compound which inhibits cell growth by 50%).

In vitro kinase and cytotoxicity data for selected compounds of the invention are shown in Tables 1, 2 and 3. Aurora A activity is denoted by a grading system: * means less than 0.1 µM $IC_{50}$;  means less than 1.0 µM $IC_{50}$; * means less than 10 µM $IC_{50}$.

Cellomics Arrayscan Assays for Mitotic Index (EH3 and MPM2 Staining)

The percentage of cells with nuclear phospho-Histone H3 and/or MPM2 staining were determined in 96-well plate assays using the Cellomics Arrayscan Mitotic Index HitKit protocol (Cellomics Inc). Briefly, cells were plated at $10^4$ cells per well and incubated for 16-18 h at 37° C. Compounds were added and the cells incubated for the appropriate time before a 15 min fixation in 3.7% formaldehyde in wash buffer (Cellomics Inc.). Cells were permeabilised in 0.2% Triton in wash buffer for 15 min, washed, then incubated with primary antibodies that specifically recognise mitotic epitopes; rabbit anti-phosphohistone H3 (Upstate 06570) or mouse anti-phospho-Ser/Thr-Pro MPM2 (Upstate 05-368). After a 1 h incubation cells were washed and incubated with secondary FITC-conjugated anti-mouse and/or TRITC-conjugated anti-rabbit secondary antibodies (Jackson laboratories) and Hoescht dye. After a further 1 h incubation the cells were washed, then the plate was analysed using a Cellomics Arrayscan II automated fluorescent microscopy system to detect nuclear fluorescent staining. Data for 2000 cells per well were stored and the percentage of cells expressing mitotic epitopes compared to total cells (stained with Hoescht dye) was calculated using the Cellomics mitotic index algorithm. The data are shown in Table 2 below.

Various modifications and variations of the described aspects of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the relevant fields are intended to be within the scope of the following claims.

TABLE 1

In vitro kinase data for selected compounds of the invention (Ki, µM)

| Compound | CDK2/E | CDK7/H | CDK9/T1 |
|---|---|---|---|
| I.1 | 1.13 | 2.99 | — |
| I.2 | — | 3.41 | — |
| I.3 | — | 2.79 | — |

TABLE 2

Cytotoxicity data for selected compounds of the invention

| | MI (Cellomics) | | 96-h MTT | |
| | PH3/MPM2 | MPM2 % of | IC50 (µM) | |
| Compound | IC50* (µM) | Control** | A2780 | MiaPaCa |
|---|---|---|---|---|
| I.1 | 16.28 | 239 | 4.47 | >10 |
| I.2 | 9.2 | 333 | 0.575 | 1.8 |
| I.3 | 4.74 | 317 | 0.75 | 1.85 |

*PH3/MPM2 IC50 of phosphorylated Histone H3 staining normalised using MPM2 staining
**MPM2 - % of control - cells stained with MPM2 Ab after treatment with inhibitors calculated as % of MPM2 stained cells treated with only the vehicle (DMSO).

TABLE 3

Structures and biological activity of compounds in accordance with the invention;

| No. | Structure | Activity | Method |
|---|---|---|---|
| I-1 | 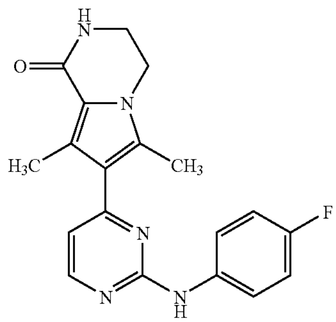 [SMILES: Cc1c(-c2ccnc(Nc3ccc(F)cc3)n2)c(C)n2c1C(=O)NCC2] | ** | A |
| I-2 | 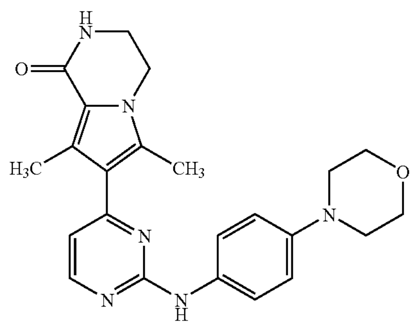 [SMILES: Cc1c(-c2ccnc(Nc3ccc(N4CCOCC4)cc3)n2)c(C)n2c1C(=O)NCC2] | ** | A |
| I-3 | 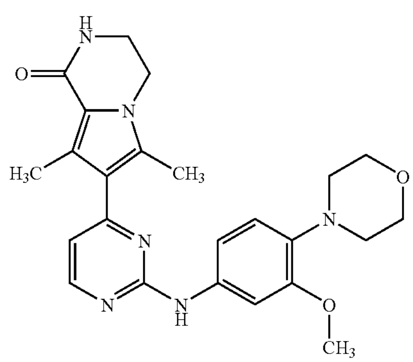 [SMILES: COc1cc(Nc2nccc(-c3c(C)c4n(c3C)CCNC4=O)n2)ccc1N1CCOCC1] | *** | A |
| I-4 | 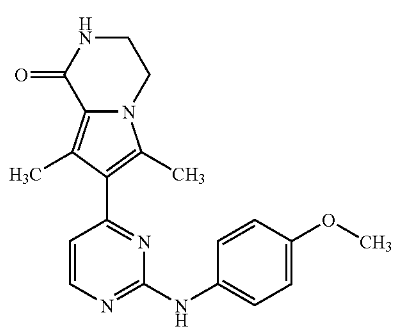 [SMILES: COc1ccc(Nc2nccc(-c3c(C)c4n(c3C)CCNC4=O)n2)cc1] | ** | A |

TABLE 3-continued

Structures and biological activity of compounds in accordance with the invention;

| No. | Structure | Activity | Method |
|---|---|---|---|
| I-5 | 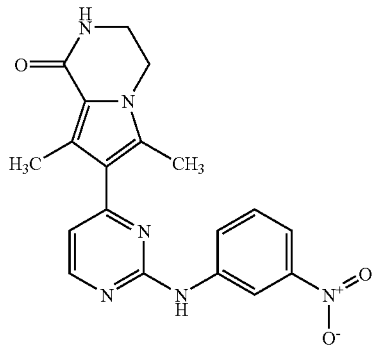 [SMILES: Cc1c(-c2ccnc(Nc3cccc([N+](=O)[O-])c3)n2)c(C)n2c1C(=O)NCC2] | ** | A |
| I-6 | 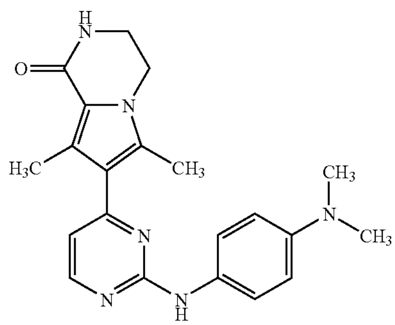 [SMILES: Cc1c(-c2ccnc(Nc3ccc(N(C)C)cc3)n2)c(C)n2c1C(=O)NCC2] | ** | A |
| I-7 | 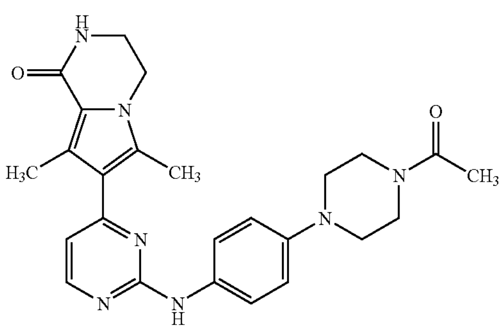 [SMILES: CC(=O)N1CCN(c2ccc(Nc3nccc(-c4c(C)c5n(c4C)CCNC5=O)n3)cc2)CC1] | ** | A |
| I-8 | 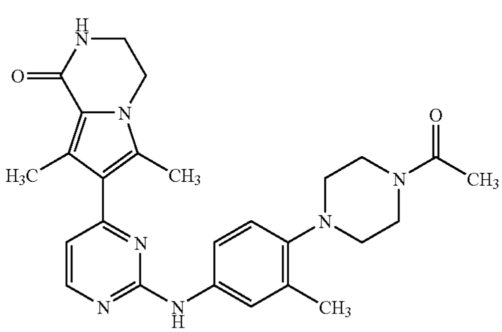 [SMILES: CC(=O)N1CCN(c2ccc(Nc3nccc(-c4c(C)c5n(c4C)CCNC5=O)n3)cc2C)CC1] | ** | A |

TABLE 3-continued

Structures and biological activity of compounds in accordance with the invention;

| No. | Structure | Activity | Method |
|-----|-----------|----------|--------|
| I-9 | 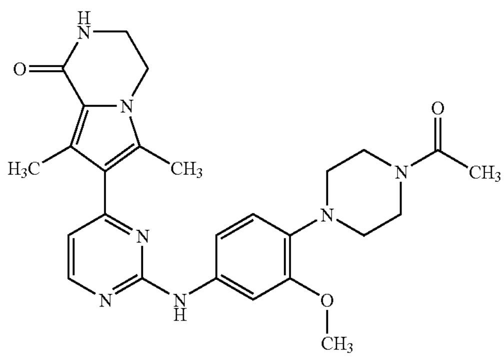 [SMILES: COc1cc(Nc2nccc(-c3c(C)c4n(c3C)CCNC4=O)n2)ccc1N1CCN(C(C)=O)CC1] | ** | A |
| I-10 | 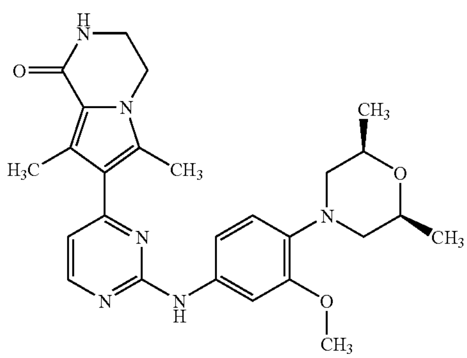 [SMILES: COc1cc(Nc2nccc(-c3c(C)c4n(c3C)CCNC4=O)n2)ccc1N1C[C@@H](C)O[C@@H](C)C1] | ** | A |
| I-11 | 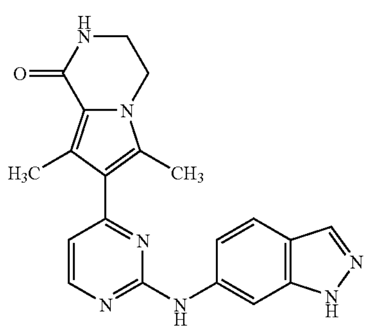 [SMILES: Cc1c(-c2ccnc(Nc3ccc4cn[nH]c4c3)n2)c(C)n2c1C(=O)NCC2] | ** | A |
| I-12 | 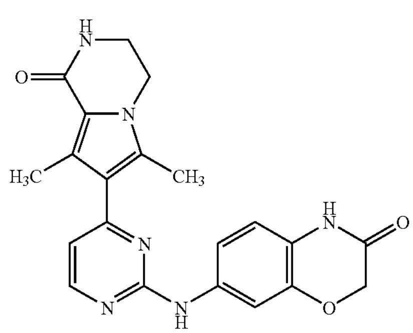 [SMILES: Cc1c(-c2ccnc(Nc3ccc4c(c3)OCC(=O)N4)n2)c(C)n2c1C(=O)NCC2] | ** | A |

TABLE 3-continued

Structures and biological activity of compounds in accordance with the invention;

| No. | Structure | Activity | Method |
|---|---|---|---|
| I-13 | 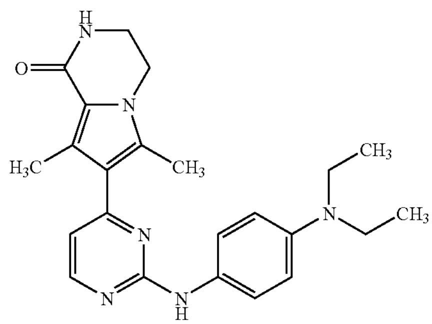 [SMILES: CCN(CC)c1ccc(Nc2nccc(-c3c(C)c4n(c3C)CCNC4=O)n2)cc1] | ** | A |
| I-13a | 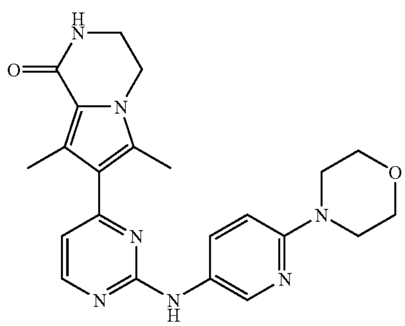 [SMILES: Cc1c(-c2ccnc(Nc3ccc(N4CCOCC4)nc3)n2)c(C)n2c1C(=O)NCC2] | ** | A |
| I-13b | 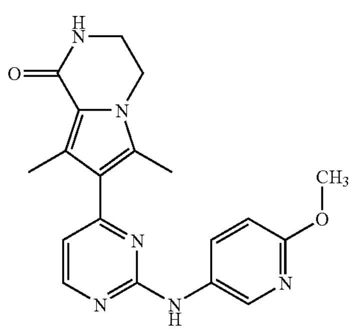 [SMILES: COc1ccc(Nc2nccc(-c3c(C)c4n(c3C)CCNC4=O)n2)cn1] | ** | B |
| I-14 | 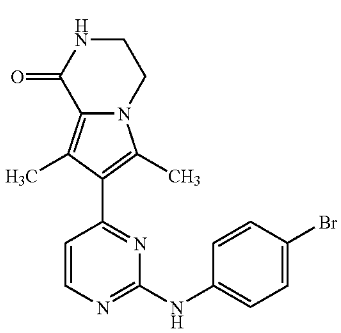 [SMILES: Cc1c(-c2ccnc(Nc3ccc(Br)cc3)n2)c(C)n2c1C(=O)NCC2] | ** | B |

TABLE 3-continued

Structures and biological activity of compounds in accordance with the invention;

| No. | Structure | Activity | Method |
|-----|-----------|----------|--------|
| I-15 | 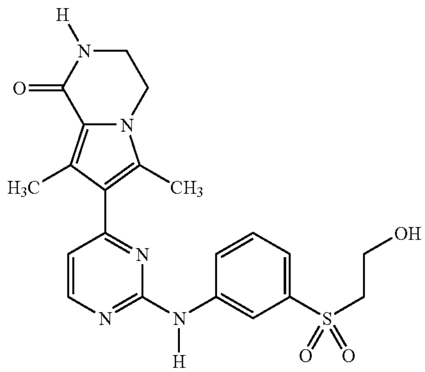 [SMILES: Cc1c(-c2ccnc(Nc3cccc(S(=O)(=O)CCO)c3)n2)c(C)n2c1C(=O)NCC2] | ** | B |
| I-16 | 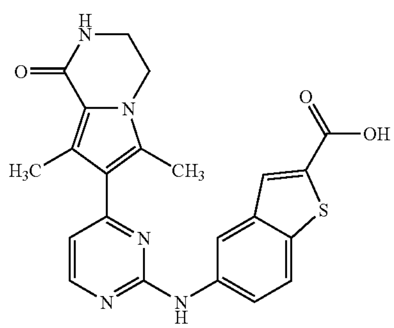 [SMILES: Cc1c(-c2ccnc(Nc3ccc4sc(C(=O)O)cc4c3)n2)c(C)n2c1C(=O)NCC2] | *** | B |
| I-17 | 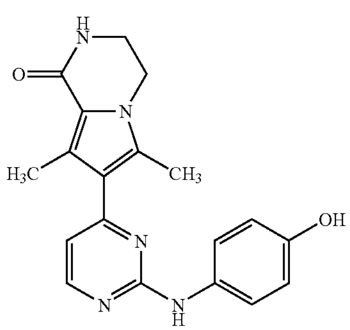 [SMILES: Cc1c(-c2ccnc(Nc3ccc(O)cc3)n2)c(C)n2c1C(=O)NCC2] | ** | B |
| I-18 | 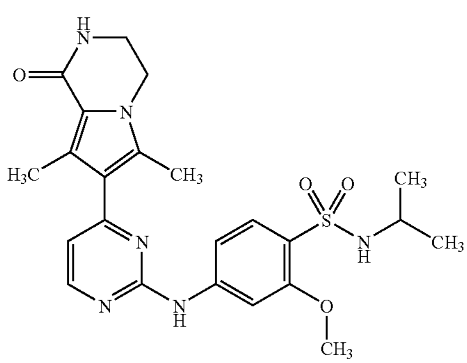 [SMILES: COc1cc(Nc2nccc(-c3c(C)c4n(c3C)CCNC4=O)n2)ccc1S(=O)(=O)NC(C)C] | *** | B |

TABLE 3-continued

Structures and biological activity of compounds in accordance with the invention;

| No. | Structure | Activity | Method |
|-----|-----------|----------|--------|
| I-19 | 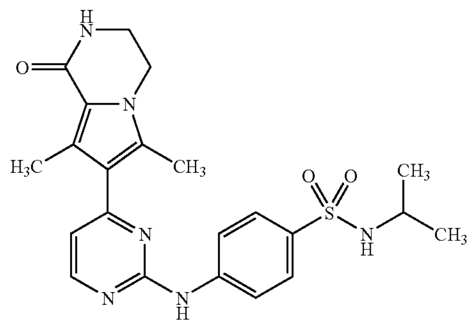 [SMILES: Cc1c(-c2ccnc(Nc3ccc(S(=O)(=O)NC(C)C)cc3)n2)c(C)n2c1C(=O)NCC2] | ** | B |
| I-20 | 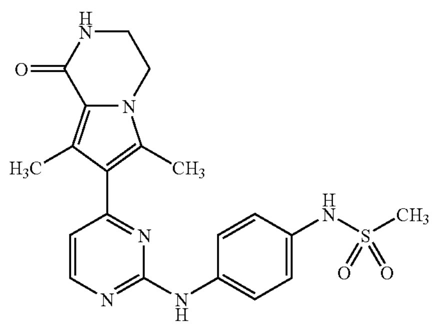 [SMILES: Cc1c(-c2ccnc(Nc3ccc(NS(C)(=O)=O)cc3)n2)c(C)n2c1C(=O)NCC2] | ** | B |
| I-21 | 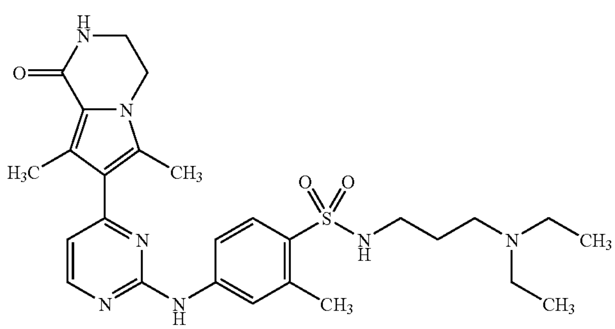 [SMILES: CCN(CC)CCCNS(=O)(=O)c1ccc(Nc2nccc(-c3c(C)c4n(c3C)CCNC4=O)n2)cc1C] | * | B |
| I-22 | 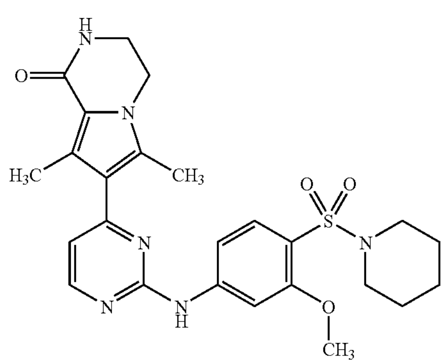 [SMILES: COc1cc(Nc2nccc(-c3c(C)c4n(c3C)CCNC4=O)n2)ccc1S(=O)(=O)N1CCCCC1] | ** | B |

TABLE 3-continued

Structures and biological activity of compounds in accordance with the invention;

| No. | Structure | Activity | Method |
|---|---|---|---|
| I-23 | 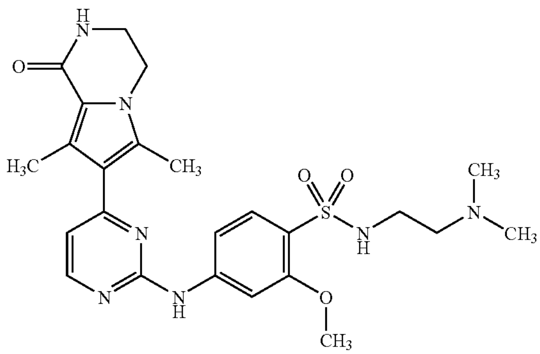 [SMILES: COc1cc(Nc2nccc(-c3c(C)c4n(c3C)CCNC4=O)n2)ccc1S(=O)(=O)NCCN(C)C] | ** | B |
| I-24 | 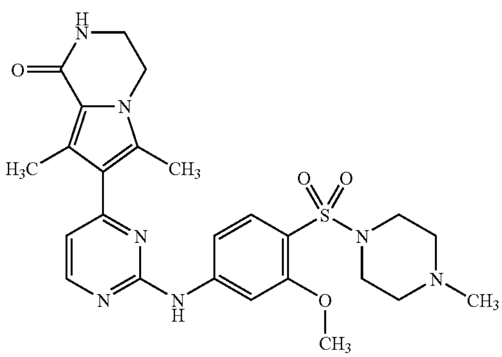 [SMILES: COc1cc(Nc2nccc(-c3c(C)c4n(c3C)CCNC4=O)n2)ccc1S(=O)(=O)N1CCN(C)CC1] | ** | B |
| I-25 | 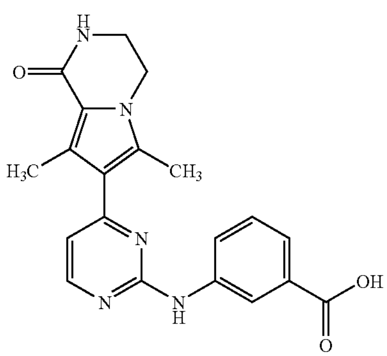 [SMILES: Cc1c(-c2ccnc(Nc3cccc(C(=O)O)c3)n2)c(C)n2c1C(=O)NCC2] | ** | B |
| I-26 | 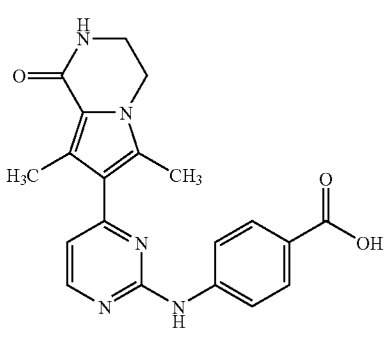 [SMILES: Cc1c(-c2ccnc(Nc3ccc(C(=O)O)cc3)n2)c(C)n2c1C(=O)NCC2] | *** | B |

TABLE 3-continued
Structures and biological activity of compounds in accordance with the invention;
| No. | Structure | Activity | Method |
|---|---|---|---|
| I-27 | 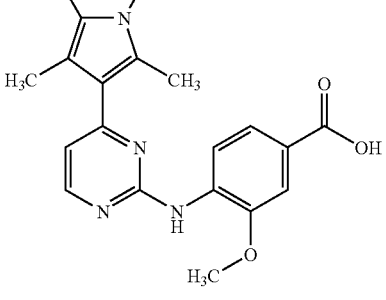 | ** | B |
| I-28 | 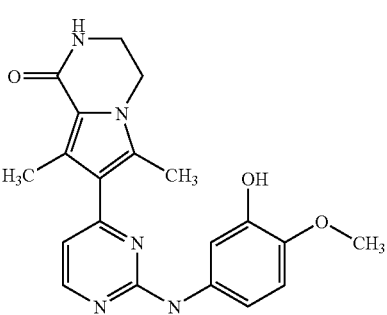 | ** | B |
| I-29 | 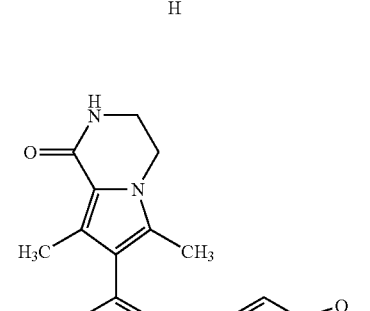 | ** | B |
| I-30 | 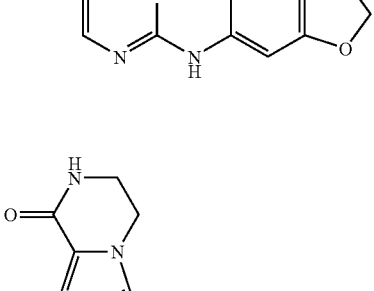 | * | B |

TABLE 3-continued

Structures and biological activity of compounds in accordance with the invention;

| No. | Structure | Activity | Method |
|---|---|---|---|
| I-31 | 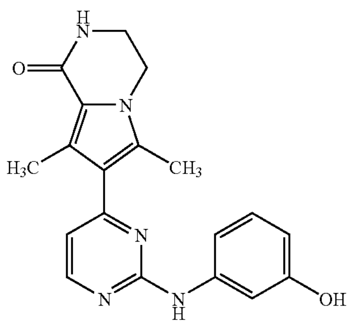 [SMILES: Cc1c(-c2ccnc(Nc3cccc(O)c3)n2)c(C)n2c1C(=O)NCC2] | ** | B |
| I-32 | 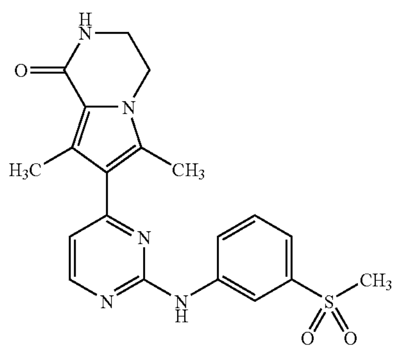 [SMILES: Cc1c(-c2ccnc(Nc3cccc(S(C)(=O)=O)c3)n2)c(C)n2c1C(=O)NCC2] | *** | B |
| I-33 | 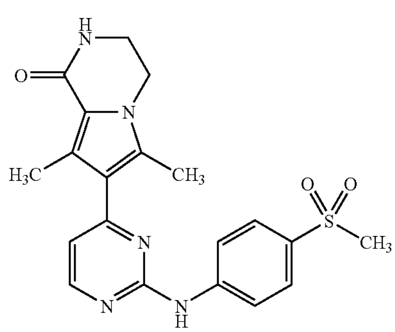 [SMILES: Cc1c(-c2ccnc(Nc3ccc(S(C)(=O)=O)cc3)n2)c(C)n2c1C(=O)NCC2] | *** | B |
| I-34 | 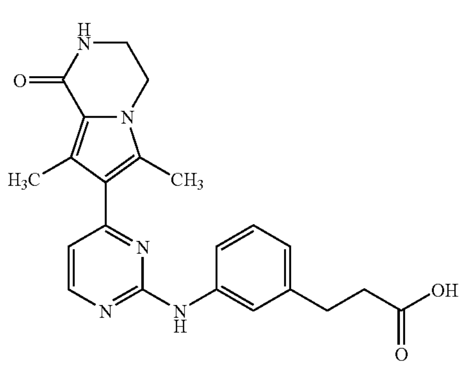 | *** | B |

TABLE 3-continued

Structures and biological activity of compounds in accordance with the invention;

| No. | Structure | Activity | Method |
|---|---|---|---|
| I-35 | 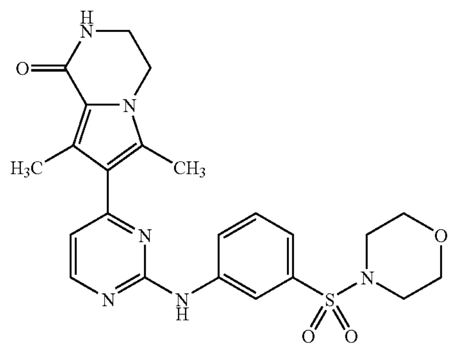 [SMILES: Cc1c(-c2ccnc(Nc3cccc(S(=O)(=O)N4CCOCC4)c3)n2)c(C)n2c1C(=O)NCC2] | ** | B |
| I-36 | 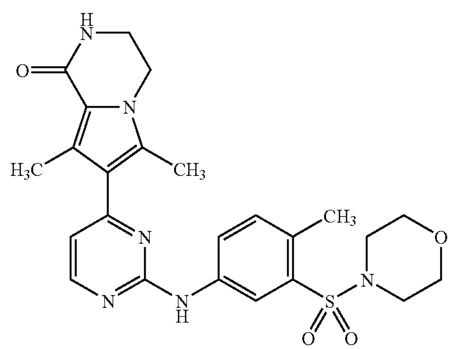 [SMILES: Cc1ccc(Nc2nccc(-c3c(C)c4n(c3C)CCNC4=O)n2)cc1S(=O)(=O)N1CCOCC1] | ** | B |
| I-37 | 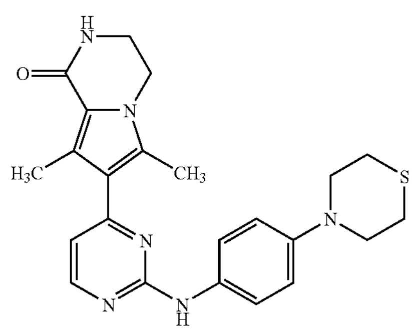 [SMILES: Cc1c(-c2ccnc(Nc3ccc(N4CCSCC4)cc3)n2)c(C)n2c1C(=O)NCC2] | ** | B |
| I-38 | 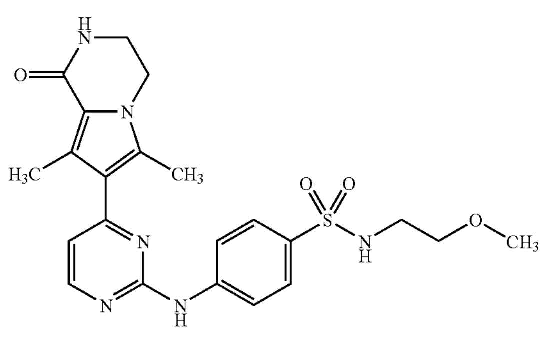 [SMILES: COCCNS(=O)(=O)c1ccc(Nc2nccc(-c3c(C)c4n(c3C)CCNC4=O)n2)cc1] | ** | B |

TABLE 3-continued

Structures and biological activity of compounds in accordance with the invention;

| No. | Structure | Activity | Method |
|---|---|---|---|
| I-39 | 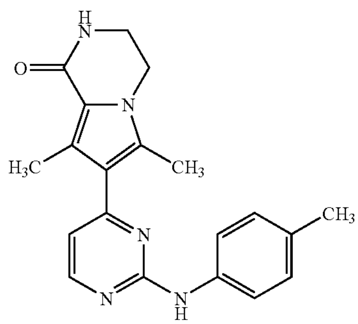 [SMILES: Cc1ccc(Nc2nccc(-c3c(C)c4n(c3C)CCNC4=O)n2)cc1] | ** | B |
| I-40 | 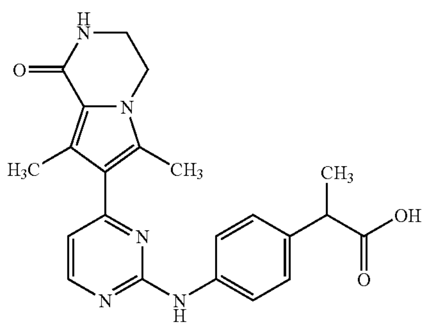 [SMILES: Cc1c(-c2ccnc(Nc3ccc(C(C)C(=O)O)cc3)n2)c(C)n2c1C(=O)NCC2] | ** | B |
| I-41 | 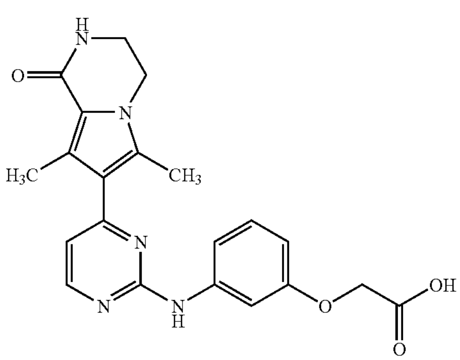 [SMILES: Cc1c(-c2ccnc(Nc3cccc(OCC(=O)O)c3)n2)c(C)n2c1C(=O)NCC2] | *** | B |
| I-42 | 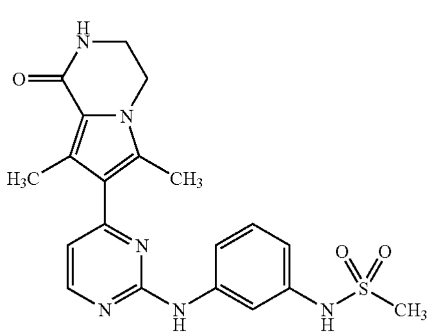 [SMILES: Cc1c(-c2ccnc(Nc3cccc(NS(C)(=O)=O)c3)n2)c(C)n2c1C(=O)NCC2] | ** | B |

TABLE 3-continued

Structures and biological activity of compounds in accordance with the invention;

| No. | Structure | Activity | Method |
|---|---|---|---|
| I-43 | 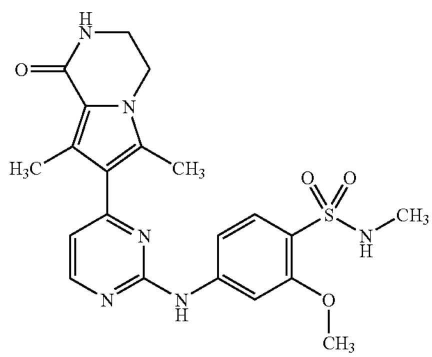 [SMILES: CNS(=O)(=O)c1ccc(Nc2nccc(-c3c(C)c4n(c3C)CCNC4=O)n2)cc1OC] | ** | B |
| I-44 | 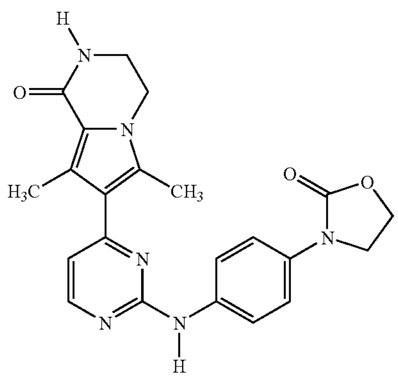 [SMILES: Cc1c(-c2ccnc(Nc3ccc(N4CCOC4=O)cc3)n2)c(C)n2c1C(=O)NCC2] | ** | B |
| I-45 | 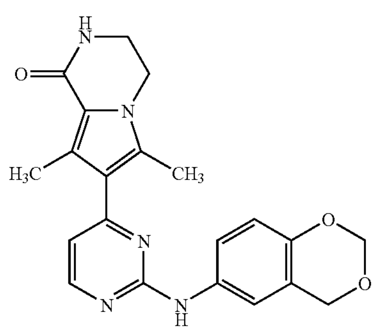 [SMILES: Cc1c(-c2ccnc(Nc3ccc4c(c3)COCO4)n2)c(C)n2c1C(=O)NCC2] | *** | B |
| I-46 | 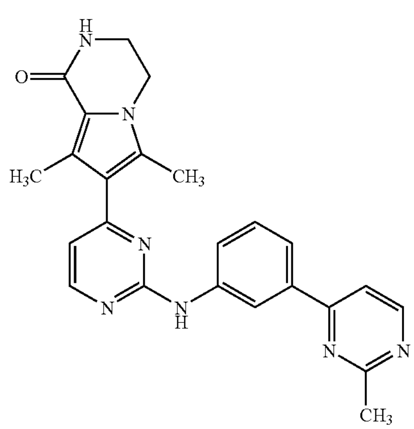 [SMILES: Cc1nccc(-c2cccc(Nc3nccc(-c4c(C)c5n(c4C)CCNC5=O)n3)c2)n1] | *** | B |

TABLE 3-continued
Structures and biological activity of compounds in accordance with the invention;
| No. | Structure | Activity | Method |
|---|---|---|---|
| I-47 | 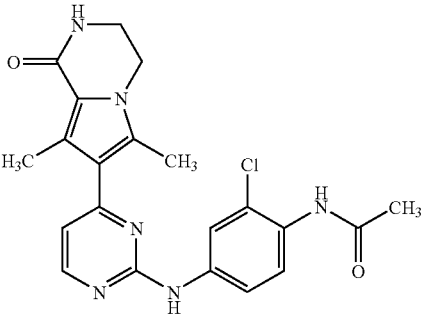 [SMILES: CC(=O)Nc1ccc(Nc2nccc(-c3c(C)c4n(c3C)CCNC4=O)n2)cc1Cl] | ** | B |
| I-48 | 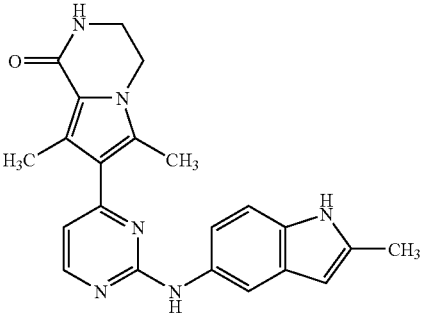 [SMILES: Cc1cc2cc(Nc3nccc(-c4c(C)c5n(c4C)CCNC5=O)n3)ccc2[nH]1] | ** | B |
| I-49 | 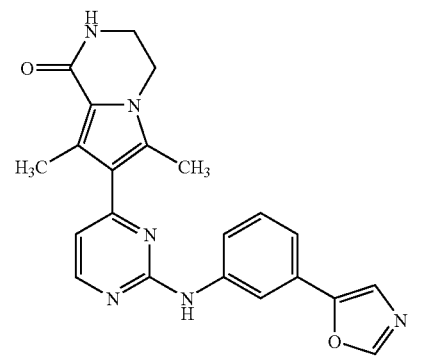 [SMILES: Cc1c(-c2ccnc(Nc3cccc(-c4cnco4)c3)n2)c(C)n2c1C(=O)NCC2] | ** | B |
| I-50 | 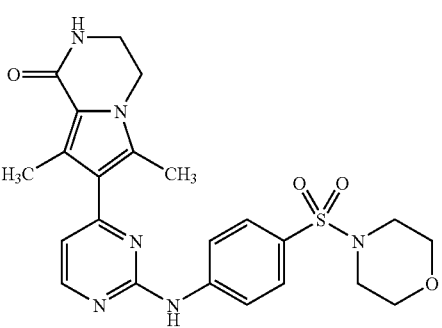 [SMILES: Cc1c(-c2ccnc(Nc3ccc(S(=O)(=O)N4CCOCC4)cc3)n2)c(C)n2c1C(=O)NCC2] | ** | B |

TABLE 3-continued

Structures and biological activity of compounds in accordance with the invention;

| No. | Structure | Activity | Method |
|---|---|---|---|
| I-51 | 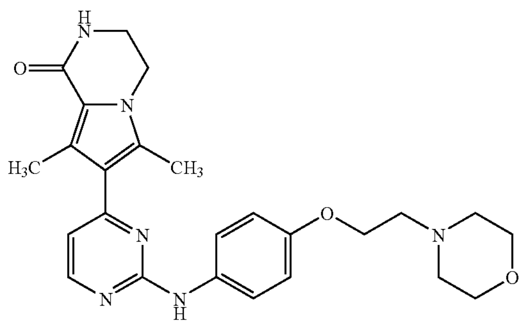 [SMILES: Cc1c(-c2ccnc(Nc3ccc(OCCN4CCOCC4)cc3)n2)c(C)n2c1C(=O)NCC2] | ** | B |
| I-52 | 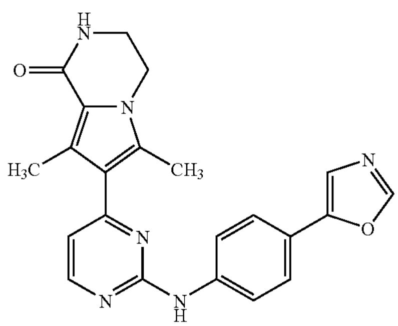 [SMILES: Cc1c(-c2ccnc(Nc3ccc(-c4cnco4)cc3)n2)c(C)n2c1C(=O)NCC2] | ** | B |
| I-53 | 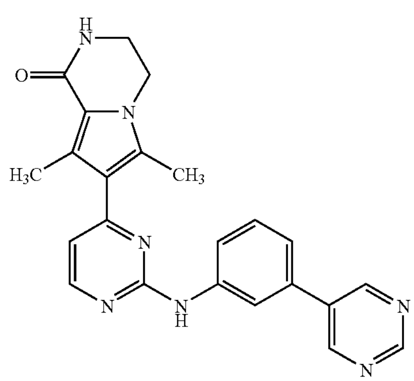 [SMILES: Cc1c(-c2ccnc(Nc3cccc(-c4cncnc4)c3)n2)c(C)n2c1C(=O)NCC2] | *** | B |
| I-54 | 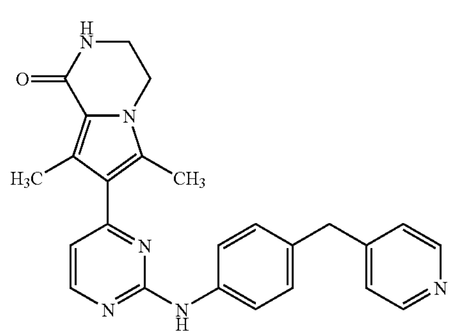 [SMILES: Cc1c(-c2ccnc(Nc3ccc(Cc4ccncc4)cc3)n2)c(C)n2c1C(=O)NCC2] | ** | B |

TABLE 3-continued
Structures and biological activity of compounds in accordance with the invention;
| No. | Structure | Activity | Method |
|---|---|---|---|
| I-55 | 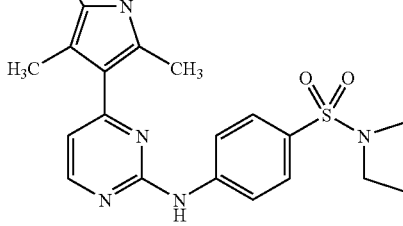 | ** | B |
| I-56 | 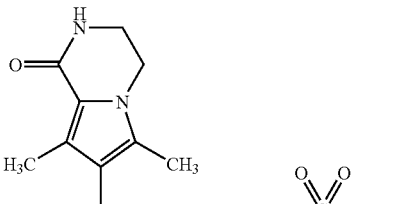 | *** | B |
| I-57 | 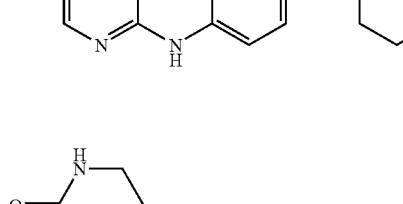 | * | B |
| I-58 | 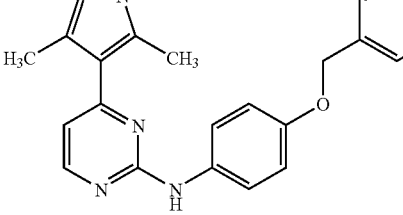 | ** | B |

TABLE 3-continued
Structures and biological activity of compounds in accordance with the invention;
| No. | Structure | Activity | Method |
|---|---|---|---|
| I-59 | 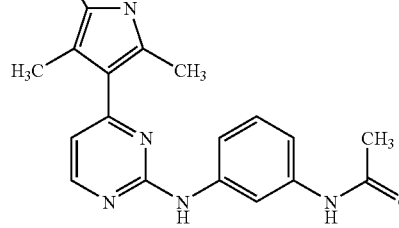 | *** | B |
| I-60 | 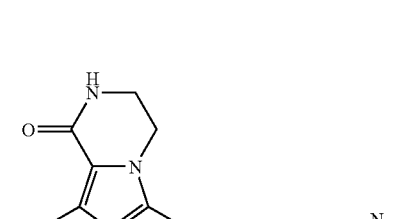 | *** | B |
| I-61 | 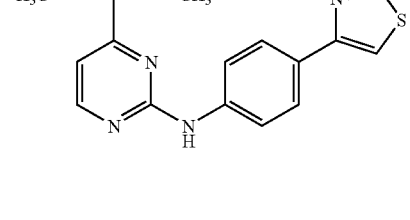 | ** | B |
| I-62 | 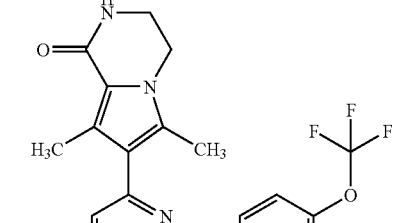 | *** | B |

TABLE 3-continued

Structures and biological activity of compounds in accordance with the invention;

| No. | Structure | Activity | Method |
|---|---|---|---|
| I-63 | 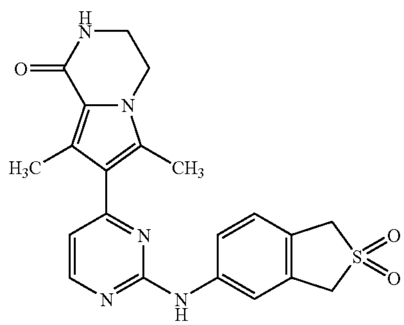 [SMILES: Cc1c(-c2ccnc(Nc3ccc4c(c3)CS(=O)(=O)C4)n2)c(C)n2c1C(=O)NCC2] | *** | B |
| I-64 | 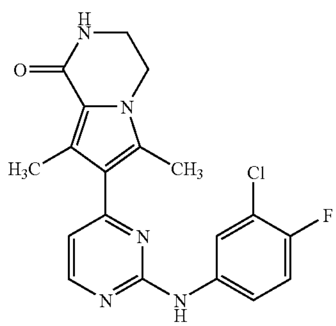 [SMILES: Cc1c(-c2ccnc(Nc3ccc(F)c(Cl)c3)n2)c(C)n2c1C(=O)NCC2] | ** | B |
| I-65 | 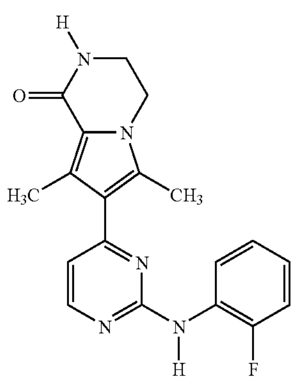 [SMILES: Cc1c(-c2ccnc(Nc3ccccc3F)n2)c(C)n2c1C(=O)NCC2] | ** | B |
| I-66 | 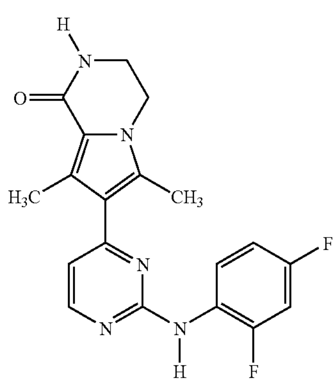 [SMILES: Cc1c(-c2ccnc(Nc3ccc(F)cc3F)n2)c(C)n2c1C(=O)NCC2] | * | B |

TABLE 3-continued

Structures and biological activity of compounds in accordance with the invention;

| No. | Structure | Activity | Method |
|---|---|---|---|
| I-67 | 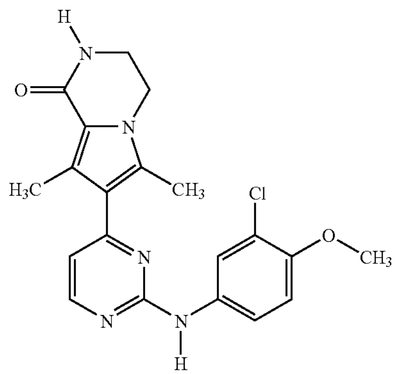 [SMILES: COc1ccc(Nc2nccc(-c3c(C)c4n(c3C)CCNC4=O)n2)cc1Cl] | *** | B |
| I-68 | 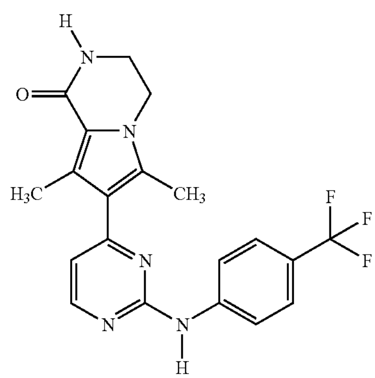 [SMILES: Cc1c(-c2ccnc(Nc3ccc(C(F)(F)F)cc3)n2)c(C)n2c1C(=O)NCC2] | * | B |
| I-69 | 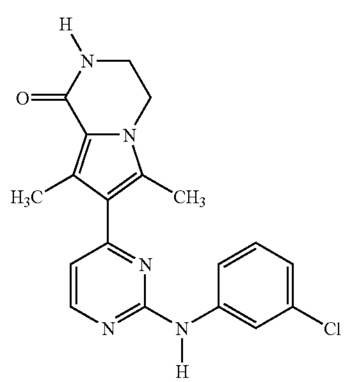 [SMILES: Cc1c(-c2ccnc(Nc3cccc(Cl)c3)n2)c(C)n2c1C(=O)NCC2] | ** | B |
| I-70 | 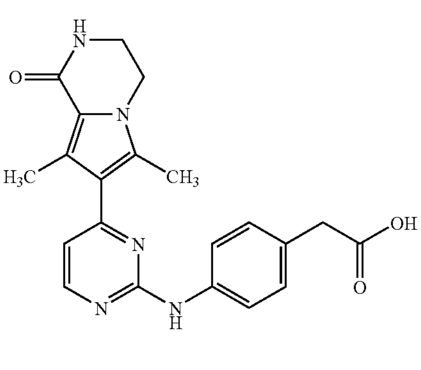 [SMILES: Cc1c(-c2ccnc(Nc3ccc(CC(=O)O)cc3)n2)c(C)n2c1C(=O)NCC2] | *** | B |

TABLE 3-continued

Structures and biological activity of compounds in accordance with the invention;

| No. | Structure | Activity | Method |
|---|---|---|---|
| I-71 | 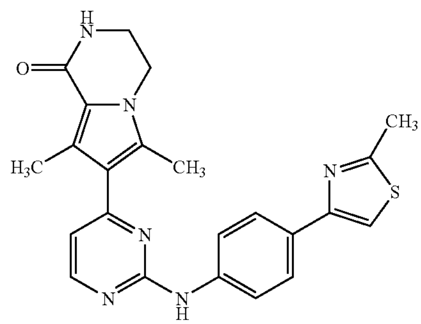 [SMILES: Cc1nc(-c2ccc(Nc3nccc(-c4c(C)c5n(c4C)CCNC5=O)n3)cc2)cs1] | ** | B |
| I-72 | 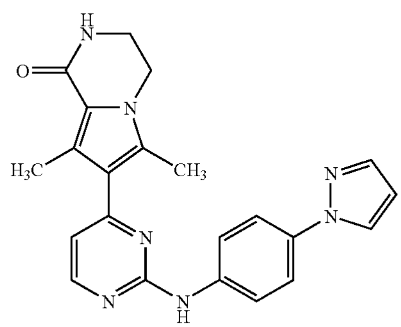 [SMILES: Cc1c(-c2ccnc(Nc3ccc(-n4cccn4)cc3)n2)c(C)n2c1C(=O)NCC2] | ** | B |
| I-73 | 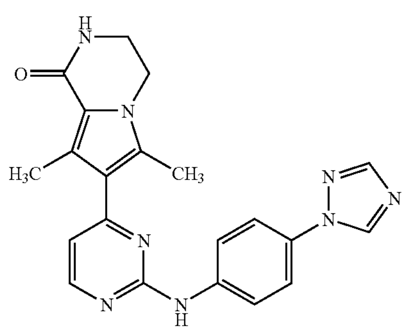 [SMILES: Cc1c(-c2ccnc(Nc3ccc(-n4cncn4)cc3)n2)c(C)n2c1C(=O)NCC2] | ** | B |
| I-74 | 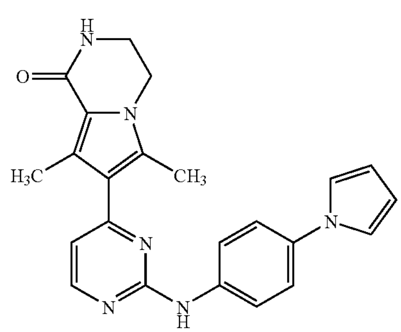 [SMILES: Cc1c(-c2ccnc(Nc3ccc(-n4cccc4)cc3)n2)c(C)n2c1C(=O)NCC2] | ** | B |

TABLE 3-continued

Structures and biological activity of compounds in accordance with the invention;

| No. | Structure | Activity | Method |
|---|---|---|---|
| I-75 | 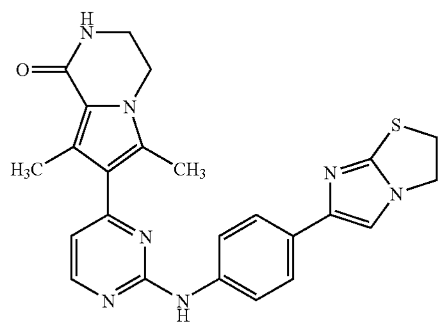 [SMILES: Cc1c(-c2ccnc(Nc3ccc(-c4cn5c(n4)SCC5)cc3)n2)c(C)n2c1C(=O)NCC2] | *** | B |
| I-76 | 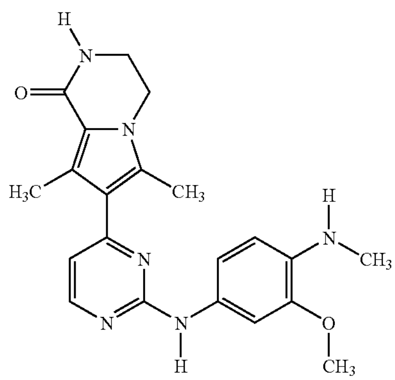 [SMILES: CNc1ccc(Nc2nccc(-c3c(C)c4n(c3C)CCNC4=O)n2)cc1OC] | ** | B |
| I-77 | 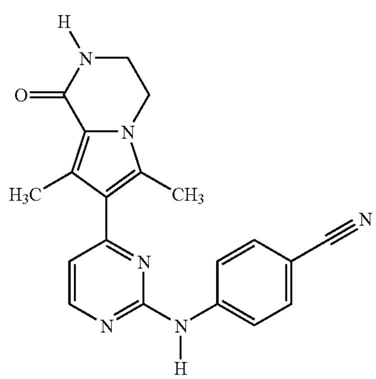 [SMILES: Cc1c(-c2ccnc(Nc3ccc(C#N)cc3)n2)c(C)n2c1C(=O)NCC2] | ** | B |
| I-78 | 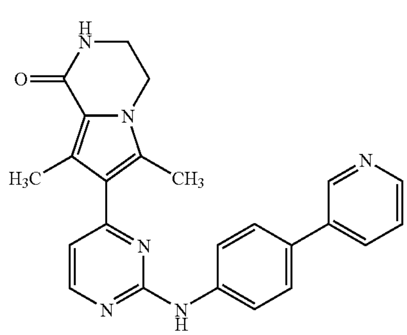 [SMILES: Cc1c(-c2ccnc(Nc3ccc(-c4cccnc4)cc3)n2)c(C)n2c1C(=O)NCC2] | ** | B |

TABLE 3-continued
Structures and biological activity of compounds in accordance with the invention;
| No. | Structure | Activity | Method |
|---|---|---|---|
| I-79 | 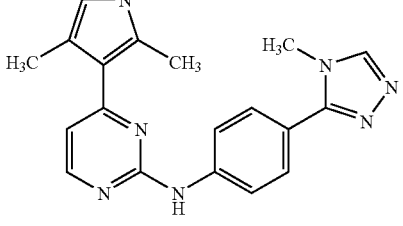 | ** | B |
| I-80 | 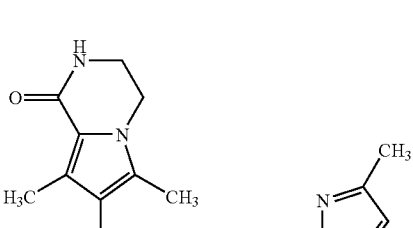 | ** | B |
| I-81 | 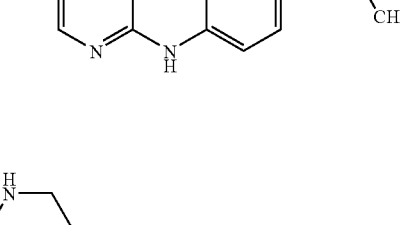 | ** | B |
| I-82 | 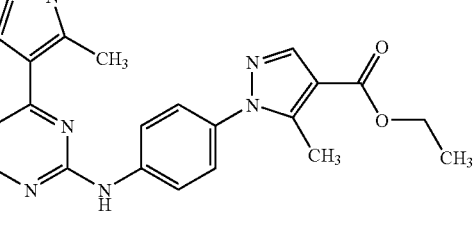 | *** | B |

TABLE 3-continued

Structures and biological activity of compounds in accordance with the invention;

| No. | Structure | Activity | Method |
|---|---|---|---|
| I-83 | 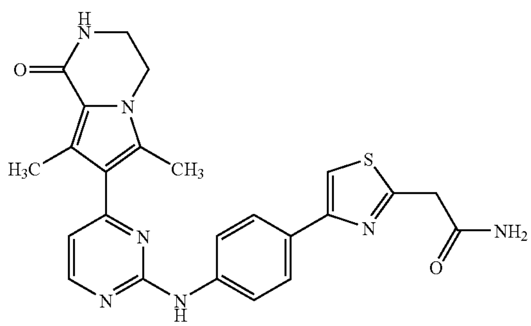 [SMILES: Cc1c(-c2ccnc(Nc3ccc(-c4csc(CC(N)=O)n4)cc3)n2)c(C)n2c1C(=O)NCC2] | ** | B |
| I-84 | 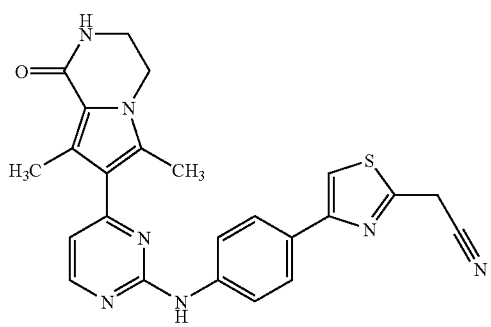 [SMILES: Cc1c(-c2ccnc(Nc3ccc(-c4csc(CC#N)n4)cc3)n2)c(C)n2c1C(=O)NCC2] | ** | B |
| I-85 | 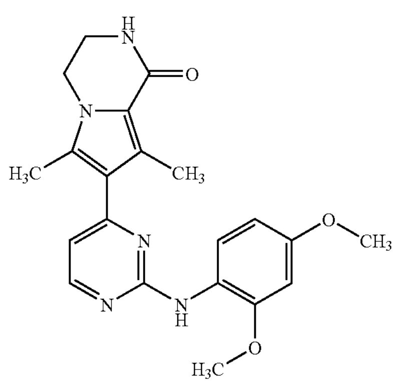 | * | B |
| I-86 | 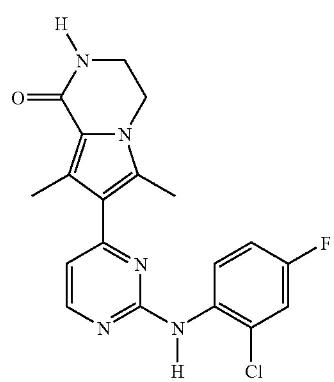 [SMILES: Cc1c(-c2ccnc(Nc3ccc(F)cc3Cl)n2)c(C)n2c1C(=O)NCC2] | * | B |

TABLE 3-continued

Structures and biological activity of compounds in accordance with the invention;

| No. | Structure | Activity | Method |
|---|---|---|---|
| I-87 | 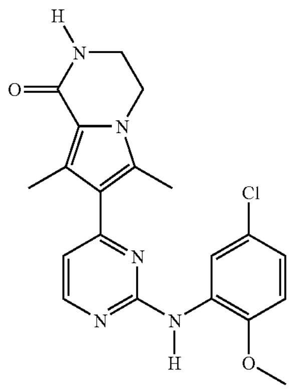 [SMILES: COc1ccc(Cl)cc1Nc1nccc(-c2c(C)c3n(c2C)CCNC3=O)n1] | * | B |
| I-88 | 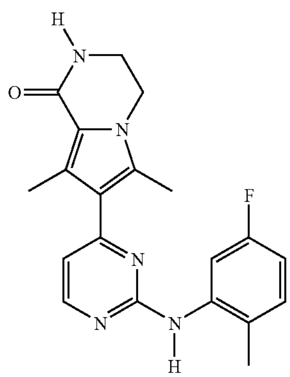 [SMILES: Cc1ccc(F)cc1Nc1nccc(-c2c(C)c3n(c2C)CCNC3=O)n1] | * | B |
| I-89 | 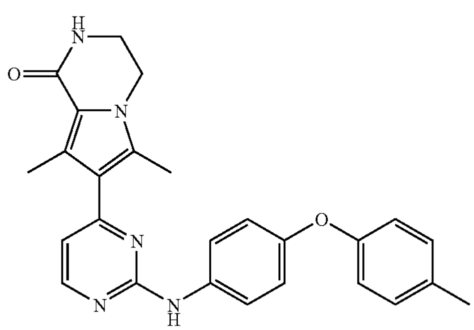 [SMILES: Cc1ccc(Oc2ccc(Nc3nccc(-c4c(C)c5n(c4C)CCNC5=O)n3)cc2)cc1] | * | B |
| I-90 | 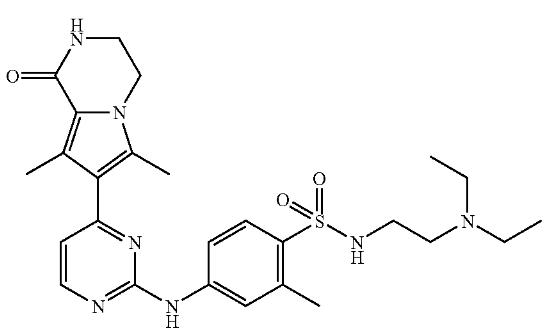 [SMILES: CCN(CC)CCNS(=O)(=O)c1ccc(Nc2nccc(-c3c(C)c4n(c3C)CCNC4=O)n2)cc1C] | * | B |

TABLE 3-continued

Structures and biological activity of compounds in accordance with the invention;

| No. | Structure | Activity | Method |
|---|---|---|---|
| I-91 | 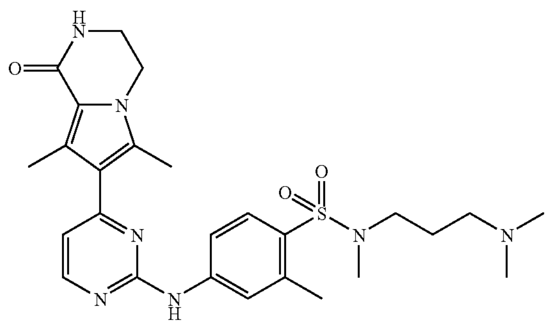 [SMILES: Cc1cc(Nc2nccc(-c3c(C)c4n(c3C)CCNC4=O)n2)ccc1S(=O)(=O)N(C)CCCN(C)C] | * | B |
| I-92 | 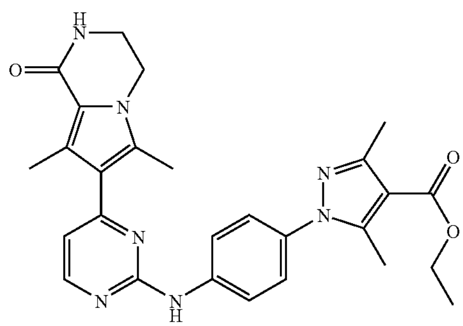 [SMILES: CCOC(=O)c1c(C)nn(-c2ccc(Nc3nccc(-c4c(C)c5n(c4C)CCNC5=O)n3)cc2)c1C] | * | B |
| I-93 | 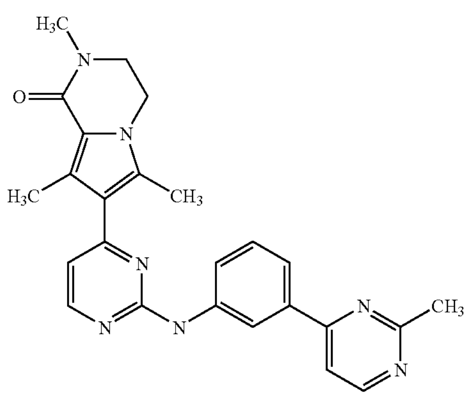 [SMILES: Cc1nccc(-c2cccc(Nc3nccc(-c4c(C)c5n(c4C)CCN(C)C5=O)n3)c2)n1] | *** | B |
| I-94 | 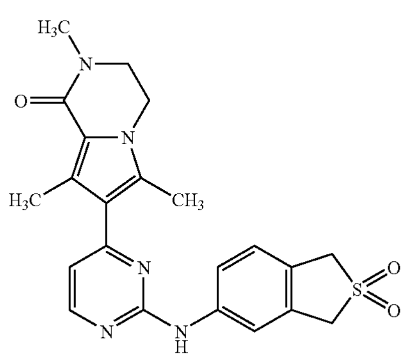 [SMILES: Cc1c(-c2ccnc(Nc3ccc4c(c3)CS(=O)(=O)C4)n2)c(C)n2c1C(=O)N(C)CC2] | *** | B |

TABLE 3-continued

Structures and biological activity of compounds in accordance with the invention;

| No. | Structure | Activity | Method |
|---|---|---|---|
| I-95 | 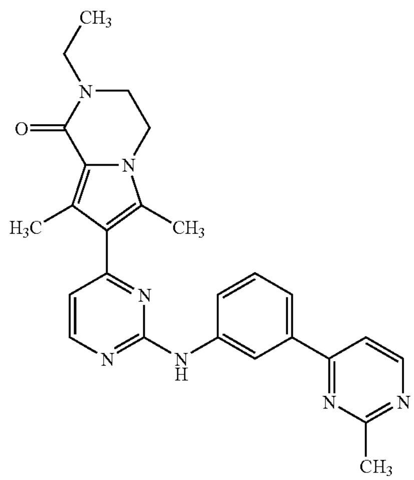 [SMILES: CCN1CCn2c(C)c(-c3ccnc(Nc4cccc(-c5ccnc(C)n5)c4)n3)c(C)c2C1=O] | ** | B |
| I-95a | 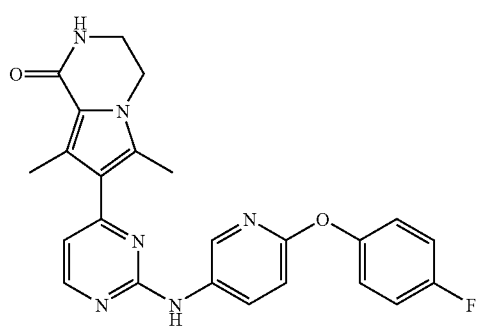 [SMILES: Cc1c(-c2ccnc(Nc3ccc(Oc4ccc(F)cc4)nc3)n2)c(C)n2c1C(=O)NCC2] | | B |
| I-95b | 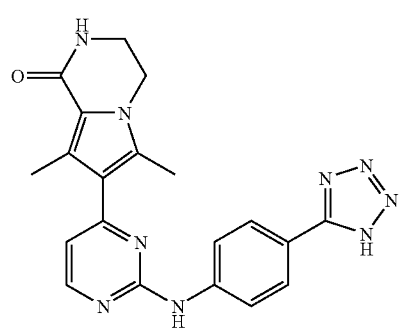 [SMILES: Cc1c(-c2ccnc(Nc3ccc(-c4nnn[nH]4)cc3)n2)c(C)n2c1C(=O)NCC2] | | B |
| I-95c | 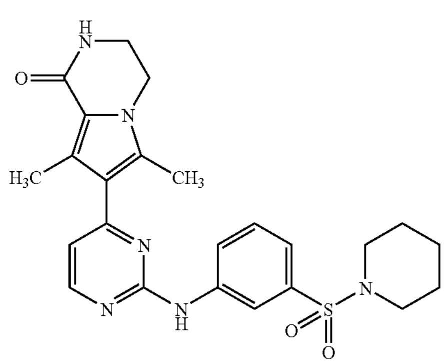 [SMILES: Cc1c(-c2ccnc(Nc3cccc(S(=O)(=O)N4CCCCC4)c3)n2)c(C)n2c1C(=O)NCC2] | * | B |

TABLE 3-continued

Structures and biological activity of compounds in accordance with the invention;

| No. | Structure | Activity | Method |
|---|---|---|---|
| I-96 | 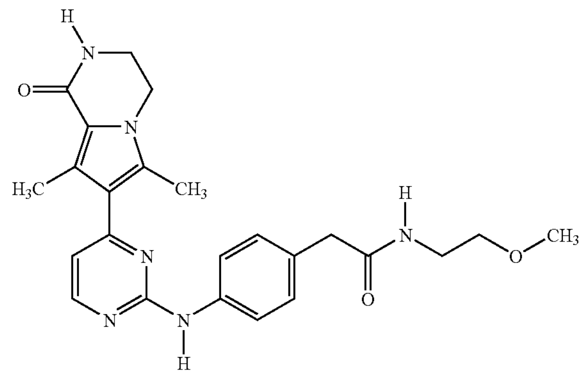 [SMILES: COCCNC(=O)Cc1ccc(Nc2nccc(-c3c(C)c4n(c3C)CCNC4=O)n2)cc1] | *** | S1 |
| I-97 | 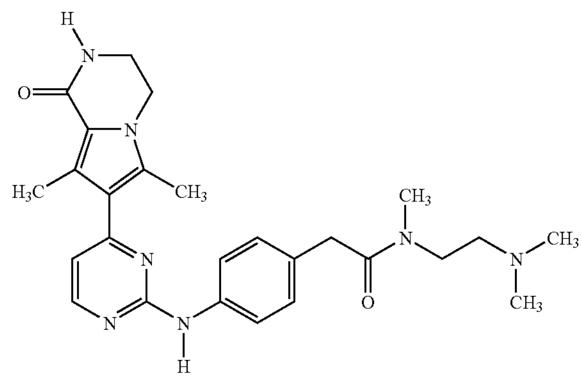 [SMILES: Cc1c(-c2ccnc(Nc3ccc(CC(=O)N(C)CCN(C)C)cc3)n2)c(C)n2c1C(=O)NCC2] | ** | S1 |
| I-98 | 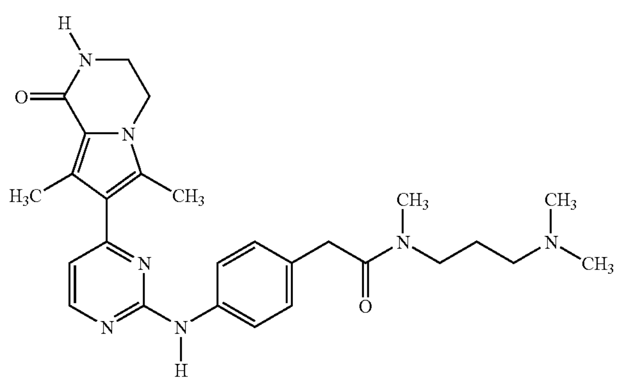 [SMILES: Cc1c(-c2ccnc(Nc3ccc(CC(=O)N(C)CCCN(C)C)cc3)n2)c(C)n2c1C(=O)NCC2] | ** | S1 |
| I-99 | 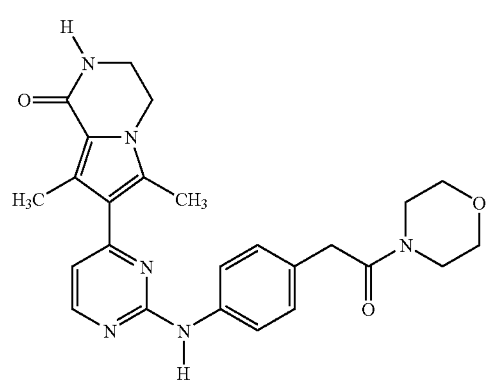 [SMILES: Cc1c(-c2ccnc(Nc3ccc(CC(=O)N4CCOCC4)cc3)n2)c(C)n2c1C(=O)NCC2] | ** | S1 |

TABLE 3-continued

Structures and biological activity of compounds in accordance with the invention;

| No. | Structure | Activity | Method |
|---|---|---|---|
| I-100 | 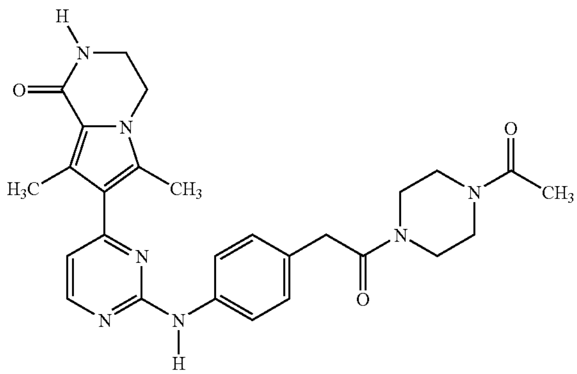 [SMILES: CC(=O)N1CCN(C(=O)Cc2ccc(Nc3nccc(-c4c(C)c5n(c4C)CCNC5=O)n3)cc2)CC1] | ** | S1 |
| I-101 | 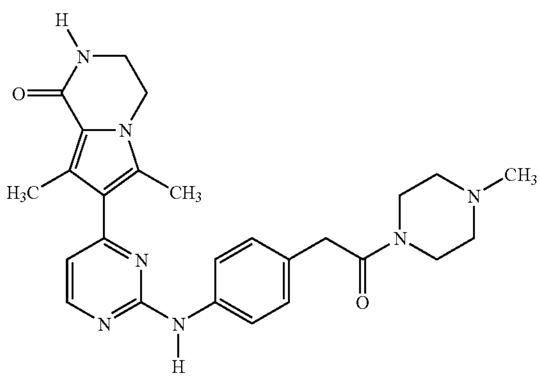 [SMILES: Cc1c(-c2ccnc(Nc3ccc(CC(=O)N4CCN(C)CC4)cc3)n2)c(C)n2c1C(=O)NCC2] | *** | S1 |
| I-102 | 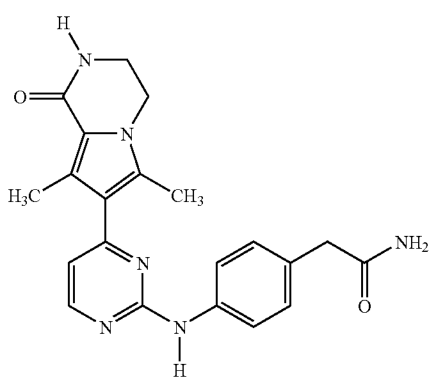 [SMILES: Cc1c(-c2ccnc(Nc3ccc(CC(N)=O)cc3)n2)c(C)n2c1C(=O)NCC2] | *** | S1 |
| I-103 | 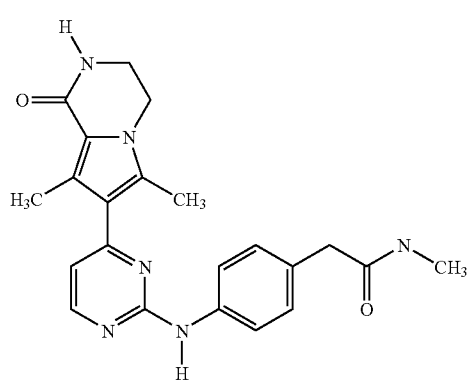 [SMILES: CNC(=O)Cc1ccc(Nc2nccc(-c3c(C)c4n(c3C)CCNC4=O)n2)cc1] | *** | S1 |

TABLE 3-continued

Structures and biological activity of compounds in accordance with the invention;

| No. | Structure | Activity | Method |
|---|---|---|---|
| I-104 | 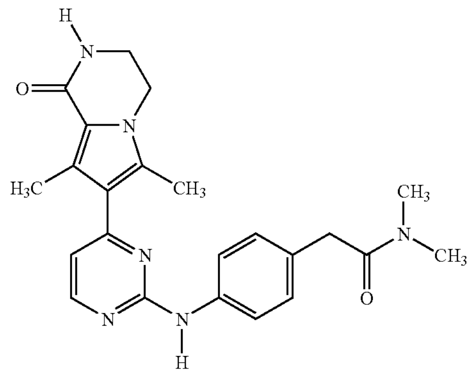 [SMILES: Cc1c(-c2ccnc(Nc3ccc(CC(=O)N(C)C)cc3)n2)c(C)n2c1C(=O)NCC2] | ** | S1 |
| I-105 | 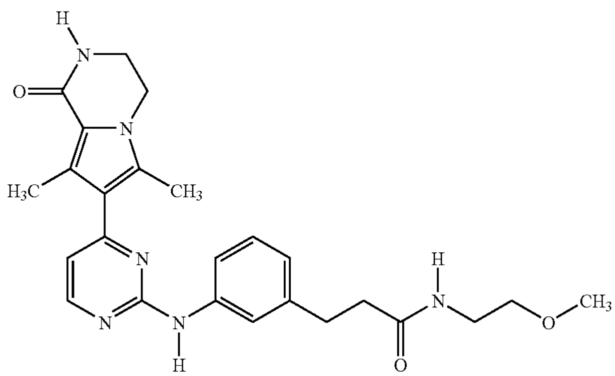 [SMILES: COCCNC(=O)CCc1cccc(Nc2nccc(-c3c(C)c4n(c3C)CCNC4=O)n2)c1] | *** | S1 |
| I-106 | 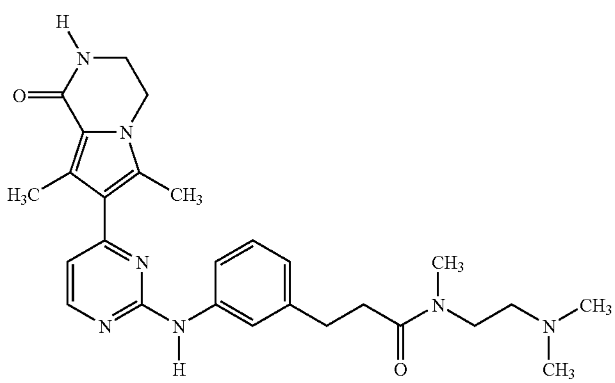 [SMILES: Cc1c(-c2ccnc(Nc3cccc(CCC(=O)N(C)CCN(C)C)c3)n2)c(C)n2c1C(=O)NCC2] | ** | S1 |
| I-107 | 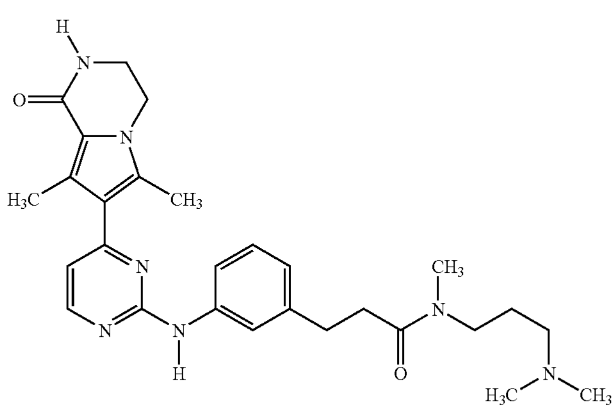 [SMILES: Cc1c(-c2ccnc(Nc3cccc(CCC(=O)N(C)CCCN(C)C)c3)n2)c(C)n2c1C(=O)NCC2] | ** | S1 |

TABLE 3-continued

Structures and biological activity of compounds in accordance with the invention;

| No. | Structure | Activity | Method |
|---|---|---|---|
| I-108 | 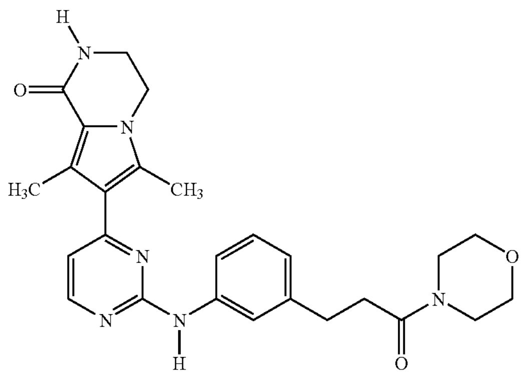 [SMILES: Cc1c(-c2ccnc(Nc3cccc(CCC(=O)N4CCOCC4)c3)n2)c(C)n2c1C(=O)NCC2] | *** | S1 |
| I-109 | 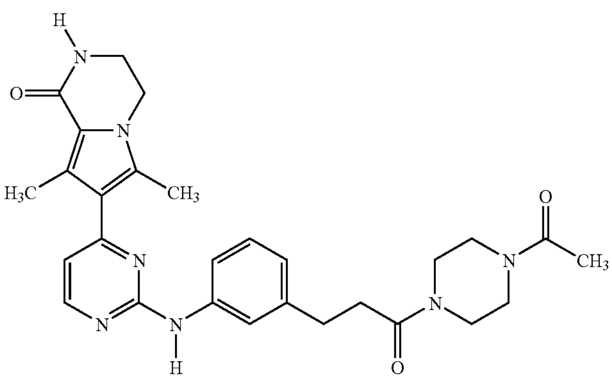 [SMILES: CC(=O)N1CCN(C(=O)CCc2cccc(Nc3nccc(-c4c(C)c5n(c4C)CCNC5=O)n3)c2)CC1] | ** | S1 |
| I-110 | 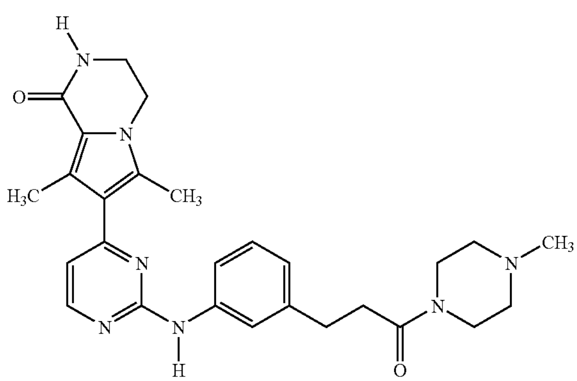 [SMILES: Cc1c(-c2ccnc(Nc3cccc(CCC(=O)N4CCN(C)CC4)c3)n2)c(C)n2c1C(=O)NCC2] | ** | S1 |
| I-111 | 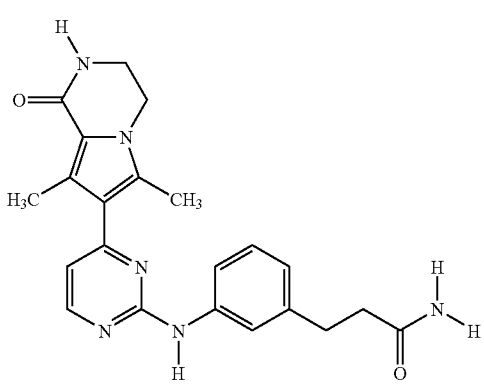 [SMILES: Cc1c(-c2ccnc(Nc3cccc(CCC(N)=O)c3)n2)c(C)n2c1C(=O)NCC2] | *** | S1 |

TABLE 3-continued

Structures and biological activity of compounds in accordance with the invention;

| No. | Structure | Activity | Method |
|---|---|---|---|
| I-112 | 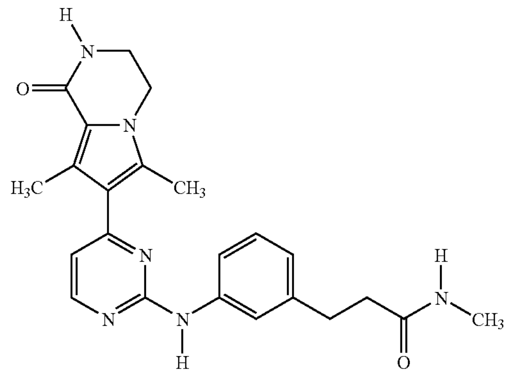 [SMILES: CNC(=O)CCc1cccc(Nc2nccc(-c3c(C)c4n(c3C)CCNC4=O)n2)c1] | *** | S1 |
| I-113 | 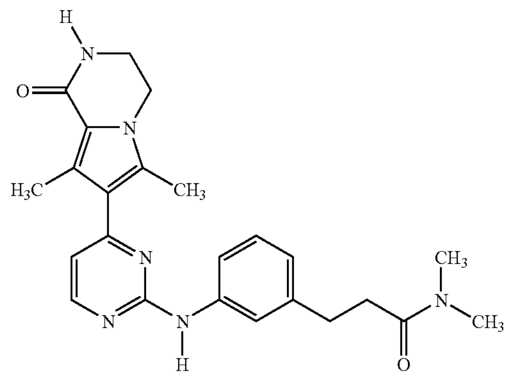 [SMILES: Cc1c(-c2ccnc(Nc3cccc(CCC(=O)N(C)C)c3)n2)c(C)n2c1C(=O)NCC2] | *** | S1 |
| I-114 | 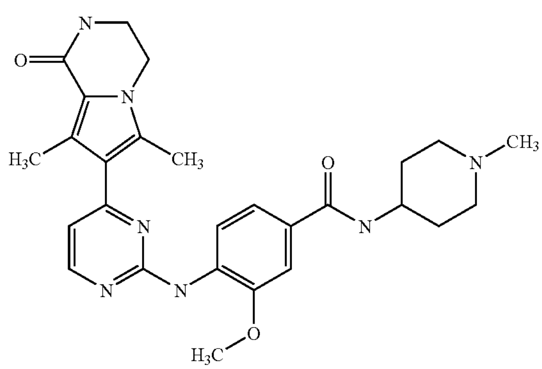 [SMILES: COc1cc(C(=O)NC2CCN(C)CC2)ccc1Nc1nccc(-c2c(C)c3n(c2C)CCNC3=O)n1] | * | S2 |
| I-115 | 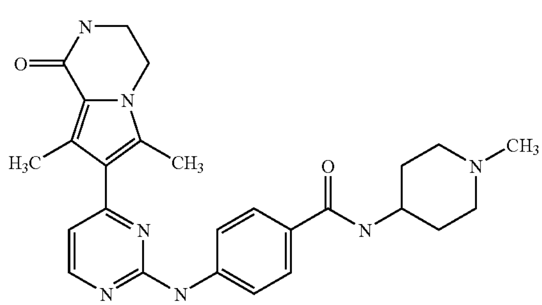 [SMILES: Cc1c(-c2ccnc(Nc3ccc(C(=O)NC4CCN(C)CC4)cc3)n2)c(C)n2c1C(=O)NCC2] | *** | S2 |

Aurora A activity is denoted by a grading system:
*** means less than 0.1 µM $IC_{50}$
** means less than 1.0 µM $IC_{50}$
* means less than 10 µM $IC_{50}$

The invention claimed is:
1. A compound of formula I, or a pharmaceutically acceptable salt thereof,

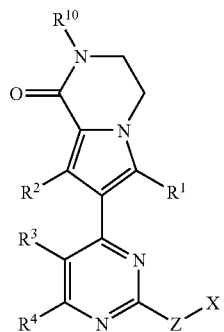

I wherein
Z is $NR^{11}$, NHCO, $NHSO_2$, $NHCH_2$, $CH_2$, $CH_2CH_2$, or CH=CH;
X is a hydrocarbyl group optionally substituted by one or more $R^{12}$ groups;
$R^{10}$ and $R^{11}$ are each independently H or alkyl;
$R^1$-$R^4$ are each independently H or $(CH_2)_m R^{12}$, where m is 0, 1, 2, or 3;
each $R^{12}$ is independently $(CH_2)_a R^{16}$, where each $R^{16}$ is independently selected from $O(CH_2)_b R^{13}$, $R^{13}$, $COR^{13}$, $COOR^{13}$, CN, $CONR^{13}R^{14}$, $NR^{13}R^{14}$, $NR^{13}COR^{14}$, $SR^{13}$, $SOR^{13}$, $SO_2R^{13}$, $NR^{13}SO_2R^{14}$, $SO_2OR^{13}$, $SO_2NR^{13}R^{14}$, halogen, $CF_3$, and $NO_2$, and wherein each a is 0, 1, 2, or 3 and b is 0, 1, 2, or 3;
$R^{13}$ and $R^{14}$ are each independently H or $(CH_2)_n R^{15}$, where n is 0, 1, 2, or 3; and
each $R^{15}$ is independently selected from alkyl, cycloalkyl, heteroaryl, aralkyl, aryl and heterocycloalkyl, each of which may be optionally substituted by one or more substituents selected from halogen, OH, CN, COO-alkyl, aralkyl, $SO_2$-alkyl, $SO_2$-aryl, COOH, CO-alkyl, CO-aryl, $NH_2$, NH-alkyl, N(alkyl)$_2$, $CF_3$, alkyl and alkoxy, wherein said alkyl and alkoxy groups may be further substituted by one or more OH groups.

2. A compound according to claim 1 wherein X is:
(i) a $C_{5-15}$ saturated or unsaturated monocyclic group, or
(ii) a bicyclic or tricyclic group, each of which may be saturated or unsaturated, or a combination thereof, and fused or unfused;
wherein each group optionally contains one or more heteroatoms selected from O, N and S and/or one or more $SO_2$ and/or C=O groups, and is optionally substituted by one or more $R^{12}$ groups.

3. A compound according to claim 1 wherein X optionally contains one, two or three heteroatoms selected from O, N and S and/or optionally contains one C=O group and/or one $SO_2$ group.

4. A compound according to claim 1 wherein X is a monocyclic group selected from phenyl, 2-pyridynyl, 3-pyridynyl and 4-pyridynyl, each of which may be optionally substituted by one or more $R^{12}$ substituents.

5. A compound according to claim 1 wherein X is selected from thiomorpholinyl-phenyl, morpholino-phenyl, piperazinyl-phenyl, pyrimidinyl-phenyl, isoxazolyl-phenyl, oxazolyl-phenyl, pyrrolyl-phenyl, triazolyl-phenyl, thiazolyl-phenyl, 2,3-dihydro-imidazothiazolyl-phenyl, 2-oxo-oxazolidinyl-phenyl, [1,2,3]-thiadiazol-4-yl-phenyl and pyrazolyl-phenyl, each of which may be optionally substituted by one or more $R^{12}$ groups.

6. A compound according to claim 1 wherein X is group selected from 4-(2-oxo-oxazolidin-3-yl)-phenyl, 4-pyrazol-1-yl-phenyl, 4-[1,2,3]thiadiazol-4-yl-phenyl, 4-thiomorpholin-4-yl-phenyl, 4-[1,2,4]-triazol-1-yl-phenyl, thiazol-4-yl-phenyl, 4H-[1,2,4]-triazol-3-yl-phenyl, 2,3-dihydro-imidazo[2,1-b]thiazol-6-yl-phenyl, 4-morpholin-4-yl-phenyl, 4-oxazol-5-yl-phenyl, 4-isoxazol-5-yl-phenyl, 4-pyrrol-1-yl-phenyl, 3-oxazol-5-yl-phenyl, 4-piperazin-1-yl-phenyl, pyrimidin-4-yl-phenyl and pyrimidin-5-yl-phenyl, each of which may be optionally substituted by one or more $R^{12}$ groups.

7. A compound according to claim 1 wherein X is group selected from the following:

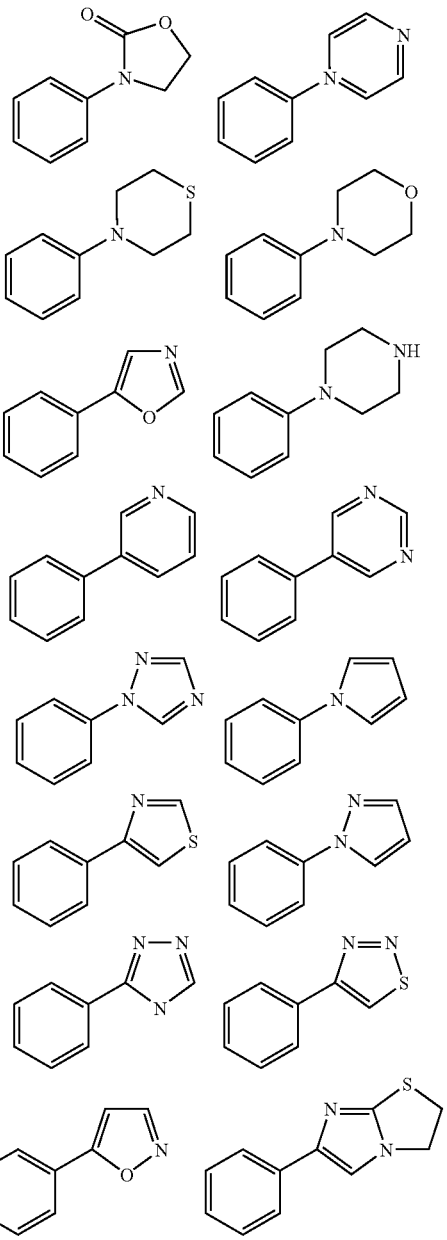

each of which may be optionally substituted by one or more $R^{12}$ groups.

8. A compound according to claim 1 wherein X is a fused bicyclic group selected from indazolyl, benzo-oxazinonyl, benzothiophenyl, benzodioxolyl, benzodioxinyl, indolyl, 3,4-dihydro-2H-benzodioxepinyl and 2,2-dioxo-2,3-dihydro-1H-2-benzothiophenyl, each of which may be optionally substituted by one or more $R^{12}$ groups.

9. A compound according to claim 1 wherein X is a fused bicyclic group selected from 1H-indazol-6-yl, 2,2-dioxo-2,3-dihydro-1H-2-benzo[c]thiophen-5-ylamino, 3,4-dihydro-2H-benzo[b][1,4]dioxepin-7-yl, 1H-indol-5-yl, 4H-benzo[1,3]dioxin-6-yl, benzo-[1,3]dioxol-5-yl, 5-benzo[b]thiophenyl and 4H-benzo[1,4]oxazin-3-onyl, each of which may be optionally substituted by one or more $R^{12}$ groups.

10. A compound according to claim 1 wherein X is a fused bicyclic group selected from the following:

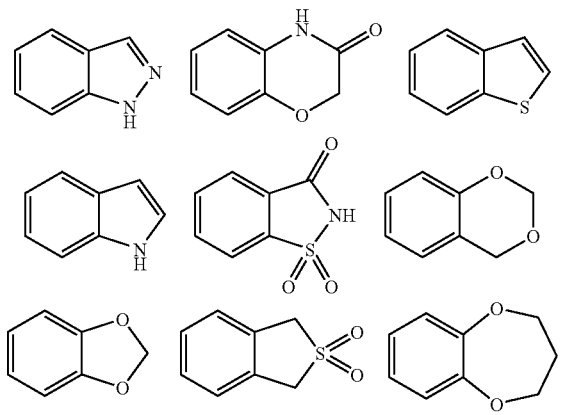

each of which may be optionally substituted by one or more $R^{12}$ groups.

11. A compound according to claim 1 wherein X is optionally substituted by one or two $R^{12}$ groups.

12. A compound according to claim 1 wherein each $R^{12}$ is independently selected from $O(CH_2)_b R^{13}$, $R^{13}$, $(CH_2)_a COR^{13}$, $(CH_2)_a COOR^{13}$, $COOR^{13}$, CN, $(CH_2)_a CONR^{13}R^{14}$, $NR^{13}R^{14}$, $NR^{13}COR^{14}$, $SR^{13}$, $SOR^{13}$, $SO_2R^{13}$, $NR^{13}SO_2R^{14}$, $SO_2OR^{13}$, $SO_2NR^{13}R^{14}$, halogen, $CF_3$, and $NO_2$.

13. A compound according to claim 1 wherein each $R^{12}$ is independently selected from O-alkyl, alkyl, halogen, $(CH_2)_a$—COOH, $NHSO_2$-alkyl, $NO_2$, CN, NHCO-alkyl, NHCO-aryl, CO-alkyl, CO-aryl, COO-alkyl, $N(alkyl)_2$, NH-alkyl, $SO_2$-alkyl, OH, $SO_2$-heterocycloalkyl, $SO_2$—NH-alkyl, $SO_2$—N$(alkyl)_2$, $(CH_2)_a$—CO-heterocycloalkyl, $(CH_2)_a$—CONH-alkyl, $(CH_2)_a CONH_2$, $(CH_2)_a CON(alkyl)_2$, $O(CH_2)_b$-aryl, $(CH_2)_a$-heteroaryl and $O(CH_2)_b$-heterocycloalkyl, wherein said alkyl, aryl, heteroaryl and heterocycloalkyl groups may be further substituted by one or more substituents selected from CN, halogen, alkyl and CO-alkyl.

14. A compound according to claim 1 wherein each $R^{12}$ is independently selected from OMe, Me, Cl, Br, F, $CH_2COOH$, $CH_2CH_2COOH$, $OCH_2COOH$, $CH(Me)COOH$, COOH, $NHSO_2Me$, $NO_2$, CN, $CH_2CN$, $OCH_2Ph$, NHCOMe, NHCO-aryl, COMe, COPh, COOEt, $NMe_2$, $NEt_2$, NHMe, $SO_2Me$, $SO_2Pr$, OH, $SO_2$—NH—$(CH_2)_3NEt_2$, $SO_2$—NH—$(CH_2)_2NEt_2$, $SO_2$—NH—$(CH_2)_2NMe_2$, $SO_2$—N(Me)-$(CH_2)_3NMe_2$, $SO_2$—NH—$(CH_2)_2OMe$, $SO_2$-pyrrolidine, $SO_2$-piperidine, $CF_3$, $SO_2$—NHPr, $SO_2$-morpholine, $SO_2$—NHMe, $(CH_2)_2$—CO-morpholine, $CH_2CO$-morpholine, $CH_2CONHMe$, $CH_2CONH(CH_2)_2OMe$, $CH_2CONH(CH_2)_2OMe$, $CH_2CONH(CH_2)_2NMe_2$, $CH_2CONH(CH_2)_3NMe_2$, $CH_2CH_2CON(Me)(CH_2)_3NMe_2$, $CH_2CH_2CON(Me)(CH_2)_2NMe_2$, $CH_2CONH_2$, $CH_2CON(Me)_2$, $CH_2CH_2CON(Me)_2$, $CH_2CH_2CONHMe$, $CH_2CH_2CONH_2$, $CH_2$-(4-pyridine), $O(CH_2)_2$-morpholine, O-(4-methylphenyl), CO-(4-methylpiperazine), $CH_2CO$-(4-methylpiperazine), $CH_2CH_2CO$-(4-methylpiperazine), $SO_2$-(4-methylpiperazine), $CH_2CO$-(4-acetylpiperazine) and $CH_2CH_2CO$-(4-acetylpiperazine).

15. A compound according to claim 1 wherein X is a phenyl or 3-pyridinyl group, each of which may be optionally substituted by one or more $R^{12}$ groups.

16. A compound according to claim 1, of formula Ia, or a pharmaceutically acceptable salt thereof,

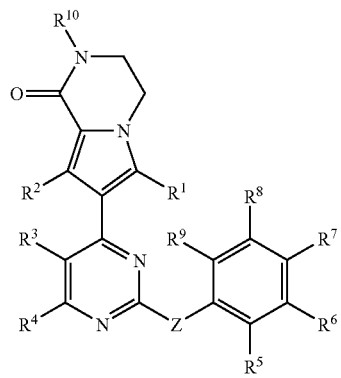

Ia wherein

Z is $NR^{11}$, NHCO, $NHSO_2$, $NHCH_2$, $CH_2$, $CH_2CH_2$, or CH=CH;

$R^{10}$ and $R^{11}$ are each independently H or alkyl;

$R^1$-$R^9$ are each independently H or $(CH_2)_m R^{12}$, where m is 0, 1, 2, or 3;

each $R^{12}$ is independently $(CH_2)_a R^{16}$, where each $R^{16}$ is independently selected from $O(CH_2)_b R^{13}$, $R^{13}$, $COR^{13}$, $COOR^{13}$, CN, $CONR^{13}R^{14}$, $NR^{13}R^{14}$, $NR^{13}COR^{14}$, $SR^{13}$, $SOR^{13}$, $SO_2R^{13}$, $NR^{13}SO_2R^{14}$, $SO_2OR^{13}$, $SO_2NR^{13}R^{14}$, halogen, $CF_3$, and $NO_2$, and wherein each a is 0, 1, 2, or 3 and b is 0, 1, 2, or 3;

$R^{13}$ and $R^{14}$ are each independently H or $(CH_2)_n R^{15}$, where n is 0, 1, 2, or 3; and each $R^{15}$ is independently selected from alkyl, cycloalkyl, heteroaryl, aralkyl, aryl and heterocycloalkyl, each of which may be optionally substituted by one or more substituents selected from halogen, OH, CN, COO-alkyl, aralkyl, $SO_2$-alkyl, $SO_2$-aryl, COOH, CO-alkyl, CO-aryl, $NH_2$, NH-alkyl, $N(alkyl)_2$, $CF_3$, alkyl and alkoxy, wherein said alkyl and alkoxy groups may be further substituted by one or more OH groups.

17. A compound according to claim 1 wherein Z is $NR^{11}$.

18. A compound according to claim 1 wherein Z is NH.

19. A compound according to claim 1 wherein $R^3$ and $R^4$ are both H.

20. A compound according to claim 1 wherein each $R^{15}$ is independently selected from ethyl, ethyl, isopropyl, n-butyl, isobutyl, t-butyl, cyclopropyl, cyclobutyl, cyclopentyl, cyclohexyl, phenyl, pyridinyl, pyrrolidinyl, pyrrolyl, morpholinyl, piperazinyl, piperidinyl, triazolyl, tetrazolyl and thiazolyl.

21. A compound according to claim 1 wherein each $R^{12}$ is independently selected from OH, OMe, COMe, CHO, $CO_2Me$, COOH, CN, $CONH_2$, NHMe, $NH_2$, $NMe_2$, SH, SMe, SOMe, SO$_2$Me, SO$_2$NHMe, SO$_2$NH$_2$, Cl, Br, F, I, CF$_3$, NO$_2$, N-morpholinyl, N-pyrrolidinyl and N-piperazinyl.

22. A compound according to claim 1 wherein:
R$^5$, R$^6$, R$^7$, R$^8$ and R$^9$ are each independently selected from H and (CH$_2$)$_m$R$^{12}$;
each R$^{12}$ is independently selected from R$^{13}$, NR$^{13}$COR$^{14}$, NR$^{13}$R$^{14}$, SO$_2$R$^{13}$, NR$^{13}$SO$_2$R$^{14}$, OR$^{13}$, alkyl, NO$_2$, CF$_3$, alkoxy, halogen;
R$^{13}$ and R$^{14}$ are each independently H or (CH$_2$)$_n$R$^{15}$; and
each R$^{15}$ is independently selected from alkyl, heteroaryl, aryl and heterocycloalkyl, each of which may be optionally substituted by one or more substituents selected from halogen, OH, CN, COO-alkyl, COOH, CO-alkyl, aralkyl, SO$_2$-alkyl, SO$_2$-aryl, CO-aryl, alkyl, alkoxy, NH$_2$, NH-alkyl, N(alkyl)$_2$ and CF$_3$.

23. A compound according to claim 1 wherein:
R$^5$, R$^6$, R$^7$, R$^8$ and R$^9$ are each independently selected from H and R$^{12}$;
each R$^{12}$ is independently selected from R$^{13}$, NHCOR$^{14}$, NR$^{13}$R$^{14}$, SO$_2$R$^{13}$, NHSO$_2$R$^{14}$, OR$^{13}$ alkyl, NO$_2$, CF$_3$, alkoxy, halogen;
R$^{13}$ and R$^{14}$ are each independently H or R$^{15}$; and
each R$^{15}$ is independently selected from alkyl, aryl and heterocycloalkyl, each of which may be optionally substituted by one or more substituents selected from halogen, OH, CO-alkyl, aralkyl, SO$_2$-alkyl, SO$_2$-aryl, CO-aryl, alkyl, alkoxy, NH$_2$, NH-alkyl and N(alkyl)$_2$.

24. A compound according to claim 1 wherein R$^5$, R$^6$, R$^7$, R$^8$ and R$^9$ are each independently selected from H, Me, NO$_2$, CF$_3$, OMe, F, N-morpholinyl, N-piperazinyl and N-piperidinyl, said N-morpholinyl, N-piperazinyl and N-piperidinyl groups being optionally substituted by one or more substituents selected from halogen, OH, CN, COO-Me, COOH, CO-Me, CO-phenyl, Me, OMe, NH$_2$, NH-Me, NMe$_2$ and CF$_3$.

25. A compound according to claim 1 wherein:
R$^5$, R$^8$ and R$^9$ are all H; and
R$^6$ and R$^7$ are each independently H or (CH$_2$)$_m$R$^{12}$.

26. A compound according to claim 1 wherein:
R$^5$, R$^8$ and R$^9$ are all H; and
R$^6$ and R$^7$ are each independently H or R$^{12}$.

27. A compound according to claim 1 wherein:
R$^5$, R$^8$ and R$^9$ are all H; and
R$^6$ and R$^7$ are each independently selected from H, alkyl, NO$_2$, CF$_3$, alkoxy, halogen and heterocycloalkyl, said heterocycloalkyl being optionally substituted by one or more substituents selected from halogen, OH, CN, COO-alkyl, COOH, CO-alkyl, CO-aryl, alkyl, alkoxy, NH$_2$, NH-alkyl, N(alkyl)$_2$ and CF$_3$.

28. A compound according to claim 1 wherein:
R$^5$, R$^8$ and R$^9$ are all H; and
R$^6$ and R$^7$ are each independently selected from H, Me, NO$_2$, CF$_3$, OMe, F, N-morpholinyl, N-piperazinyl and N-piperidinyl, said N-morpholinyl, N-piperazinyl and N-piperidinyl groups being optionally substituted by one or more substituents selected from halogen, OH, CN, COO-Me, COOH, CO-Me, CO-phenyl, Me, OMe, NH$_2$, NH-Me, NMe$_2$ and CF$_3$.

29. A compound according to claim 1 wherein R$^1$ and R$^2$ are each independently selected from H, CN, NO$_2$, alkyl, CONR$^{13}$R$^{14}$, NR$^{13}$R$^{14}$, NHCOR$^{13}$OR$^{13}$, R$^{13}$, and NR$^{13}$SO$_2$R$^{14}$.

30. A compound according to claim 1 wherein R$^1$ and R$^2$ are each independently selected from H, CN, NO$_2$, alkyl, NR$^{13}$R$^{14}$, NR$^{13}$COR$^{14}$ and OR$^{13}$, where R$^{13}$ and R$^{14}$ are each independently H or alkyl.

31. A compound according to claim 1 wherein R$^1$ and R$^2$ are each independently alkyl.

32. A compound according to claim 1 wherein R$^1$ and R$^2$ are both methyl.

33. A compound according to claim 1 which is selected from the following:
6,8-Dimethyl-7-[2-(4-morpholin-4-yl-phenylamino)-pyrimidin-4-yl]-3,4-dihydro-2H-pyrrolo[1,2-a]pyrazin-1-one [I-2];
7-[2-(4-Fluoro-phenylamino)-pyrimidin-4-yl]-6,8-dimethyl-3,4-dihydro-2H-pyrrolo[1,2-a]pyrazin-1-one [I-1];
7-[2-(3-Methoxy-4-morpholin-4-yl-phenylamino)-pyrimidin-4-yl]-6,8-dimethyl-3,4-dihydro-2H-pyrrolo[1,2-a]pyrazin-1-one [I.3];
7-[2-(4-Methoxy-phenylamino)-pyrimidin-4-yl]-6,8-dimethyl-3,4-dihydro-2H-pyrrolo[1,2-a]pyrazin-1-one [I.4];
6,8-Dimethyl-7-[2-(3-nitro-phenylamino)-pyrimidin-4-yl]-3,4-dihydro-2H-pyrrolo[1,2-a]pyrazin-1-one [I-5]
7-[2-(4-Dimethylamino-phenylamino)-pyrimidin-4-yl]-6,8-dimethyl-3,4-dihydro-2H-pyrrolo[1,2-a]pyrazin-1-one [I-6];
7-{2-[4-(4-Acetyl-piperazin-1-yl)-phenylamino]-pyrimidin-4-yl}-6,8-dimethyl-3,4-dihydro-2H-pyrrolo[1,2-a]pyrazin-1-one [I-7]
7-{2-[4-(4-Acetyl-piperazin-1-yl)-3-methyl-phenylamino]-pyrimidin-4-yl}-6,8-dimethyl-3,4-dihydro-2H-pyrrolo[1,2-a]pyrazin-1-one [I-8];
7-{2-[4-(4-Acetyl-piperazin-1-yl)-3-methoxy-phenylamino]-pyrimidin-4-yl}-6,8-dimethyl-3,4-dihydro-2H-pyrrolo[1,2-a]pyrazin-1-one [I-9]
7-{2-[4-((2R,6S)-2,6-Dimethyl-morpholin-4-yl)-phenylamino]-pyrimidin-4-yl}-6,8-dimethyl-3,4-dihydro-2H-pyrrolo[1,2-a]pyrazin-1-one [I-10];
7-[2-(1H-Indazol-6-ylamino)-pyrimidin-4-yl]-6,8-dimethyl-3,4-dihydro-2H-pyrrolo[1,2-a]pyrazin-1-one [I-11];
7-[4-(6,8-Dimethyl-1-oxo-1,2,3,4-tetrahydro-pyrrolo[1,2-a]pyrazin-7-yl)-pyrimidin-2-ylamino]-4H-benzo[1,4]oxazin-3-one [I-12]
7-[2-(4-Diethylamino-phenylamino)-pyrimidin-4-yl]-6,8-dimethyl-3,4-dihydro-2H-pyrrolo[1,2-a]pyrazin-1-one [I-13]
6,8-Dimethyl-7-[2-(6-morpholin-4-yl-pyridin-3-ylamino)-pyrimidin-4-yl]-3,4-dihydro-2H-pyrrolo[1,2-a]pyrazin-1-one [I-13a]
7-[2-(6-Methoxy-pyridin-3-ylamino)-pyrimidin-4-yl]-6,8-dimethyl-3,4-dihydro-2H-pyrrolo[1,2-a]pyrazin-1-one [I-13b];
7-[2-(4-Bromo-phenylamino)-pyrimidin-4-yl]-6,8-dimethyl-3,4-dihydro-2H-pyrrolo[1,2-a]pyrazin-1-one [I-14];
7-{2-[3-(2-Hydroxy-ethanesulfonyl)-phenylamino]-pyrimidin-4-yl}-6,8-dimethyl-3,4-dihydro-2H-pyrrolo[1,2-a]pyrazin-1-one [I-15];
5-[4-(6,8-Dimethyl-1-oxo-1,2,3,4-tetrahydro-pyrrolo[1,2-a]pyrazin-7-yl)-pyrimidin-2-ylamino]-benzo[b]thiophene-2-carboxylic acid [I-16];
7-[2-(4-Hydroxy-phenylamino)-pyrimidin-4-yl]-6,8-dimethyl-3,4-dihydro-2H-pyrrolo[1,2-a]pyrazin-1-one [I-17];
4-[4-(6,8-Dimethyl-1-oxo-1,2,3,4-tetrahydro-pyrrolo[1,2-a]pyrazin-7-yl)-pyrimidin-2-ylamino]-N-isopropyl-2-methoxy-benzenesulfonamide [I-18];
4-[4-(6,8-Dimethyl-1-oxo-1,2,3,4-tetrahydro-pyrrolo[1,2-a]pyrazin-7-yl)-pyrimidin-2-ylamino]-N-isopropyl-benzenesulfonamide [I-19];

N-{4-[4-(6,8-Dimethyl-1-oxo-1,2,3,4-tetrahydro-pyrrolo[1,2-a]pyrazin-7-yl)-pyrimidin-2-ylamino]-phenyl}-methanesulfonamide [I-20];

N-(3-Diethylamino-propyl)-4-[4-(6,8-dimethyl-1-oxo-1,2,3,4-tetrahydro-pyrrolo[1,2-a]pyrazin-7-yl)-pyrimidin-2-ylamino]-2-methyl-benzenesulfonamide [I-21];

7-{2-[3-Methoxy-4-(piperidine-1-sulfonyl)-phenylamino]-pyrimidin-4-yl}-6,8-dimethyl-3,4-dihydro-2H-pyrrolo[1,2-a]pyrazin-1-one [I-22];

N-(2-Dimethylamino-ethyl)-4-[4-(6,8-dimethyl-1-oxo-1,2,3,4-tetrahydro-pyrrolo[1,2-a]pyrazin-7-yl)-pyrimidin-2-ylamino]-2-methoxy-benzenesulfonamide [I-23];

7-{2-[3-Methoxy-4-(4-methyl-piperazine-1-sulfonyl)-phenylamino]-pyrimidin-4-yl}-6,8-dimethyl-3,4-dihydro-2H-pyrrolo[1,2-a]pyrazin-1-one [I-24];

[4-(6,8-Dimethyl-1-oxo-1,2,3,4-tetrahydro-pyrrolo[1,2-a]pyrazin-7-yl)-pyrimidin-2-ylamino]-benzoic acid [I-25];

4-[4-(6,8-Dimethyl-1-oxo-1,2,3,4-tetrahydro-pyrrolo[1,2-a]pyrazin-7-yl)-pyrimidin-2-ylamino]-benzoic acid [I-26];

4-[4-(6,8-Dimethyl-1-oxo-1,2,3,4-tetrahydro-pyrrolo[1,2-a]pyrazin-7-yl)-pyrimidin-2-ylamino]-3-methoxy-benzoic acid [I-27];

7-[2-(3-Hydroxy-4-methoxy-phenylamino)-pyrimidin-4-yl]-6,8-dimethyl-3,4-dihydro-2H-pyrrolo[1,2-a]pyrazin-1-one [I-28];

7-[2-(Benzo[1,3]dioxol-5-ylamino)-pyrimidin-4-yl]-6,8-dimethyl-3,4-dihydro-2H-pyrrolo[1,2-a]pyrazin-1-one [I-29];

6,8-Dimethyl-7-[2-(3-trifluoromethoxy-phenylamino)-pyrimidin-4-yl]-3,4-dihydro-2H-pyrrolo[1,2-a]pyrazin-1-one [I-30];

7-[2-(3-Hydroxy-phenylamino)-pyrimidin-4-yl]-6,8-dimethyl-3,4-dihydro-2H-pyrrolo[1,2-a]pyrazin-1-one [I-31];

7-[2-(3-Methanesulfonyl-phenylamino)-pyrimidin-4-yl]-6,8-dimethyl-3,4-dihydro-2H-pyrrolo[1,2-a]pyrazin-1-one [I-32];

7-[2-(4-Methanesulfonyl-phenylamino)-pyrimidin-4-yl]-6,8-dimethyl-3,4-dihydro-2H-pyrrolo[1,2-a]pyrazin-1-one [I-33];

3-{3-[4-(6,8-Dimethyl-1-oxo-1,2,3,4-tetrahydro-pyrrolo[1,2-a]pyrazin-7-yl)-pyrimidin-2-ylamino]-phenyl}-propionic acid [I-34];

8-Dimethyl-7-{2-[3-(morpholine-4-sulfonyl)-phenylamino]-pyrimidin-4-yl}-3,4-dihydro-2H-pyrrolo[1,2-a]pyrazin-1-one [I-35];

6,8-Dimethyl-7-{2-[4-methyl-3-(morpholine-4-sulfonyl)-phenylamino]-pyrimidin-4-yl}-3,4-dihydro-2H-pyrrolo[1,2-a]pyrazin-1-one [I-36];

6,8-Dimethyl-7-[2-(4-thiomorpholin-4-yl-phenylamino)-pyrimidin-4-yl]-3,4-dihydro-2H-pyrrolo[1,2-a]pyrazin-1-one [I-37];

4-[4-(6,8-Dimethyl-1-oxo-1,2,3,4-tetrahydro-pyrrolo[1,2-a]pyrazin-7-yl)-pyrimidin-2-ylamino]-N-(2-methoxy-ethyl)-benzenesulfonamide [I-38];

6,8-Dimethyl-7-(2-p-tolylamino-pyrimidin-4-yl)-3,4-dihydro-2H-pyrrolo[1,2-a]pyrazin-1-one [I-39];

2-{4-[4-(6,8-Dimethyl-1-oxo-1,2,3,4-tetrahydro-pyrrolo[1,2-a]pyrazin-7-yl)-pyrimidin-2-ylamino]-phenyl}-propionic acid [I-40];

{3-[4-(6,8-Dimethyl-1-oxo-1,2,3,4-tetrahydro-pyrrolo[1,2-a]pyrazin-7-yl)-pyrimidin-2-ylamino]-phenoxy}-acetic acid [I-41];

N-{3-[4-(6,8-Dimethyl-1-oxo-1,2,3,4-tetrahydro-pyrrolo[1,2-a]pyrazin-7-yl)-pyrimidin-2-ylamino]-phenyl}-methanesulfonamide [I-42];

4-[4-(6,8-Dimethyl-1-oxo-1,2,3,4-tetrahydro-pyrrolo[1,2-a]pyrazin-7-yl)-pyrimidin-2-ylamino]-2-methoxy-N-methyl-benzenesulfonamide [I-43];

6,8-Dimethyl-7-{2-[4-(2-oxo-oxazolidin-3-yl)-phenylamino]-pyrimidin-4-yl}-3,4-dihydro-2H-pyrrolo[1,2-a]pyrazin-1-one [I-44];

7-[2-(4H-Benzo[1,3]dioxin-6-ylamino)-pyrimidin-4-yl]-6,8-dimethyl-3,4-dihydro-2H-pyrrolo[1,2-a]pyrazin-1-one [I-45];

6,8-Dimethyl-7-{2-[3-(2-methyl-pyrimidin-4-yl)-phenylamino]-pyrimidin-4-yl}-3,4-dihydro-2H-pyrrolo[1,2-a]pyrazin-1-one [I-46];

N-{2-Chloro-4-[4-(6,8-dimethyl-1-oxo-1,2,3,4-tetrahydro-pyrrolo[1,2-a]pyrazin-7-yl)-pyrimidin-2-ylamino]-phenyl}-acetamide [I-47];

6,8-Dimethyl-7-[2-(2-methyl-1H-indol-5-ylamino)-pyrimidin-4-yl]-3,4-dihydro-2H-pyrrolo[1,2-a]pyrazin-1-one [I-48];

6,8-Dimethyl-7-[2-(3-oxazol-5-yl-phenylamino)-pyrimidin-4-yl]-3,4-dihydro-2H-pyrrolo[1,2-a]pyrazin-1-one [I-49];

6,8-Dimethyl-7-{2-[4-(morpholine-4-sulfonyl)-phenylamino]-pyrimidin-4-yl}-3,4-dihydro-2H-pyrrolo[1,2-a]pyrazin-1-one [I-50];

6,8-Dimethyl-7-{2-[4-(2-morpholin-4-yl-ethoxy)-phenylamino]-pyrimidin-4-yl}-3,4-dihydro-2H-pyrrolo[1,2-a]pyrazin-1-one [I-51];

6,8-Dimethyl-7-[2-(4-oxazol-5-yl-phenylamino)-pyrimidin-4-yl]-3,4-dihydro-2H-pyrrolo[1,2-a]pyrazin-1-one [I-52];

6,8-Dimethyl-7-[2-(3-pyrimidin-5-yl-phenylamino)-pyrimidin-4-yl]-3,4-dihydro-2H-pyrrolo[1,2-a]pyrazin-1-one [I-53];

6,8-Dimethyl-7-[2-(4-pyridin-4-ylmethyl-phenylamino)-pyrimidin-4-yl]-3,4-dihydro-2H-pyrrolo[1,2-a]pyrazin-1-one [I-54];

6,8-Dimethyl-7-{2-[4-(pyrrolidine-1-sulfonyl)-phenylamino]-pyrimidin-4-yl}-3,4-dihydro-2H-pyrrolo[1,2-a]pyrazin-1-one [I-55];

6,8-Dimethyl-7-{2-[4-(piperidine-1-sulfonyl)-phenylamino]-pyrimidin-4-yl}-3,4-dihydro-2H-pyrrolo[1,2-a]pyrazin-1-one [I-56];

7-[2-(4-Benzyloxy-phenylamino)-pyrimidin-4-yl]-6,8-dimethyl-3,4-dihydro-2H-pyrrolo[1,2-a]pyrazin-1-one [I-57];

7-[2-(3-Benzoyl-phenylamino)-pyrimidin-4-yl]-6,8-dimethyl-3,4-dihydro-2H-pyrrolo[1,2-a]pyrazin-1-one [I-58];

N-{3-[4-(6,8-Dimethyl-1-oxo-1,2,3,4-tetrahydro-pyrrolo[1,2-a]pyrazin-7-yl)-pyrimidin-2-ylamino]-phenyl}-acetamide [I-59];

6,8-Dimethyl-7-[2-(4-[1,2,3]thiadiazol-4-yl-phenylamino)-pyrimidin-4-yl]-3,4-dihydro-2H-pyrrolo[1,2-a]pyrazin-1-one [I-60];

6,8-Dimethyl-7-[2-(4-trifluoromethoxy-phenylamino)-pyrimidin-4-yl]-3,4-dihydro-2H-pyrrolo[1,2-a]pyrazin-1-one [I-61];

7-[2-(3,4-Dihydro-2H-benzo[b][1,4]dioxepin-7-ylamino)-pyrimidin-4-yl]-6,8-dimethyl-3,4-dihydro-2H-pyrrolo[1,2-a]pyrazin-1-one [I-62];

7-[2-(2,2-Dioxo-2,3-dihydro-1H-2-benzo[c]thiophen-5-ylamino)-pyrimidin-4-yl]-6,8-dimethyl-3,4-dihydro-2H-pyrrolo[1,2-a]pyrazin-1-one [I-63];

7-[2-(3-Chloro-4-fluoro-phenylamino)-pyrimidin-4-yl]-6,8-dimethyl-3,4-dihydro-2H-pyrrolo[1,2-a]pyrazin-1-one [I-64];

7-[2-(2-Fluoro-phenylamino)-pyrimidin-4-yl]-6,8-dimethyl-3,4-dihydro-2H-pyrrolo[1,2-a]pyrazin-1-one [I-65];

7-[2-(2,4-Difluoro-phenylamino)-pyrimidin-4-yl]-6,8-dimethyl-3,4-dihydro-2H-pyrrolo[1,2-a]pyrazin-1-one [I-66];

7-[2-(3-Chloro-4-methoxy-phenylamino)-pyrimidin-4-yl]-6,8-dimethyl-3,4-dihydro-2H-pyrrolo[1,2-a]pyrazin-1-one [I-67];

6,8-Dimethyl-7-[2-(4-trifluoromethyl-phenylamino)-pyrimidin-4-yl]-3,4-dihydro-2H-pyrrolo[1,2-a]pyrazin-1-one [I-68];

7-[2-(3-Chloro-phenylamino)-pyrimidin-4-yl]-6,8-dimethyl-3,4-dihydro-2H-pyrrolo[1,2-a]pyrazin-1-one [I-69];

{4-[4-(6,8-Dimethyl-1-oxo-1,2,3,4-tetrahydro-pyrrolo[1,2-a]pyrazin-7-yl)-pyrimidin-2-ylamino]-phenyl}-acetic acid [I-70];

6,8-Dimethyl-7-{2-[4-(2-methyl-thiazol-4-yl)-phenylamino]-pyrimidin-4-yl}-3,4-dihydro-2H-pyrrolo[1,2-a]pyrazin-1-one [I-71];

6,8-Dimethyl-7-[2-(4-pyrazol-1-yl-phenylamino)-pyrimidin-4-yl]-3,4-dihydro-2H-pyrrolo[1,2-a]pyrazin-1-one [I-72];

6,8-Dimethyl-7-[2-(4-[1,2,4]triazol-1-yl-phenylamino)-pyrimidin-4-yl]-3,4-dihydro-2H-pyrrolo[1,2-a]pyrazin-1-one [I-73];

6,8-Dimethyl-7-[2-(4-pyrrol-1-yl-phenylamino)-pyrimidin-4-yl]-3,4-dihydro-2H-pyrrolo[1,2-a]pyrazin-1-one [I-74];

7-{2-[4-(2,3-Dihydro-imidazo[2,1-b]thiazol-6-yl)-phenylamino]-pyrimidin-4-yl}-6,8-dimethyl-3,4-dihydro-2H-pyrrolo[1,2-a]pyrazin-1-one [I-75];

7-[2-(3-Methoxy-4-methylamino-phenylamino)-pyrimidin-4-yl]-6,8-dimethyl-3,4-dihydro-2H-pyrrolo[1,2-a]pyrazin-1-one [I-76];

4-[4-(6,8-Dimethyl-1-oxo-1,2,3,4-tetrahydro-pyrrolo[1,2-a]pyrazin-7-yl)-pyrimidin-2-ylamino]-benzonitrile [I-77];

6,8-Dimethyl-7-[2-(4-pyridin-3-yl-phenylamino)-pyrimidin-4-yl]-3,4-dihydro-2H-pyrrolo[1,2-a]pyrazin-1-one [I-78];

6,8-Dimethyl-7-{2-[4-(4-methyl-4H-[1,2,4]triazol-3-yl)-phenylamino]-pyrimidin-4-yl}-3,4-dihydro-2H-pyrrolo[1,2-a]pyrazin-1-one [I-79];

7-{2-[4-(3,5-Dimethyl-pyrazol-1-yl)-phenylamino]-pyrimidin-4-yl}-6,8-dimethyl-3,4-dihydro-2H-pyrrolo[1,2-a]pyrazin-1-one [I-80];

1-{4-[4-(6,8-Dimethyl-1-oxo-1,2,3,4-tetrahydro-pyrrolo[1,2-a]pyrazin-7-yl)-pyrimidin-2-ylamino]-phenyl}-5-methyl-1H-pyrazole-4-carboxylic acid ethyl ester [I-81];

7-[2-(4-Isoxazol-5-yl-phenylamino)-pyrimidin-4-yl]-6,8-dimethyl-3,4-dihydro-2H-pyrrolo[1,2-a]pyrazin-1-one [I-82];

2-(4-{4-[4-(6,8-Dimethyl-1-oxo-1,2,3,4-tetrahydro-pyrrolo[1,2-a]pyrazin-7-yl)-pyrimidin-2-ylamino]-phenyl}-thiazol-2-yl)-acetamide [I-83];

4-{4-[4-(6,8-Dimethyl-1-oxo-1,2,3,4-tetrahydro-pyrrolo[1,2-a]pyrazin-7-yl)-pyrimidin-2-ylamino]-phenyl}-thiazol-2-yl)-acetonitrile [I-84];

7-[2-(2,4-Dimethoxy-phenylamino)-pyrimidin-4-yl]-6,8-dimethyl-3,4-dihydro-2H-pyrrolo[1,2-a]pyrazin-1-one [I-85];

7-[2-(2-Chloro-4-fluoro-phenylamino)-pyrimidin-4-yl]-6,8-dimethyl-3,4-dihydro-2H-pyrrolo[1,2-a]pyrazin-1-one [I-86];

7-[2-(5-Chloro-2-methoxy-phenylamino)-pyrimidin-4-yl]-6,8-dimethyl-3,4-dihydro-2H-pyrrolo[1,2-a]pyrazin-1-one [I-87];

7-[2-(5-Fluoro-2-methyl-phenylamino)-pyrimidin-4-yl]-6,8-dimethyl-3,4-dihydro-2H-pyrrolo[1,2-a]pyrazin-1-one [I-88];

6,8-Dimethyl-7-[2-(4-p-tolyloxy-phenylamino)-pyrimidin-4-yl]-3,4-dihydro-2H-pyrrolo[1,2-a]pyrazin-1-one [I-89];

N-(2-Diethylamino-ethyl)-4-[4-(6,8-dimethyl-1-oxo-1,2,3,4-tetrahydro-pyrrolo[1,2-a]pyrazin-7-yl)-pyrimidin-2-ylamino]-2-methyl-benzenesulfonamide [I-90];

N-(3-Dimethylamino-propyl)-4-[4-(6,8-dimethyl-1-oxo-1,2,3,4-tetrahydro-pyrrolo[1,2-a]pyrazin-7-yl)-pyrimidin-2-ylamino]-2,N-dimethyl-benzenesulfonamide [I-91];

1-{4-[4-(6,8-Dimethyl-1-oxo-1,2,3,4-tetrahydro-pyrrolo[1,2-a]pyrazin-7-yl)-pyrimidin-2-ylamino]-phenyl}-3,5-dimethyl-1H-pyrazole-4-carboxylic acid ethyl ester [I-92];

2,6,8-Trimethyl-7-{2-[3-(2-methyl-pyrimidin-4-yl)-phenylamino]-pyrimidin-4-yl}-3,4-dihydro-2H-pyrrolo[1,2-a]pyrazin-1-one [I-93];

7-[2-(2,2-Dioxo-2,3-dihydro-1H-2-benzo[c]thiophen-5-ylamino)-pyrimidin-4-yl]-2,6,8-trimethyl-3,4-dihydro-2H-pyrrolo[1,2-a]pyrazin-1-one [I-94];

2-Ethyl-6,8-dimethyl-7-{2-[3-(2-methyl-pyrimidin-4-yl)-phenylamino]-pyrimidin-4-yl}-3,4-dihydro-2H-pyrrolo[1,2-a]pyrazin-1-one [I-95];

7-{2-[6-(4-Fluoro-phenoxy)-pyridin-3-ylamino]-pyrimidin-4-yl}-6,8-dimethyl-3,4-dihydro-2H-pyrrolo[1,2-a]pyrazin-1-one [I-95a];

6,8-Dimethyl-7-{2-[4-(1H-tetrazol-5-yl)-phenylamino]-pyrimidin-4-yl}-3,4-dihydro-2H-pyrrolo[1,2-a]pyrazin-1-one [I-95b];

6,8-Dimethyl-7-{2-[3-(piperidine-1-sulfonyl)-phenylamino]-pyrimidin-4-yl}-3,4-dihydro-2H-pyrrolo[1,2-a]pyrazin-1-one [I-95c];

2-{4-[4-(6,8-Dimethyl-1-oxo-1,2,3,4-tetrahydro-pyrrolo[1,2-a]pyrazin-7-yl)-pyrimidin-2-ylamino]-phenyl}-N-(2-methoxy-ethyl)-acetamide [I-96];

N-(2-Dimethylamino-ethyl)-2-{4-[4-(6,8-dimethyl-1-oxo-1,2,3,4-tetrahydro-pyrrolo[1,2-a]pyrazin-7-yl)-pyrimidin-2-ylamino]-phenyl}-N-methyl-acetamide [I-97];

N-(3-Dimethylamino-propyl)-2-{4-[4-(6,8-dimethyl-1-oxo-1,2,3,4-tetrahydro-pyrrolo[1,2-a]pyrazin-7-yl)-pyrimidin-2-ylamino]-phenyl}-N-methyl-acetamide [I-98];

6,8-Dimethyl-7-{2-[4-(2-morpholin-4-yl-2-oxo-ethyl)-phenylamino]-pyrimidin-4-yl}-3,4-dihydro-2H-pyrrolo[1,2-a]pyrazin-1-one [I-99];

7-(2-{4-[2-(4-Acetyl-piperazin-1-yl)-2-oxo-ethyl]-phenylamino}-pyrimidin-4-yl)-6,8-dimethyl-3,4-dihydro-2H-pyrrolo[1,2-a]pyrazin-1-one [I-100];

6,8-Dimethyl-7-(2-{4-[2-(4-methyl-piperazin-1-yl)-2-oxo-ethyl]-phenylamino}-pyrimidin-4-yl)-3,4-dihydro-2H-pyrrolo[1,2-a]pyrazin-1-one [I-101];

2-{4-[4-(6,8-Dimethyl-1-oxo-1,2,3,4-tetrahydro-pyrrolo[1,2-a]pyrazin-7-yl)-pyrimidin-2-ylamino]-phenyl}-acetamide [I-102];

2-{4-[4-(6,8-Dimethyl-1-oxo-1,2,3,4-tetrahydro-pyrrolo[1,2-a]pyrazin-7-yl)-pyrimidin-2-ylamino]-phenyl}-N-methyl-acetamide [I-103];

2-{4-[4-(6,8-Dimethyl-1-oxo-1,2,3,4-tetrahydro-pyrrolo [1,2-a]pyrazin-7-yl)-pyrimidin-2-ylamino]-phenyl}-N, N-dimethyl-acetamide [I-104];

3-{3-[4-(6,8-Dimethyl-1-oxo-1,2,3,4-tetrahydro-pyrrolo [1,2-a]pyrazin-7-yl)-pyrimidin-2-ylamino]-phenyl}-N- (2-methoxy-ethyl)-propionamide [I-105];

N-(2-Dimethylamino-ethyl)-3-{3-[4-(6,8-dimethyl-1- oxo-1,2,3,4-tetrahydro-pyrrolo[1,2-a]pyrazin-7-yl)-py- rimidin-2-ylamino]-phenyl}-N-methyl-propionamide [I-106];

N-(3-Dimethylamino-propyl)-3-{3-[4-(6,8-dimethyl-1- oxo-1,2,3,4-tetrahydro-pyrrolo[1,2-a]pyrazin-7-yl)-py- rimidin-2-ylamino]-phenyl}-N-methyl-propionamide [I-107];

6,8-Dimethyl-7-{2-[3-(3-morpholin-4-yl-3-oxo-propyl)- phenylamino]-pyrimidin-4-yl}-3,4-dihydro-2H-pyr- rolo[1,2-a]pyrazin-1-one [I-108];

7-(2-{3-[3-(4-Acetyl-piperazin-1-yl)-3-oxo-propyl]-phe- nylamino}-pyrimidin-4-yl)-6,8-dimethyl-3,4-dihydro- 2H-pyrrolo[1,2-a]pyrazin-1-one [I-109];

6,8-Dimethyl-7-(2-{3-[3-(4-methyl-piperazin-1-yl)-3- oxo-propyl]-phenylamino}-pyrimidin-4-yl)-3,4-dihy- dro-2H-pyrrolo[1,2-a]pyrazin-1-one [I-110];

3-{3-[4-(6,8-Dimethyl-1-oxo-1,2,3,4-tetrahydro-pyrrolo [1,2-a]pyrazin-7-yl)-pyrimidin-2-ylamino]-phenyl}- propionamide [I-111];

3-{3-[4-(6,8-Dimethyl-1-oxo-1,2,3,4-tetrahydro-pyrrolo [1,2-a]pyrazin-7-yl)-pyrimidin-2-ylamino]-phenyl}-N- methyl-propionamide [I-112];

3-{3-[4-(6,8-Dimethyl-1-oxo-1,2,3,4-tetrahydro-pyrrolo [1,2-a]pyrazin-7-yl)-pyrimidin-2-ylamino]-phenyl}-N, N-dimethyl-propionamide [I-113];

4-[4-(6,8-Dimethyl-1-oxo-1,2,3,4-tetrahydro-pyrrolo[1, 2-a]pyrazin-7-yl)-pyrimidin-2-ylamino]-3-methoxy-N- (1-methyl-piperidin-4-yl)-benzamide [I-114]; and 4-[4-(6,8-Dimethyl-1-oxo-1,2,3,4-tetrahydro-pyrrolo[1, 2-a]pyrazin-7-yl)-pyrimidin-2-ylamino]-N-(1-methyl- piperidin-4-yl)-benzamide [I-115].

and pharmaceutically acceptable salts thereof.

34. A pharmaceutical composition comprising a compound according to claim 1 admixed with a pharmaceutically acceptable diluent, excipient or carrier.

35. A method of treating a cancer or leukemia, said method comprising administering to a mammal in need thereof a therapeutically effective amount of a compound according to claim 1, wherein said compound is an Aurora kinase inhibitor, such that said cancer or leukemia is treated.

36. The method according to claim 35 wherein the compound is administered in an amount sufficient to inhibit aurora kinase.

37. The method according to claim 36 wherein the aurora kinase is aurora kinase A, aurora kinase B or aurora kinase C.

38. A method of identifying further candidate compounds capable of inhibiting one or more of a cyclin dependent kinase, an aurora kinase, GSK, a tyrosine kinase, and a PLK enzyme, comprising using a compound according to claim 1 in an assay for identifying further candidate compounds capable of inhibiting one or more of a cyclin dependent kinase, an aurora kinase, GSK, a tyrosine kinase and a PLK enzyme.

39. The method according to claim 38 wherein said assay is a competitive binding assay.

40. The method according to claim 39 wherein said competitive binding assay comprises contacting the compound with an enzyme selected from a cyclin dependent kinase, GSK, a tyrosine kinase and PLK, and a candidate compound and detecting any change in the interaction between the compound and the enzyme.

41. A process for preparing a compound of formula I as defined in claim 1, said process comprising the steps of:

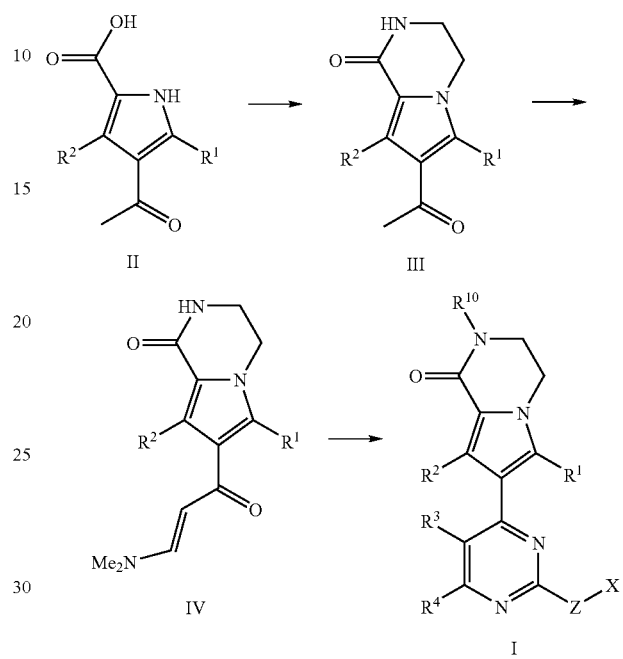

(i) converting a compound of formula II to a compound of formula III;
(ii) converting said compound of formula III to a compound of formula IV;
(iii) converting said compound of formula IV to a compound of formula I.

42. A process according to claim 41 wherein step (i) comprises reacting a compound of formula II with 2-chloroethyl amine hydrochloride, V,

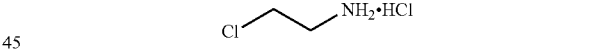

to form a compound of formula III.

43. A process according to claim 42 wherein step (i) is carried out in the presence of carbonyldiimidazole in anhydrous DMF.

44. A process according to claim 41 wherein step (ii) comprises reacting said compound of formula III with a compound of formula VI,

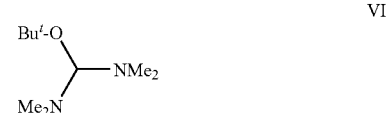

to form a compound of formula IV.

45. A process according to claim 41 wherein step (iii) comprises reacting said compound of formula IV with a compound of formula VII

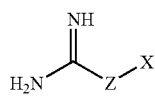

where Z and X are as defined in claim 1, to form a compound of formula I.

46. A process according to claim 45 wherein step (iii) comprises reacting said compound of formula IV with a compound of formula VIIa

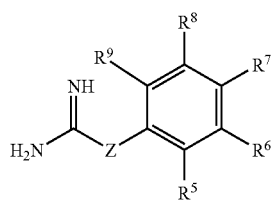

where Z and $R^5$-$R^9$ are as defined in claim 1, to form a compound of formula Ia as defined in claim 16.

47. A process for preparing a compound of formula I as defined in claim 1, said process comprising the steps of:

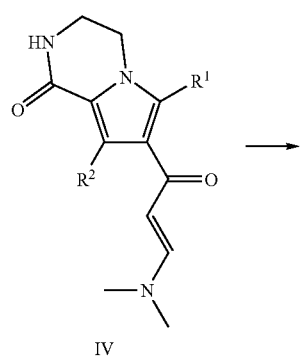

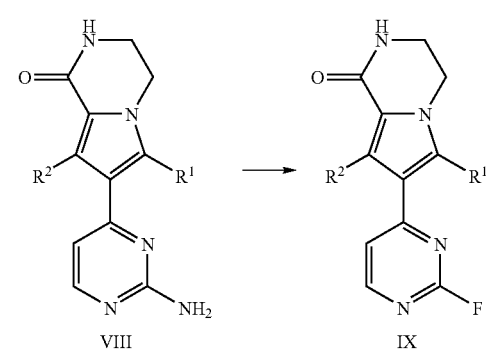

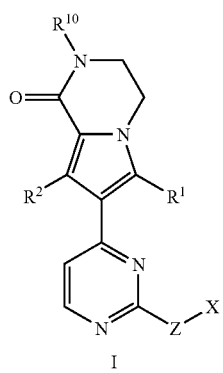

(i) preparing a compound of formula IV;
(ii) converting said compound of formula IV into a compound of formula VIII;
(iii) converting said compound of formula VIII into a compound of formula IX;
(iv) converting said compound of formula IX into a compound of formula I.

48. A process according to claim 47 wherein step (ii) comprises reacting said compound of formula IV with guanidine HCl and sodium ethoxide in ethanol.

49. A process according to claim 47 wherein step (iii) comprises reacting said compound of formula VIII with HF/pyridine and t-butyl nitrite.

50. A process according to claim 47 wherein Z is NH and step (iv) comprises reacting said compound of formula IX with $NH_2$—X.

51. A process according to claim 50 wherein Z is NH and step (iv) comprises reacting said compound of formula IX with an aniline of formula XI

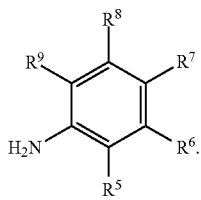

52. A process according to claim 47 wherein Z is NH and $R^{10} \neq H$, and step (iv) comprises reacting said compound of formula IX with an alkyl halide, $R^{10}$-Hal, and converting the product so formed into a compound of formula I by treating with $NH_2$—X.

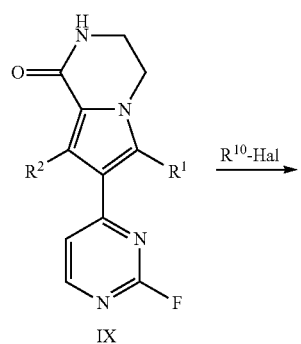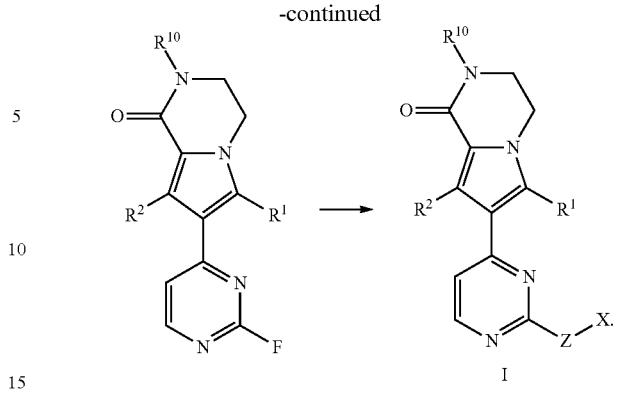
* * * * *

UNITED STATES PATENT AND TRADEMARK OFFICE
CERTIFICATE OF CORRECTION

| | | |
|---|---|---|
| PATENT NO. | : 8,404,692 B2 | Page 1 of 1 |
| APPLICATION NO. | : 12/083534 | |
| DATED | : March 26, 2013 | |
| INVENTOR(S) | : Jones et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1251 days.

Signed and Sealed this
Sixteenth Day of July, 2013

Teresa Stanek Rea
*Acting Director of the United States Patent and Trademark Office*